United States Patent [19]
Londesborough et al.

[11] Patent Number: 5,792,921
[45] Date of Patent: Aug. 11, 1998

[54] INCREASING THE TREHALOSE CONTENT OF ORGANISMS BY TRANSFORMING THEM WITH COMBINATIONS OF THE STRUCTURAL GENES FOR TREHALOSE SYNTHASE

[76] Inventors: John Londesborough, Jääkärinkatu 9A15, Helsinki 15; Outi Tunnela née Vuorio, Kaskenpäänkuja 4A2, Espoo SF-02340, both of Finland; Tapio Palva, Drottninggatan 5, S-753 10, Uppsala, Sweden; Kjell-Ove Holmström, Flogstavägen 81 E, S-752 63, Uppsala, Sweden; Björn Welin, Cellovägen 5K, S-756 54, Uppsala, Sweden; Abul Mandal, Dirigentvägen 179, S-756 54, Uppsala, Sweden

[21] Appl. No.: 290,301

[22] Filed: Aug. 15, 1994

Related U.S. Application Data

[63] Continuation-in-part of PCT/FI93/00049 Feb. 15, 1993, and a continuation-in-part of Ser. No. 841,997, Feb. 28, 1992, Pat. No. 5,422,254, which is a continuation of Ser. No. 836,021, Feb. 14, 1992, abandoned.

[30] Foreign Application Priority Data

Jun. 29, 1994 [FI] Finland ................... 943133

[51] Int. Cl.[6] ............ C12N 15/29; C12N 15/82; A01H 4/00; A01H 5/00
[52] U.S. Cl. ............ 800/205; 800/250; 800/255; 800/DIG. 24; 800/DIG. 26; 800/DIG. 27; 800/DIG. 43; 800/DIG. 45; 800/DIG. 25; 800/DIG. 52; 800/DIG. 56; 435/240.4; 435/69.1; 435/172.3; 536/23.7; 536/24.1
[58] Field of Search ................... 800/205, 250, 800/255, DIG. 24, DIG. 26, DIG. 27, DIG. 45, DIG. 43, DIG. 25, DIG. 52, DIG. 56; 435/240.4, 172.3, 69.1; 536/23.7, 24.1

[56] References Cited

PUBLICATIONS

Naploi et al. Introduction of a Chimeric Chalcone Synthase Gene into Petunia Results in Reversible Co-Suppression of Homologous Genes in trans. The Plant Cell, vol. 2 279–289, Apr. 1990.

Veluthambi et al. Trehalose Toxicity in *Cuscuta reflexa*. Plant Physiol. (1981) 68, 1369–1374.

*Primary Examiner*—Douglas W. Robinson
*Assistant Examiner*—Thomas Haas
*Attorney, Agent, or Firm*—Kubovcik & Kubovcik

[57] ABSTRACT

Two nucleotide sequences encoding two different polypeptides found in yeast trehalose synthase have been isolated and cloned. A third polypeptide has been isolated from the enzyme and characterized, and a method is provided to isolate and clone the nucleotide sequence encoding this polypeptide. The coding sequences can be inserted into suitable vectors and used to transform host cells. The transformed cells will produce increased amounts of trehalose compared to the untransformed wild types and have increased tolerance to a variety of stresses, in particular to decreased availability of water. The invention may be used to improve the stress tolerance of organisms, to increase the storage life of foodstuffs and to produce trehalose economically on an industrial scale in an organism (e.g. baker's yeast) that is a traditional and safe foodstuff.

23 Claims, 31 Drawing Sheets

Promoter

```
TTGTTGCGAT TGTTCTGTTC CATCTGCACC AGAACAAAGA ACAAAAGAAC  -396
AAGGAACAAA GTCCAAGCAC GTCAGCGCTG TTTATAAGGG GATTGACGAG  -346
GGATCGGGCC TAGAGTGCCA GCGCGCCAGG GAGAGGGAGC CCCCTGGGCC  -296
CTCATCCGCA GGCTGATAGG GGTCACCCCG CTGGGCAGGT CAGGGCAGGG  -246
GCTCTCAGGG GGGCGCCATG GACAAACTGC ACTGAGGTTC TAAGACACAT  -196
GTATTATTGT GAGTATGTAT ATATAGAGAG AGATTAAGGC GTACAGCCGG  -146
GTGGTAGAGA TTGATTAACT TGGTAGTCTT ATCTTGTCAA TTGAGTTTCT   -96
GTCAGTTTCT TCTTGAACAA GCACGCAGCT AAGTAAGCAA CAAAGCAGGC   -46
TAACAAACTA GGTACTCACA TACAGACTTA TTAAGACATA GAACT ATG    +3
```

Terminator

```
ACC AAA AAC TGA TGA ACCCGATGCA AATGAGACGA TCGTCTATTC    -1521
CTGGTCCGGT TTTCTCTGCC CTCTCTTCTA TTCACTTTTT TTATACTTTA  +1571
TATAAAATTA TATAAATGAC ATAACTGAAA CGCCACACGT CCTCTCCTAT  +1621
TCGTTAACGC CTGTCTGTAG CGCTGTTACT GAAGCTGCGC AAGTAGTTTT  +1671
TTCACCGTAT AGGCC                                        +1686
```

Promoter

```
TGTAGTAACT TATTGCGAAA TTTCTGCTCT TCTCGTCTCG CTCAAAAATC  -392
GCGTTCAGGG TAAAAGGGGC GAAACAGAGG GCCAGATAGA AATTTCGAGA  -342
AAACGGGTCA CCCCGCCCCT GCATTTTGAT ATGGCGTATT TGGGATTGCT  -292
TGCTCGAAAG TGTCTAAGTC CGGCTGGCGG GCCTGGCGCC CTCGCCGAAG  -242
GGAGATAGGA AGGGCGGGG GTCCGGGCAG CGGCTATGGT GTCAGTTACC  -192
TAGGGAAGGA GAAGGGGGTA GAACCAAGGG GCTAGCACAC TCACCCTGGG  -142
GCCCCCGTCT AGCCAAGCTT AAATATAAAT ACTAATGTAA CTATAAATAT  -92
AAGGATCTAC CGTGTCATTG CACATCCACC CACCCGTCGA TTAAAAAACC  -42
AAACAAAGCA AAGAATACAA TAGCAACGCA AGATCAACAC A ATG GCT  +6
```

Terminator

```
TTC ACG ATC ATT TCA AGA ATC ATT GAA GAT TAA ATTTTACCAT  +3307
TTTAAAATTT TAATGTTCTT GGGTATGAAC TTTTATTTTC AACTGCTTAT  +3357
TATATATCAA TTCTATAAAT TTTTTCTTC TCTCTAACGA CCAATTATAA  +3407
AATTCATCCT CTTATTTATT ACAGCATCTT ATACATTATG TATATGGGTA  +3457
GCTATTATTC ATTTTTGCTT CGTAAGGACT TTTTTTGTCA ACTTTTTCAT  +3507
CCTAAGCGGC TAAAAGTGAT TGGAGAGGAA TGtccaggcg accaatgata  +3557
aaaacgcttt ctcttggaac aagaaatagg agcaattgac agttgtcgat  +3607
```

Length = 511     Identities = 188     Gaps = 32

Identities/Length = 36.8 %

FIG. 5C

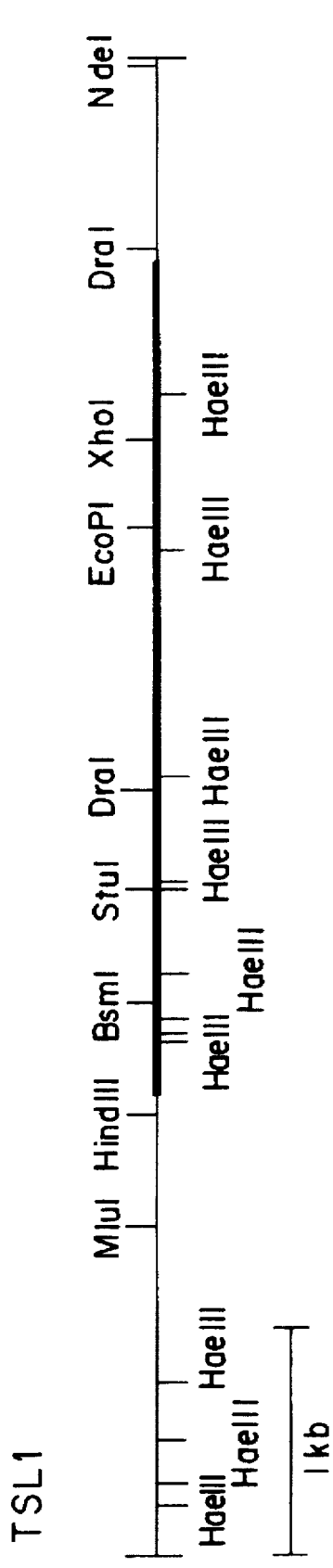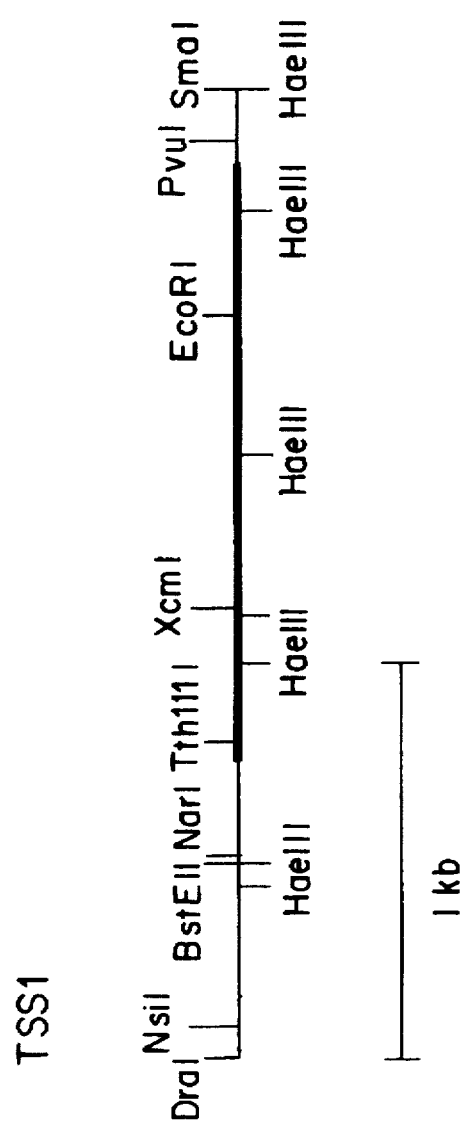
FIG. 6A
FIG. 6B

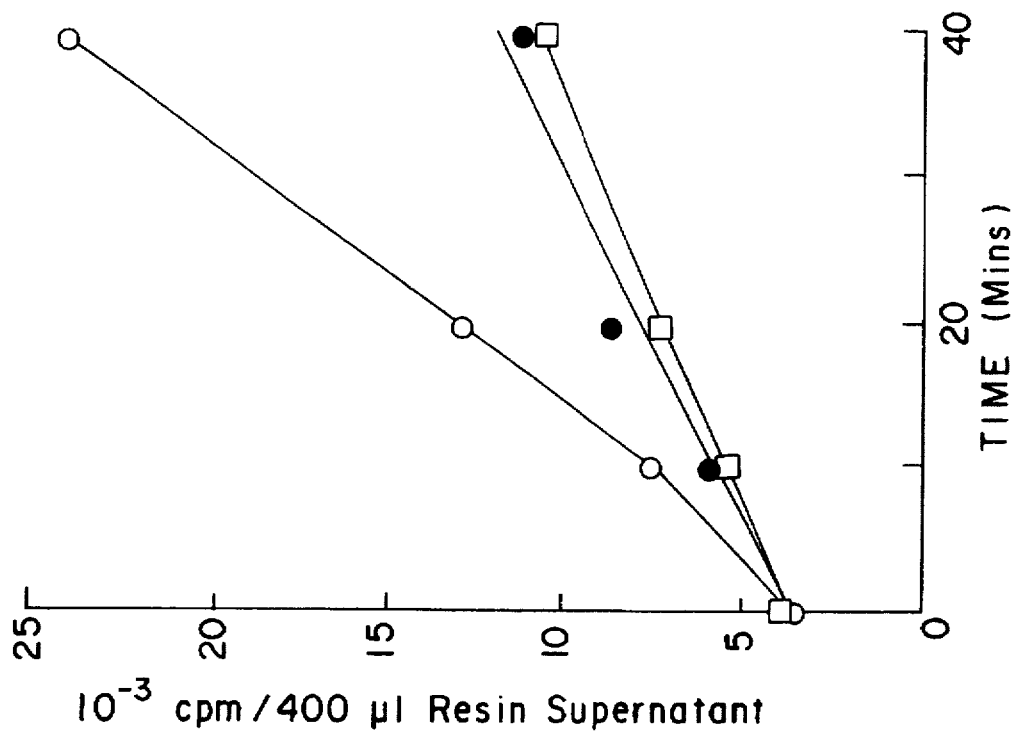
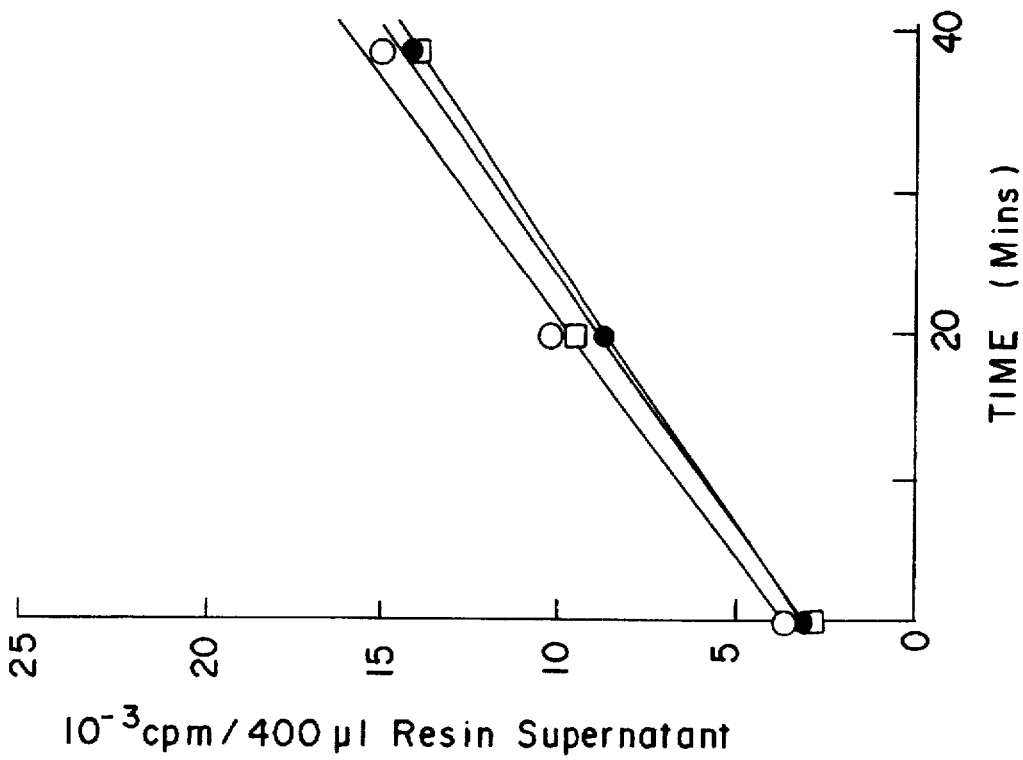

E: EcoI    M: MluI    X: XbaI    S: SphI 5,792,921

INCREASING THE TREHALOSE CONTENT OF ORGANISMS BY TRANSFORMING THEM WITH COMBINATIONS OF THE STRUCTURAL GENES FOR TREHALOSE SYNTHASE

This application is a continuation-in-part of International Application No. PCT/FI93/00049 filed Feb. 15th, 1993, and which designates the United States, and of U.S. patent application Ser. No. 07/841,997, filed Feb. 28th, 1992 now U.S. Pat. No. 5,422,254, and which, in turn, is a continuation of U.S. patent application Ser. No. 07/836,021, filed Feb. 14th, 1992, and now abandoned.

FIELD OF INVENTION

This invention relates to the genetic engineering of the trehalose synthetic pathway of yeasts, especially baker's and distiller's yeasts, and to the transfer of this pathway by genetic engineering to other organisms. It relates to the production of trehalose and ethanol and to the improvement of the stress resistance of organisms, especially yeasts and crop plants.

BACKGROUND OF THE INVENTION

It is well known that sugars and other polyhydric compounds stabilize isolated proteins and phospholipid membranes during dehydration, probably by replacing the water molecules that are hydrogen-bonded to these macromolecules [reviewed by Crowe, J. H. et al. (1987) Biochemical Journal 242, 1–10]. Trehalose (α-glucopyranosyl-α-D-glucopyranose) is a dimer of two glucose molecules linked through their reducing groups. Because it has no reducing groups, it does not take part in the Maillard reactions that cause many sugars to damage proteins, and it is one of the most effective known protectants of proteins and biological membranes in vitro.

In nature, trehalose is found at high concentrations in yeasts and other fungi, some bacteria, insects, and some litoral animals, such as the brine shrimp. It is notable that all these organisms are frequently exposed to osmotic and dehydration stress. Accumulation of trehalose in higher plants is rare, but high levels occur in the so-called resurrection plants, such as the pteridophyte, Selaginella lepidophylla, which can survive extended drought [Quillet, M. and Soulet, M. (1964) Comptes Rendus de l'Academie des Sciences, Paris 259, pp. 635–637; reviewed by Avigad, G. (1982) in Encyclopedia of Plant Research (New Series) 13A, pp. 217–347].

A decreased availability of intracellular water to proteins and membranes is a common feature not only of dehydration and osmotic stress, but also of freezing, in which ice formation withdraws water from inside the cells, and heat stress, which weakens the hydrogen bonds between water and biological macromolecules. In recent years several publications have shown a close connection between the trehalose content of yeast cells, especially of the species Saccharomyces cerevisiae, and their resistance to dehydration and osmotic, freezing and heat stresses. This work has lead to the concept [summarized by Wiemken, A. (1990) Antonie van Leeuwenhoek 58, 209–217] that, whereas the main storage or reserve carbohydrate in yeast is glycogen, the prime physiological function of trehalose is as a protectant against these and other stresses, including starvation and even poisoning by copper, ethanol and hydrogen peroxide, which all stimulate trehalose accumulation [Attfield, P. V. (1987) Federation of European Biochemical Societies Letters 225, 259–263].

Thus, during growth of Saccharomyces cerevisiae on glucose, glycogen begins to accumulate about one generation before the glucose is exhausted, and begins to be steadily consumed as soon as all external carbon supplies are exhausted. In contrast, accumulation of trehalose (partly at the expense of glycogen) only begins after all the glucose has been consumed, and the trehalose level is then maintained until nearly all the glycogen has been consumed [Lillie, S. A. & Pringle, J. R. (1980) Journal of Bacteriology 143, 1384–1394]. The eventual consumption of trehalose is accompanied by a rapid decrease in the number of viable cells.

When trehalose levels in S. cerevisiae have been manipulated by varying the growth conditions or administering heat shocks, high positive correlations have been found between the trehalose content of the cells and their resistance to dehydration [Gadd, G. et al. (1987) Federation of European Microbiological Societies Microbiological Letters 48, 249–254], heat stress [Hottiger, T. et al., (1987) Federation of European Biochemical Societies Letters 220, 113–115] and freezing [Gélinas, P. et al. Applied and Environmental Microbiology 55, 2453–2459]. Also, strains of S. cerevisiae and other yeasts selected for resistance to osmotic stress [D'Amore, T. et al. (1991) Journal of Industrial Microbiology 7, 191–196] or high performance in frozen dough fermentation [Oda, Y. (1986) Applied and Environmental Microbiology 52, 941–943] were found to have unusually high trehalose contents. Furthermore, a mutation in the cyclic AMP signaling system of S. cerevisiae that causes constitutive high trehalose levels also causes constitutive thermotolerance, whereas another mutation in this system that prevents the usual rise in trehalose during heat shock also prevents the acquisition of thermotolerance [Hottiger, T. et al., (1989) Federation of European Biochemical Societies Letters 255, 431–434]. Thus, there is much evidence pointing to a connection between trehalose content and stress resistance in yeasts, especially S. cerevisiae. Similar findings have been made for several other fungi [e.g., Neves, M. J., Jorge, J. A., Francois, J. M. & Terenzi, H. F. (1991) Federation of European Biochemical Societies Letters 283, 19–22]. However, a causative relationship has not yet been demonstrated. Further, nearly all conditions that cause increases in the trehalose content of yeast also cause increases in the levels of the so-called heat shock proteins. The 1989 publication of Hottiger and colleagues, cited above, claims that canavanine does not cause an increase in either trehalose levels or thermotolerance, whereas this compound is reported to induce heat shock proteins.

Whether or not there is a causal relation between trehalose content and stress resistance, it has become general practice in the manufacture of baker's yeast to maximise the trehalose content of the yeast. Various maturation processes have been developed to achieve this aim, and they are of crucial importance in the manufacture of active dried yeast. The details of these processes are often secret, but they are generally empirical regimes in which carbon and nitrogen feeds, aeration and temperature are carefully controlled and selected strains of yeast are used. They demand time and energy inputs during which little increase in cell number occurs. A more rational and controlled process would be of economic benefit.

According to Cabib, E. & Leloir, L. F. [(1957) Journal of Biological Chemistry 231, 259–275], trehalose is synthesized in yeast from uridine diphosphoglucose (UDPG) and glucose-6-phosphate (G6P) by the sequential action of two enzyme activities, trehalose-6-phosphate synthase (Tre6P synthase) and trehalose-6-phosphate phosphatase (Tre6Pase). Londesborough. J. & Vuorio, O. [(1991) Journal of Microbiology 137, 323-330, expressly incorporated herein by reference] have purified from baker's yeast a proteolytically modified protein complex that exhibited both these activities and appeared to contain a short polypeptide chain (57 kDa) and two truncated versions (86 kDa and 93 kDa) of a long polypeptide chain. The intact long chain was estimated to have a mass of at least 115 kDa. It was not disclosed which enzyme activity or activities was associated with which polypeptide, nor indeed whether both polypeptides were essential for either or both enzymatic activities. Anti-sera against both polypeptides were reported, but no amino acid sequences were disclosed.

An earlier patent application [EP 451 896; see claim 1] has claimed for a transformed yeast "comprising . . . one gene encoding . . . trehalose-6-phosphate synthase". However, no information about either the gene or the protein it encodes was provided.

Several authors have reported increases in Tre6P synthase activity in conditions that lead to accumulation of trehalose by S. cerevisiae, and Schizosaccharomyces pombe both during the approach to stationary phase [Winkler, K., et al. (1991) Federation of European Biochemical Societies Letters 291, 269-272; Francois, J., et al. (1991) Yeast 7, 575-587] and after temperature shift-ups to about 40° C. [De Virgilio, C., et al. (1990) Federation of European Biochemical, Societies Letters 273, 107-110]. Panek and her colleagues [Panek, A. C., et al. (1987) Current Genetics 11, 459-465] have claimed that Tre6P synthase activity is increased by dephosphorylation of pre-existing enzyme molecules, i.e., that it is the result of post-translational regulation. This claim has been challenged [Vandercammen, A., et al., (1989) European Journal of Biochemistry 182, 613-620] but continues to be made [Panek, A. D. & Panek, A. C. (1990) Journal of Biotechnology 14, 229-238]. Evidence for or against an increase in the amount of enzyme during trehalose accumulation is conflicting. Inhibitors of mRNA synthesis inhibited trehalose accumulation by S. cerevisiae shifted from 30° to 45° C. [Attfield (1987) loc.cit.], whereas under very similar conditions Winkler et al [1991) loc.cit.] found that cycloheximide (an inhibitor of protein synthesis) did not prevent the accumulation of trehalose, which, however, occurred without an observable increase in Tre6P synthase activity. In a lower temperature range (a shift from 23° to 36° C.), trehalose accumulation was accompanied by a three-fold increase in Tre6P synthase activity, and cycloheximide prevented the increase in Tre6P synthase [Panek, A. C., et al. (1990) Biochemie 72, 77-79]. In Schizosaccharomyces pombe, [De Virgilio, C., et al. (1991) loc. cit.] temperature shiftup caused a large accumulation of trehalose and increase of Tre6P synthase which were not prevented by cycloheximide, leading the authors to suggest that in this yeast a post-translational activation occurs. We now disclose that in S. cerevisiae the co-ordinate increases in Tre6P synthase and Tre6Pase activities during exhaustion of glucose are accompanied by an increase in antigenic material recognized by anti-sera to the short and long chains of a purified trehalose synthase. Hence, a method to increase the trehalose content of cells, and so, their stress tolerance, would be to isolate, clone, and modify the structural genes (hereinafter referred to as TPS1, TSL1, and TSL2) of these polypeptides and cause their expression in yeast or other host cells under the control of suitable promoters. If the expression of these genes could be controlled, then so could the trehalose content of the host cells.

The well known metabolic theory of Kacser & Burns [(1973) Symposium of the Society of Experimental Biology 27, 65-107] teaches that in principle the concentration of any intermediate, such as trehalose, can be increased by increasing the amount of any enzyme synthesizing it or decreasing the amount of any enzyme degrading it, but that the size of the increase may not be significant. The novelty of the present invention lies in the identification and characterization of the particular yeast genes that must be modified to increase the amounts of trehalose synthase and the recognition of the advantages of modifying the synthetic pathway rather than the degradative pathway. These advantages include (i) leaving the highly regulated [see, e.g., Thevelein, J. M. (1988) Experimental Mycology 12, 1-12] degradative pathway intact to avoid the physiological problems likely in yeast that cannot activate this pathway, (ii) the possibility of causing yeast to synthesize trehalose under physiological conditions where wild type yeasts do not (so that blocking the degradative pathway cannot increase the amount of trehalose) and (iii) the important possibility of introducing by these genes a trehalose-synthetic capacity to organisms, such as most higher plants, that naturally lack this capacity.

Expression of the genes for trehalose synthesis in yeast under conditions where trehalase is active will increase the operation of a so-called "futile" cycle, in which glucose is continuously phosphorylated, converted to trehalose and regenerated by hydrolysis of the trehalose, resulting in increased consumption of ATP. This ATP must be regenerated, and under fermentative conditions this will occur by conversion of sugars into ethanol. Therefore, introduction of TPS1, TSL1 and TSL2 into yeast under the control of promoters active under fermentative conditions is expected to decrease the yield of cell mass on carbon source and increase that of ethanol. The many attempts [e.g., Schaaf et al. (1989) Yeast 5, 285-290] to increase fermentation rates in yeast by increasing the levels of glycolytic enzymes have been unsuccessful. The probable reason is that availability of ADP limits the rate of glycolysis in yeast. Introduction of a futile cycle-ATPase is thus expected to increase this rate. The feasibility of this invention is demonstrated by the finding [Gancedo, J.- M. & Navas, M. A. (1992) Yeast 8, S574] that expression of the gluconeogenic enzymes, fructose bisphosphatase and phosphoenol-pyruvate carboxykinase under fermentative conditions (so causing two futile cycles) caused a 50% increase in the fermentation rate of resting yeast. Use of the trehalose futile cycle has the added advantage that the cells must then contain a steady state level of trehalose, which increases their tolerance to osmotic and temperature stress.

The present invention includes transformed strains of distiller's yeast, in which the presence of modified forms of any or all of TPS1, TSL1 and TSL2 results in an increased yield of ethanol from carbohydrate sources.

As well as being used to improve the properties of yeast, especially active dried yeast and yeast for frozen doughs, this invention has other obvious applications. First, by increasing the proportion of trehalose in yeast, the industrial scale production of trehalose from yeast is made more economic. It is particularly advantageous to obtain trehalose from yeast because, since yeast is a traditional and safe food stuff, a minimal purification of the trehalose will often be adequate: preparations of trehalose containing yeast residues could be safely added to food stuffs for human or animal consumption. Trehalose also has medical applications, both as a stabilizer of diagnostic kits, viruses and other protein material [WO 87/00196] and, potentially, as a source of anti-tumour agents [Ohtsuro et al. (1991) Immunology 74, 497-503]. Trehalose for internal applications in humans would be much more safely obtained from yeast than from a genetically engineered bacterium.

Second, by transferring these genes to higher plants after making suitable modifications obvious to anyone skilled in the art (in general, replacements of adenine/thymine base pairs by guanine/cytosine base pairs as suggested by Perlak et al. [(1991) Proceedings of the National Academy of Sciences of the U.S.A. 88, 3324–3328] and the introduction of suitable promoters, some of which may be tissue-specific, to direct the synthesis of trehalose to frost and drought-sensitive tissues), the resistance of the plants to various stresses, especially frost and dehydration, should be improved. Other microbial trehalose synthases could also be used, including those of *Candida utilis* (Soler et al [1989] FEMS Microbiol Letters 61, 273–278), *E. coli* (Glaever et al [1988] J. Bacteriol. 170, 2841–2849), *Dictyostelium discoideum* (Killick [1979] Arch. Biochem. Biophys. 196, 121–133) and *Mycobacterium smegmatis* (Lapp et al [1971] J. Biol. Chem. 246, 4567–4579), the latter two systems being able to use ADPG as an alternative to UDPG. The economic importance of such improvements is potentially enormous, because even small increases in cold-tolerance will lead to large increases in growing season, whereas dehydration resistance can save entire crops in time of drought. Frost and drought resistance in higher plants is usually accompanied by increases in compounds such as proline rather than trehalose [reviewed by Stewart (1989) in "Plants under Stress", pp 115–130], but, as mentioned above, resurrection plants accumulate large amounts of trehalose and there seems, a priori, to be no reason why this strategy should not be successful. Therefore, the present invention includes a process to transform crop plants by introducing recombinant forms of the structural genes for microbial trehalose synthases (such as the TPS1, TSL1 and TSL2 genes for the yeast enzyme) so as to increase the trehalose content of some of their tissues compared to those of the untransformed plant. Such transformed plants can also be economic and safe sources of trehalose. Third, the shelf-life of food products can be increased by adding trehalose to them [WO 89/00012]. A further aspect of the present invention is a novel process for producing trehalose-enriched food products from plants by causing them to express the structural genes for a microbial trehalose synthase in their edible tissues.

SUMMARY OF INVENTION

The present invention provides two isolated genes encoding, respectively a short and a long chain of yeast trehalose synthase and a third gene encoding a 99 kDa polypeptide that occurs in some trehalose synthase preparations and has trehalose-6-phosphatase activity. These genes can be used to transform an organism (such as a yeast, other fungus or higher eukaryote), whereby the transformed organism produces more trehalose synthase resulting in a trehalose content higher than that of the parent organism. The higher trehalose content confers improved stress resistance and storage properties on the transformed organism as compared to the parent organism, and the transformed organism can be used to provide large quantities of trehalose. The invention also teaches the use of trehalose synthase genes controlled by non-constitutive promoters so that the trehalose content of the transformed organism increases in a desired growth phase or under particular environmental conditions when such an increase is advantageous.

A 6–13 %T gradient gel was used. Lane 1 contains 8.3 µg of intact trehalose synthase eluted from the UDPG-Glucuronate-Agarose column with 0.2M NaCl (#11 of Table 1). Lanes 2, 3 and 4 contain, respectively, 7.7, 12 and 1.0 µg of enzyme eluted from the column with 0.4M NaCl containing 10 mM UDPG (#13, #14 and #15 from Table 1). Lane 5 contains about 1 µg each of molecular mass markers (myosin, β-galactosidase, α-phosphorylase, BSA, ovalbumin, lactate dehydrogenase, triosephosphate-isomerase, myoglobin and cytochrome c). The major polypeptides of intact trehalose synthase are named on the left and the molecular mass calibration, in kDa, is shown on the right.

Figure 1:
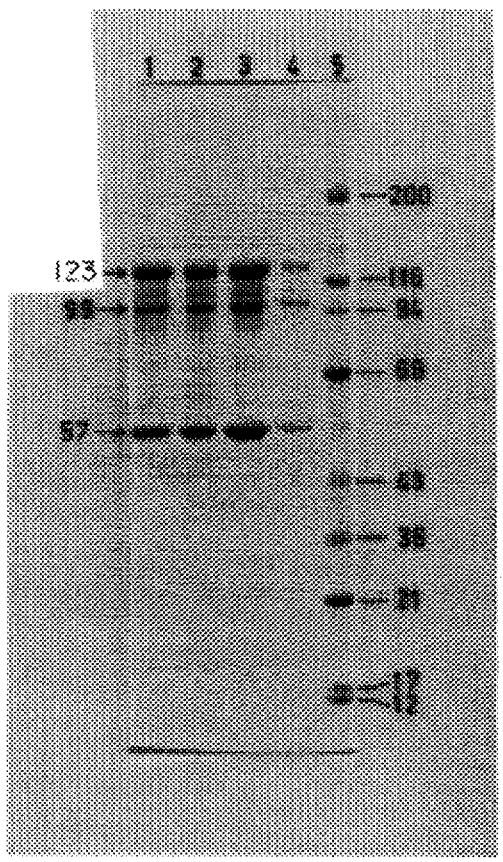
FIG. 1. SDS-PAGE of intact trehalose synthase
Figure 2:
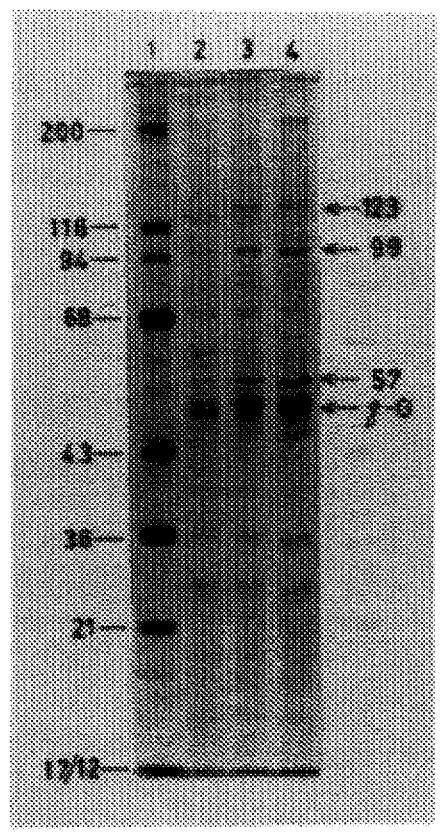

FIG. 2. SDS-PAGE of immunoprecipitates of wild-type yeast grown on YP/2% glucose A 9 %T gel was used. Lane 1 contains about 1 µg each of the molecular mass markers used in FIG. 1. Lanes 2, 3 and 4 contain immunoprecipitates from 3.8 mg fresh yeast harvested after 16.1 h (1.2% residual glucose), 18.1 h (no residual glucose) and 39 h. The molecular mass calibration is shown on the left and the major polypeptides of trehalose synthase and the heavy chain of γ-globulin are shown on the right.

FIG. 3. The promoter and terminator of TPS1 and the amino acid sequence deduced from its ORF.

(a) In the promoter and terminator regions, the start ATG and tandem TGA stop codons are bold and underlined and a TATA box and putative catabolite repression element are underlined. (b) In the amino acid sequence (SEQ ID NO:2), the sequences found in peptides isolated from the short chain of trehalose synthase are underlined.

Figure 4B:
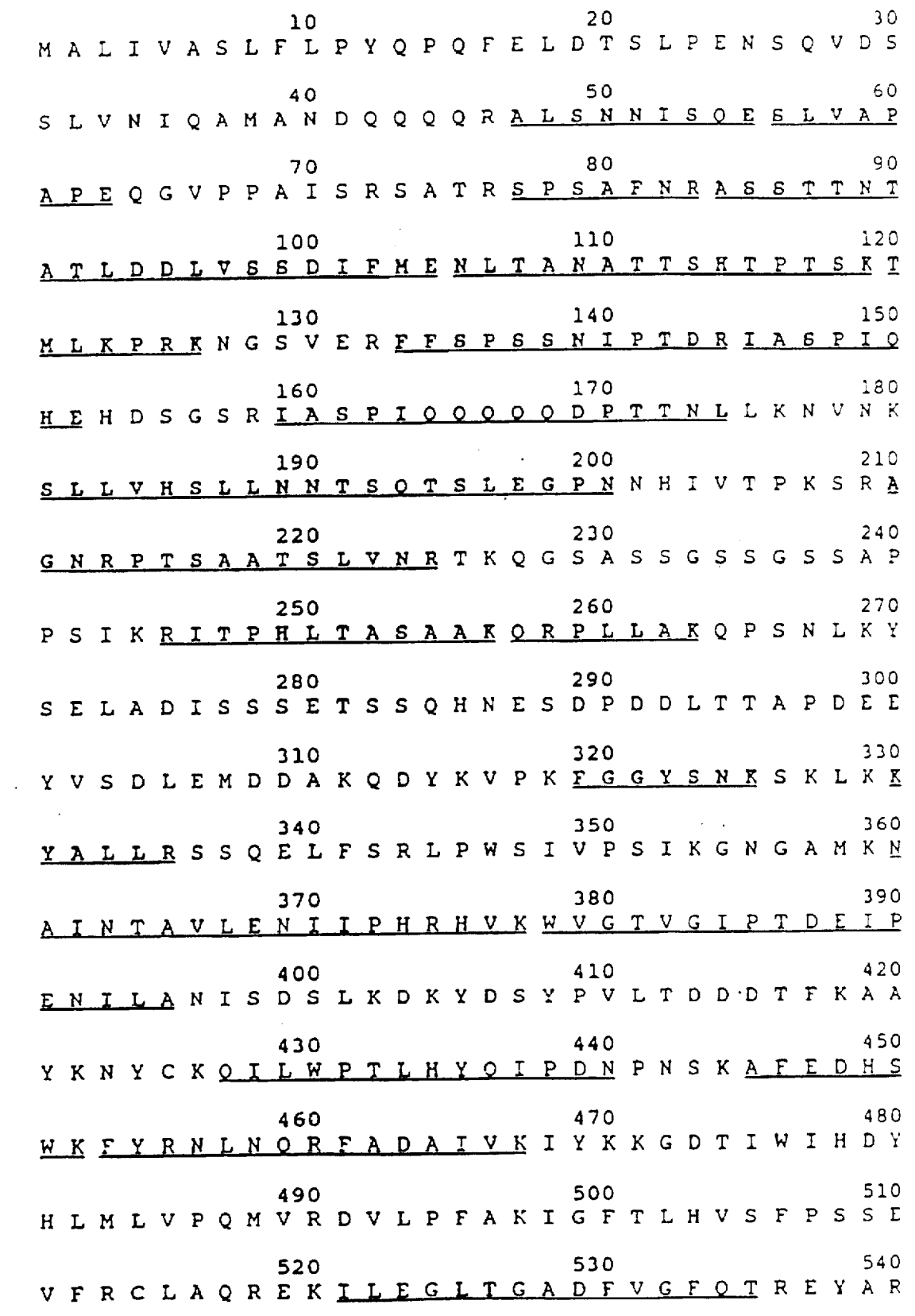
Figure 4C:
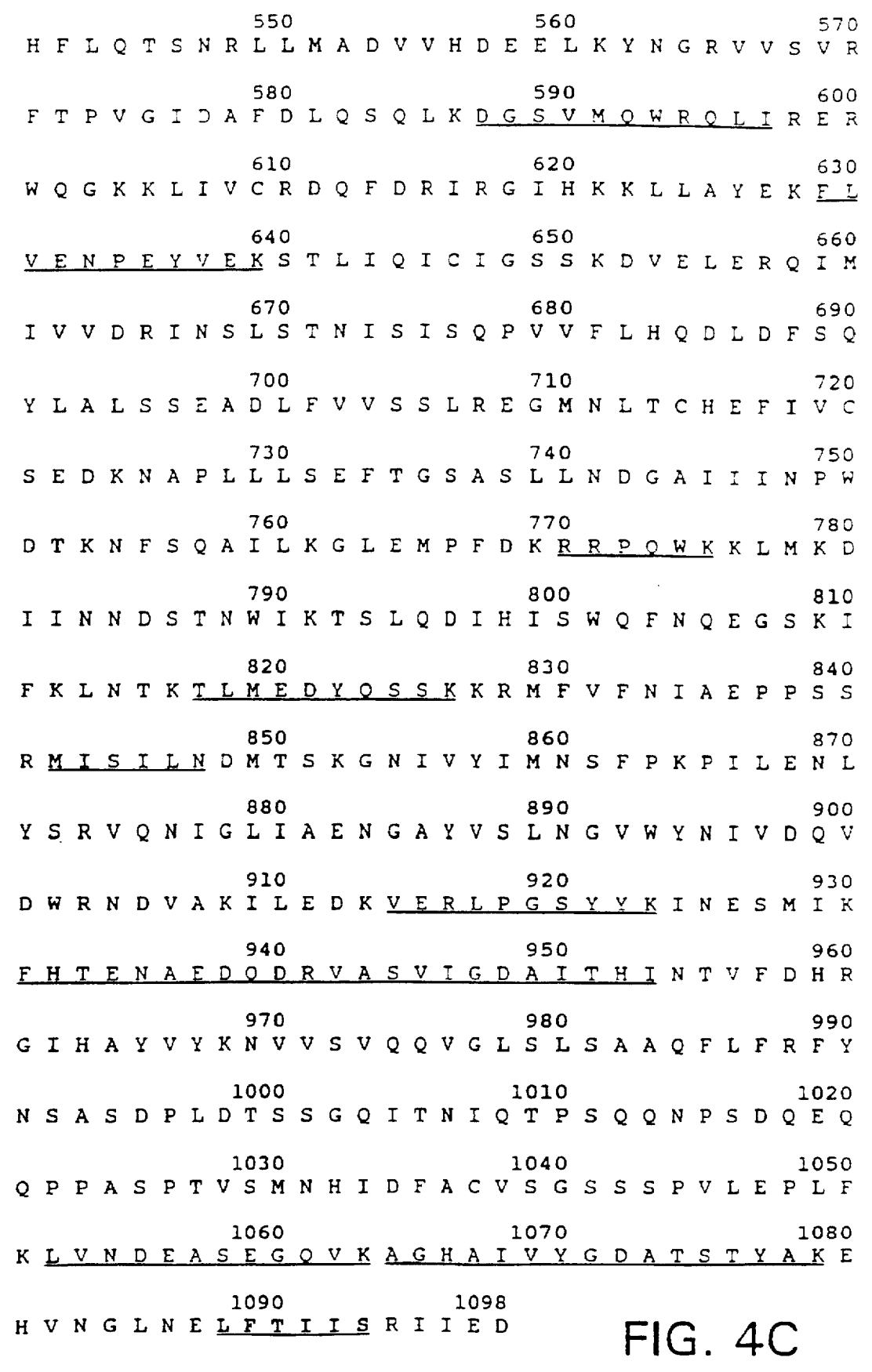

FIG. 4. The promoter and terminator regions of TSL1 and the amino acid sequence deduced from its ORF.

(a) In the promoter region, the start ATG codon is bold and underlined and two TATA boxes and six putative heat shock elements are underlined. A putative MIG1 binding site is overlined. In the terminator region, the TAA stop codon is bold and underlined and a putative transcription termination element is underlined. Lower case letters show the end of the terminator region of the ARGRII gene, which has opposite polarity. (b) In the amino acid sequence (SEQ ID NO:82), sequences found in peptides isolated from (fragments of) the 123 kDa long chain are underlined, and those from peptides liberated from intact trehalose synthase by limited digestion with trypsin are underlined and bold.

Figure 5A:
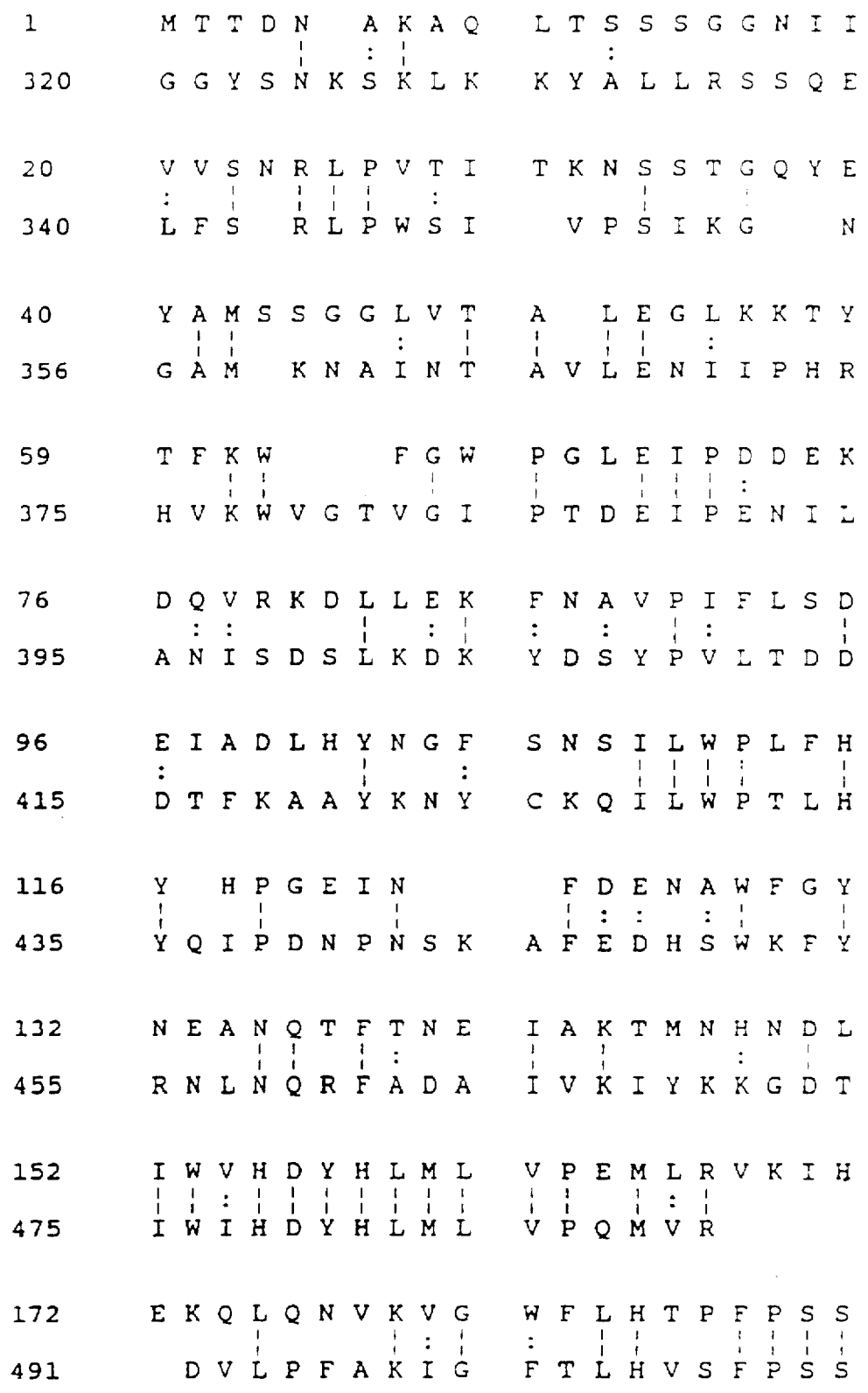
Figure 5B:
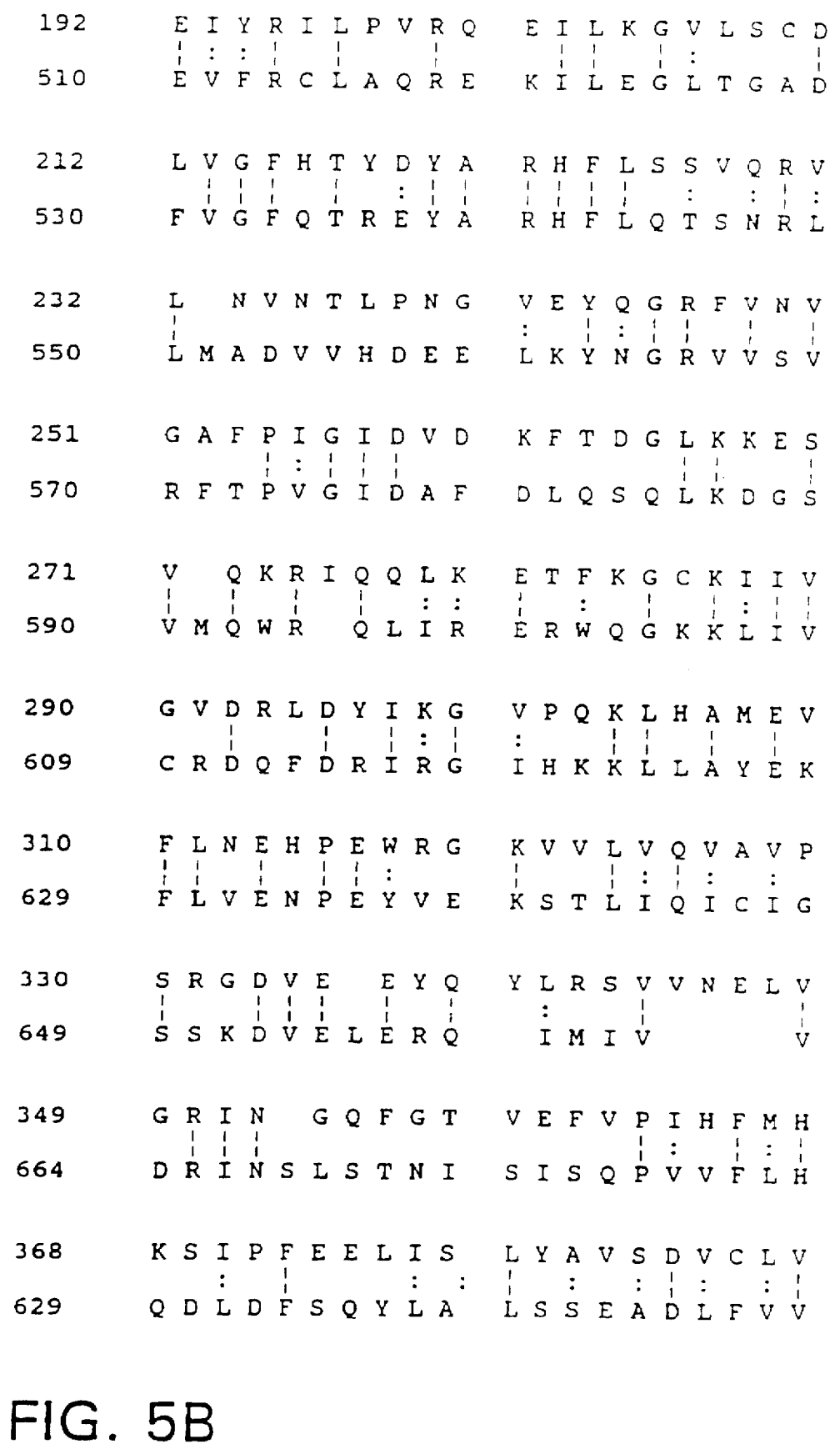
Figure 5C:
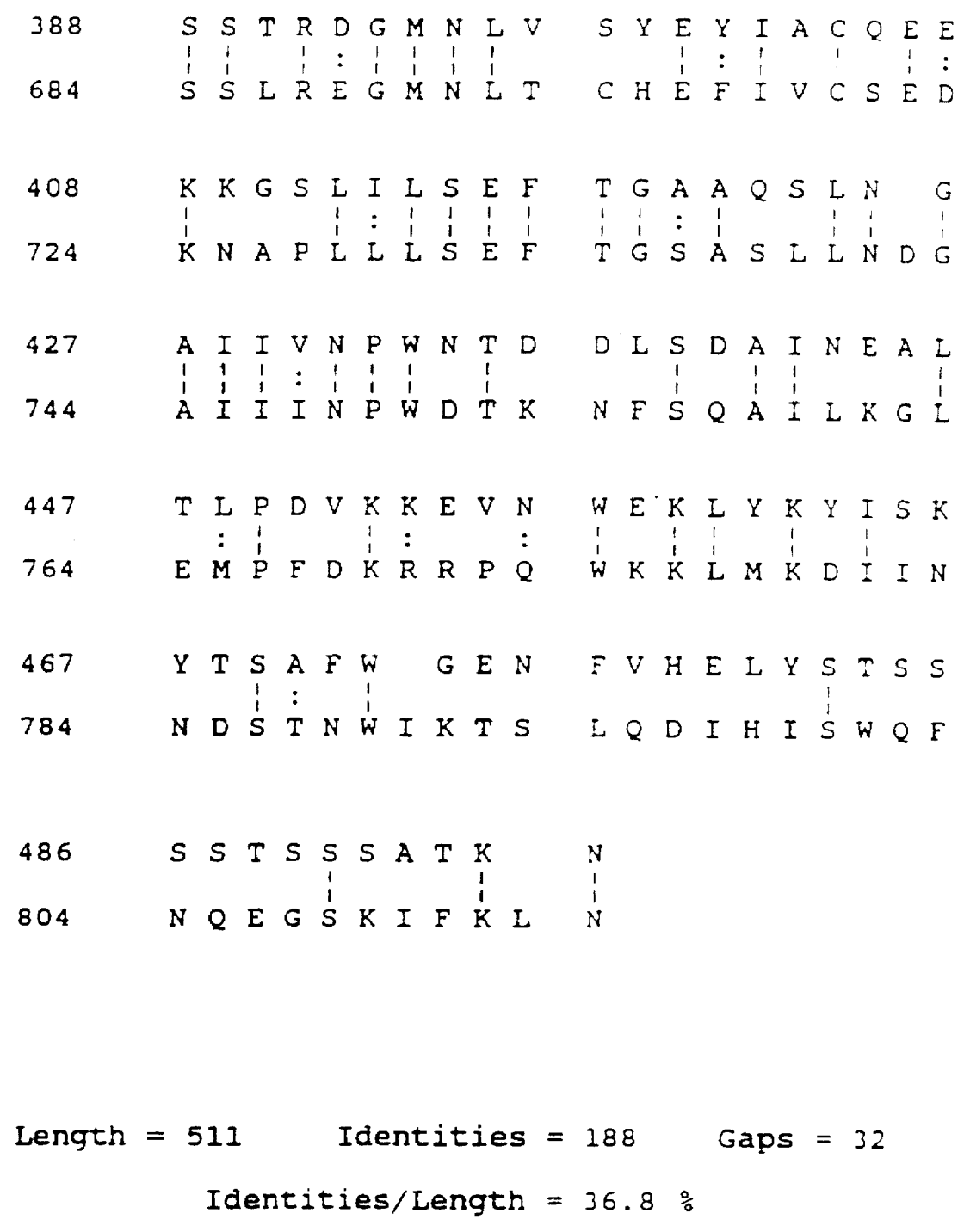

FIG. 5. Alignment of the amino acid sequences of the short and long chains of trehalose synthase The complete short chain sequence (SEQ ID NO:2; the upper sequence) is aligned against residues 320 to 814 of the 123 kDa long chain (SEQ ID NO:4; the lower sequence). 32 gaps are introduced to optimize the alignment. Vertical dashes indicate identical residues. Colons indicate conservative substitutions.

FIG. 6. Important restriction sites in TPS1 and TSL1

The heavy lines indicate open reading frames. The scale bar shows one kb.

FIG. 7. Synthesis of [$^{14}$C]-trehalose from [U-$^{14}$C]-glucose 6-phosphate by an extract of wild-type yeast Reaction mixtures (100 µl) contained 40 mM HEPES/KOH pH 6.8, 1 mg BSA/ml, 10 mM MgCl$_2$, 10 mM [U-$^{14}$C]-G6P (736 c.p.m./nmol) and (a) no phosphate or (b) 5 mM K phosphate pH 6.8 and (0) 5 mM UDPG, (●) 2.5 mM ADPG or (□) neither UDPG nor ADPG. Reactions were started by adding 10 µl (equivalent to 94 µg fresh yeast) of a 28.000 g supernatant of stationary phase X2180. Reactions were stopped by transfer to boiling water for 2 min and addition of 1.0 ml of a slurry of AG1-X8 (formate) anion exchange resin [Londesborough & Vuorio (1991) loc. cit.]. The radioactivity in the resin supernatant was measured.

Figure 8:
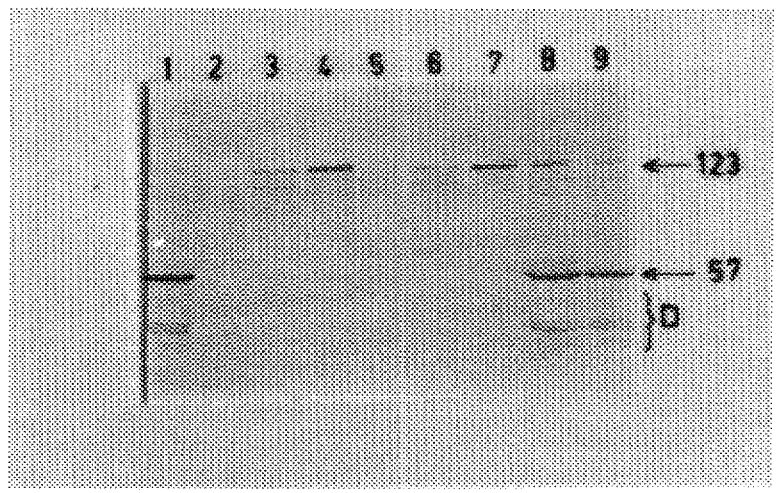

FIG. 8. Western analysis of Klg 102 and X2180 yeasts

Growth of the yeasts is described in Example 7. The loads of fresh yeast per lane were: lane 1, 200 μg X2180/2; lanes 2 and 5, 330 μg 2669/1; lanes 3 and 6, 610 μg 2669/2; lanes 4 and 7, 810 μg 2670/1+2; lane 8, 560 μg X2180/1 and lane 9, 280 μg X2180/1. The blot was probed with anti-TPS/P serum at a dilution of 1/30,000. Major bands of trehalose synthase are identified on the right.

Figure 9:
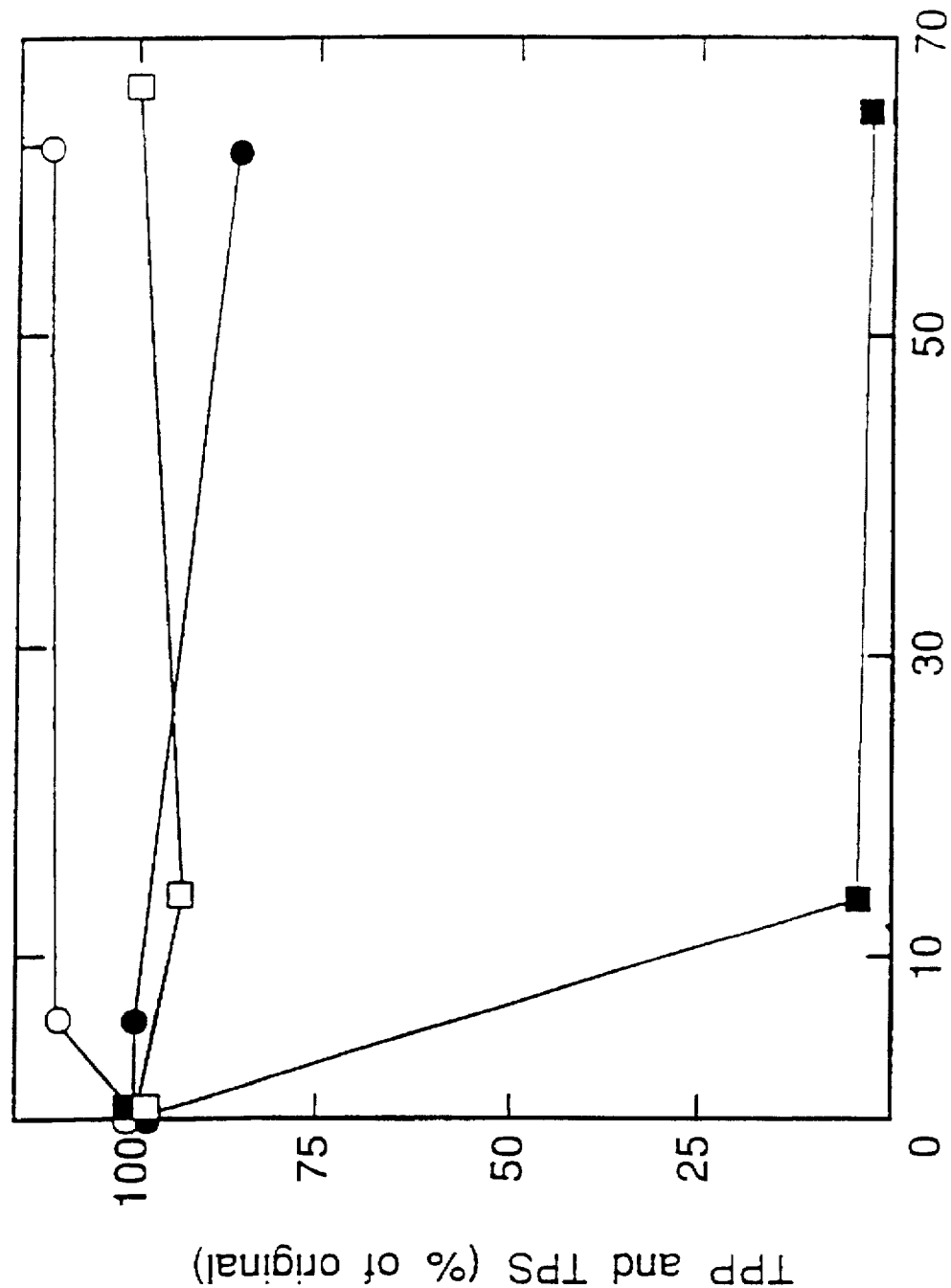

FIG. 9. Treatment of truncated trehalose synthase with 1.9 mM NEM

Truncated enzyme (0.13 Tre6P synthase units/ml≈43 μg/ml) in 2 mg BSA/ml 50 mM HEPES pH 7.0 containing 67 mM NaCl, 0.2 mM EDTA, 0.17 mM dithiothreitol, 0.17 mM benzamidine and 1.7 mM UDPG was incubated at 24° C. with (closed symbols) or without (open symbols) 1.9 mM NEM. Tre6P synthase (●○) and Tre6Pase (■,□) activities were measured.

Figure 10:
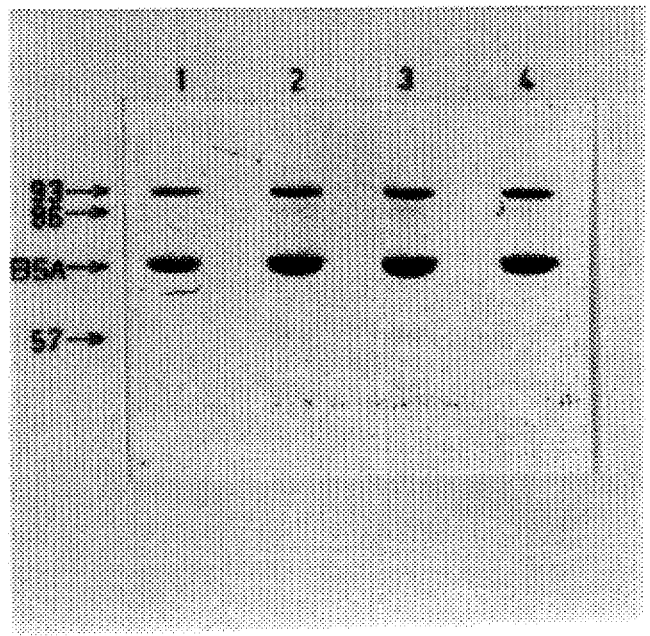

FIG. 10. Autoradiogram of truncated trehalose synthase labelled with [$^{14}$C]-NEM and separated by SDS-PAGE Labelling was performed as described in Example 8 for 1.5, 10.5, 63 and 190 min in lanes 1, 2, 3 and 4, respectively. The positions of the (57 kDa) short chain, 93 and 86 kDa long chain fragments and the carrier BSA are indicated.

Figure 11:
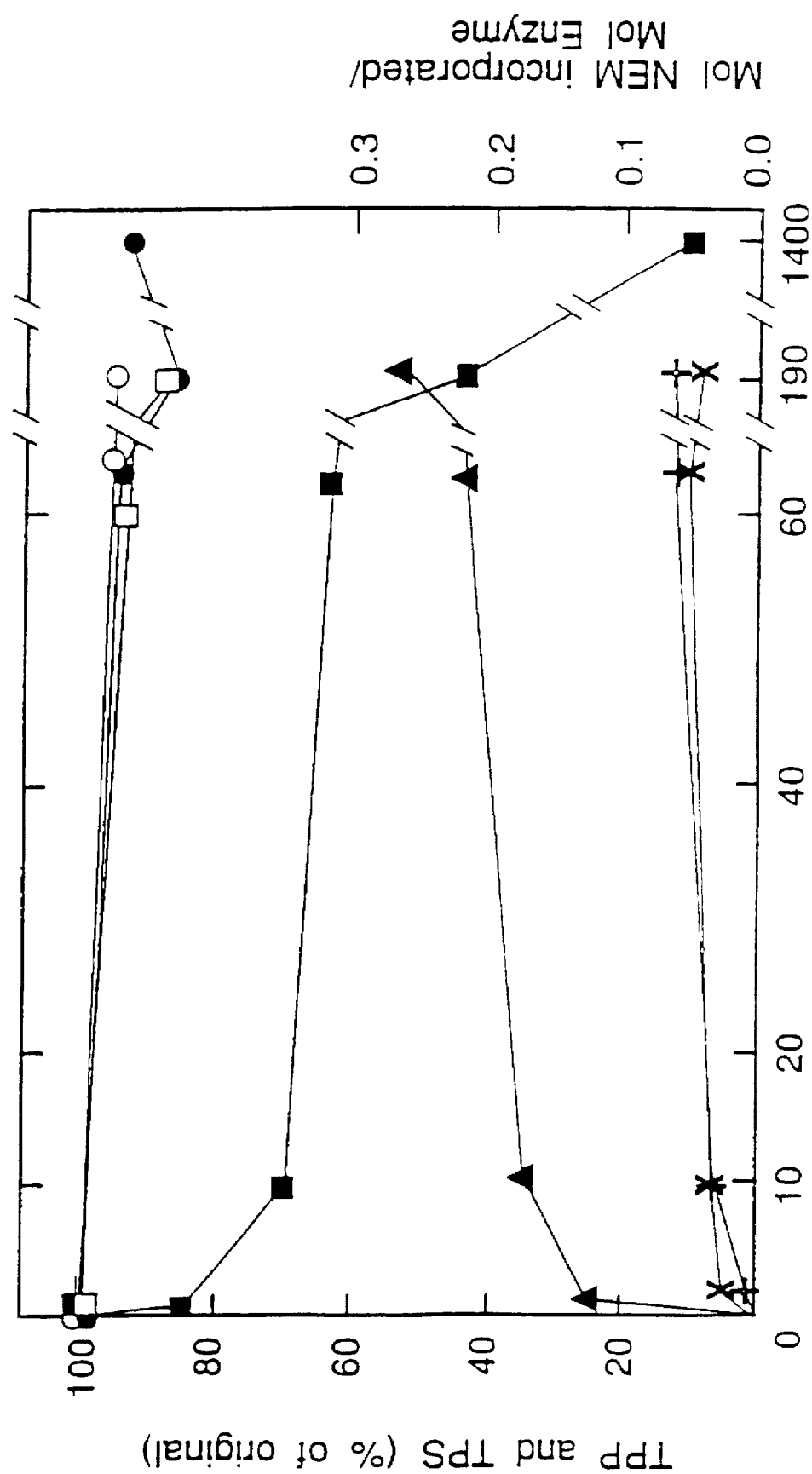

FIG. 11. Treatment of truncated trehalose synthase with ethyl-labelled NEM.

Truncated enzyme (7.2 Tre6P synthase units/ml≈0.24 mg/ml) in 1 mg BSA/ml 25 mM HEPES pH 7.0 containing 2 mM MgC12, 1 mM EDTA and 0.2M NaCl was incubated at 23° C. with (solid symbols) or without (open symbols) 32 μM ethyl-labelled NEM. Tre6P synthase (●,○) and Tre6Pase (■,□) activities and the amounts of [$^{14}$C]-NEM incorporated into the 93 (▲), 86 (+) and 57 (X) kDa polypeptides were measured. 0.1 mol NEM incorporated per mol (150 Kg) of enzyme corresponds to an excess radioactivity of 75 c.p.m. in bands cut from the gel.

Figure 12:
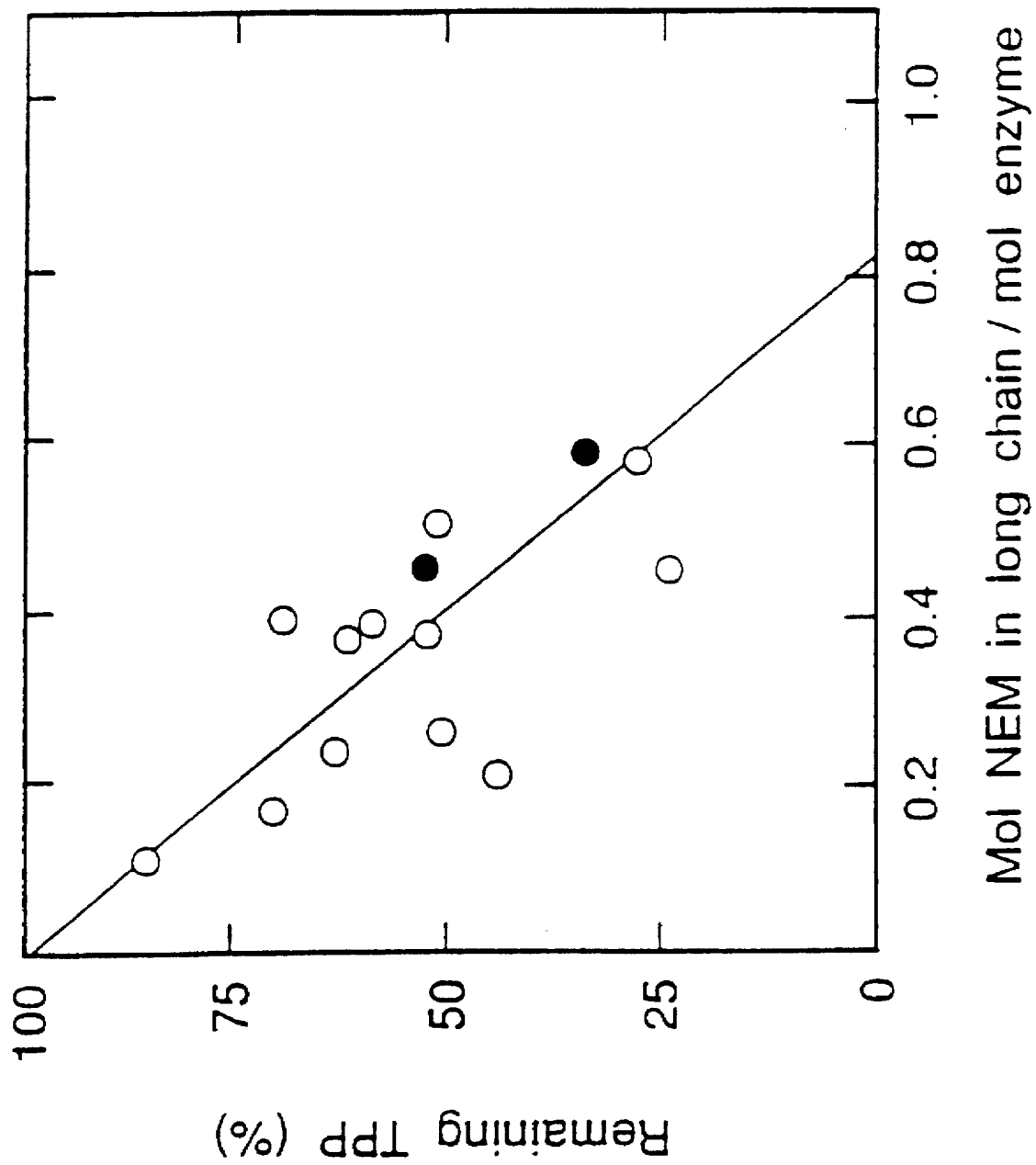

FIG. 12. Stoichiometry of NEM labelling

Residual Tre6Pase activity is plotted against the amount of NEM incorporated to the 93 and 86 kDa fragments of the long chain. Ring-labelled (●) and ethyl-labelled (○) NEM were used.

Figure 13:
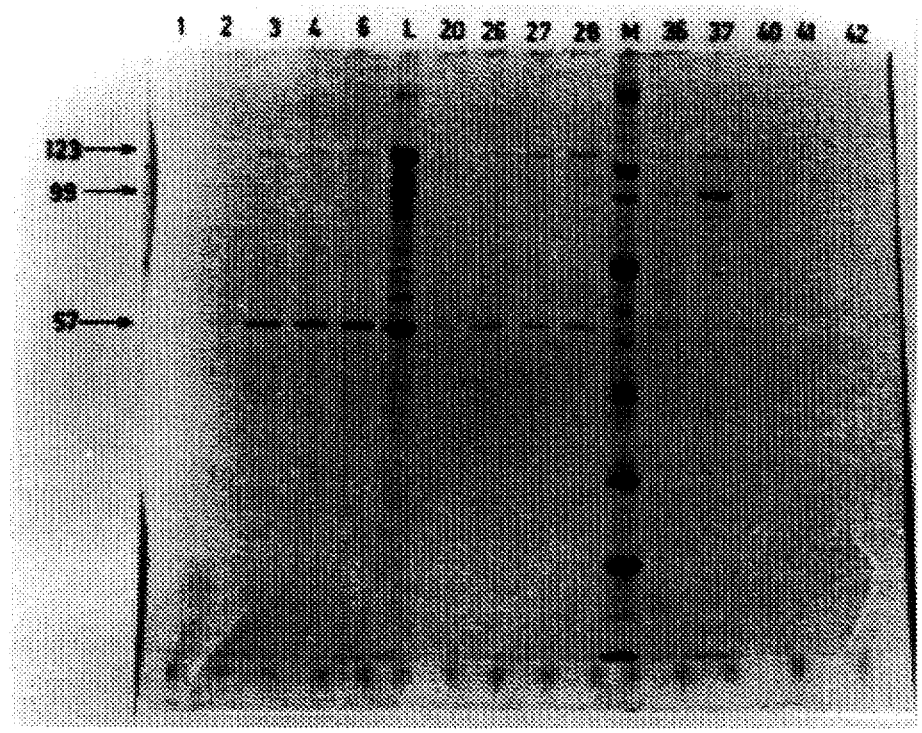

FIG. 13. SDS-PAGE analysis of fractions eluted from the cellulose-phosphate with buffer containing 0.3% Triton Lane L contains 47 μl of the intact trehalose synthase applied to the column. Lane M contains about 1 μg each of the molecular mass markers used in FIG. 1. The numbered lanes contain 33 μl of selected 1.5 ml fractions eluted from the column. The NaCl gradient began to appear in fraction 6 and reached 300 mM at fraction 27. A step to 600 mM NaCl emerged between fractions 36 and 37. Fractions 40 to 42 were eluted with 200 mM K phosphate. The major bands in the trehalose synthase preparation are identified on the left. Details are given in Example 9.

Figure 14:
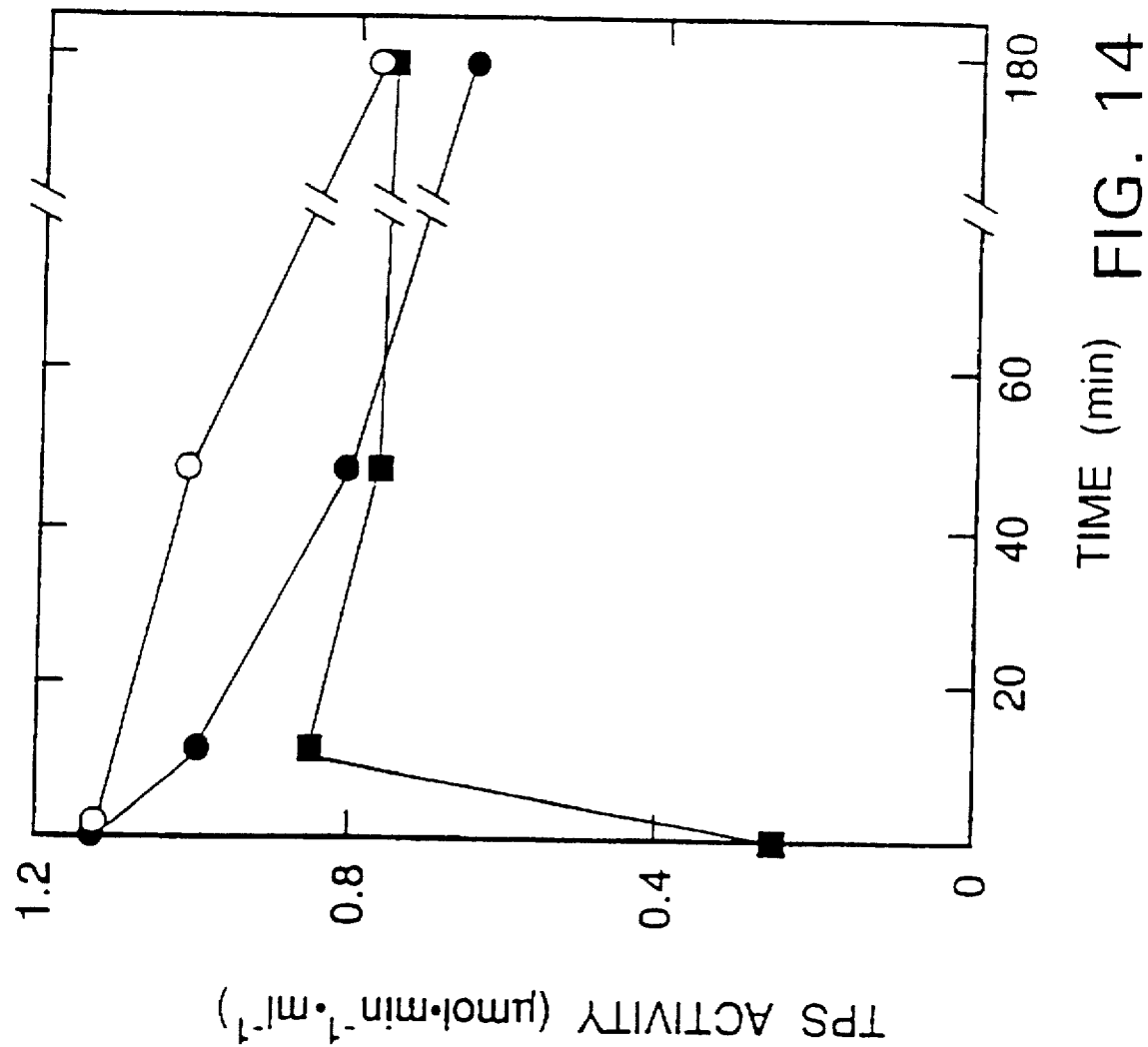

FIG. 14. In vitro activation of trehalose synthase by limited tryptic digestion

Intact trehalose synthase was incubated with (solid symbols) and without (open symbols) trypsin and its Tre6P synthase activity measured in the presence of 5 mM F6P in reaction mixtures containing (○,●) no phosphate or (■) 5 mM K phosphate pH 6.8. Details are given in Example 10.

Figure 15:
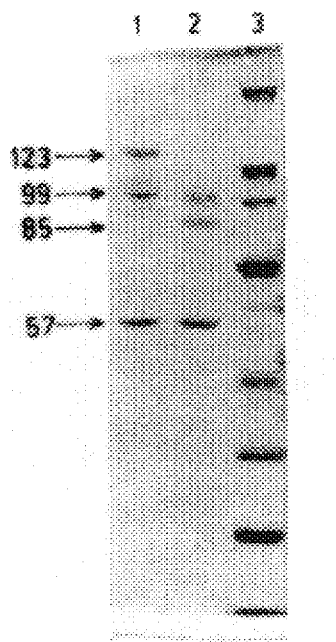

FIG. 15. Limited try-tic digestion of intact trehalose synthase

Lane 1 contains the untreated trehalose synthase used in FIG. 15 and lane 2 the same amount of enzyme after 48 min treatment with trypsin. Lane 3 contains molecular mass standards. The major polypeptides of trehalose synthase are identified on the left.

Figure 16:
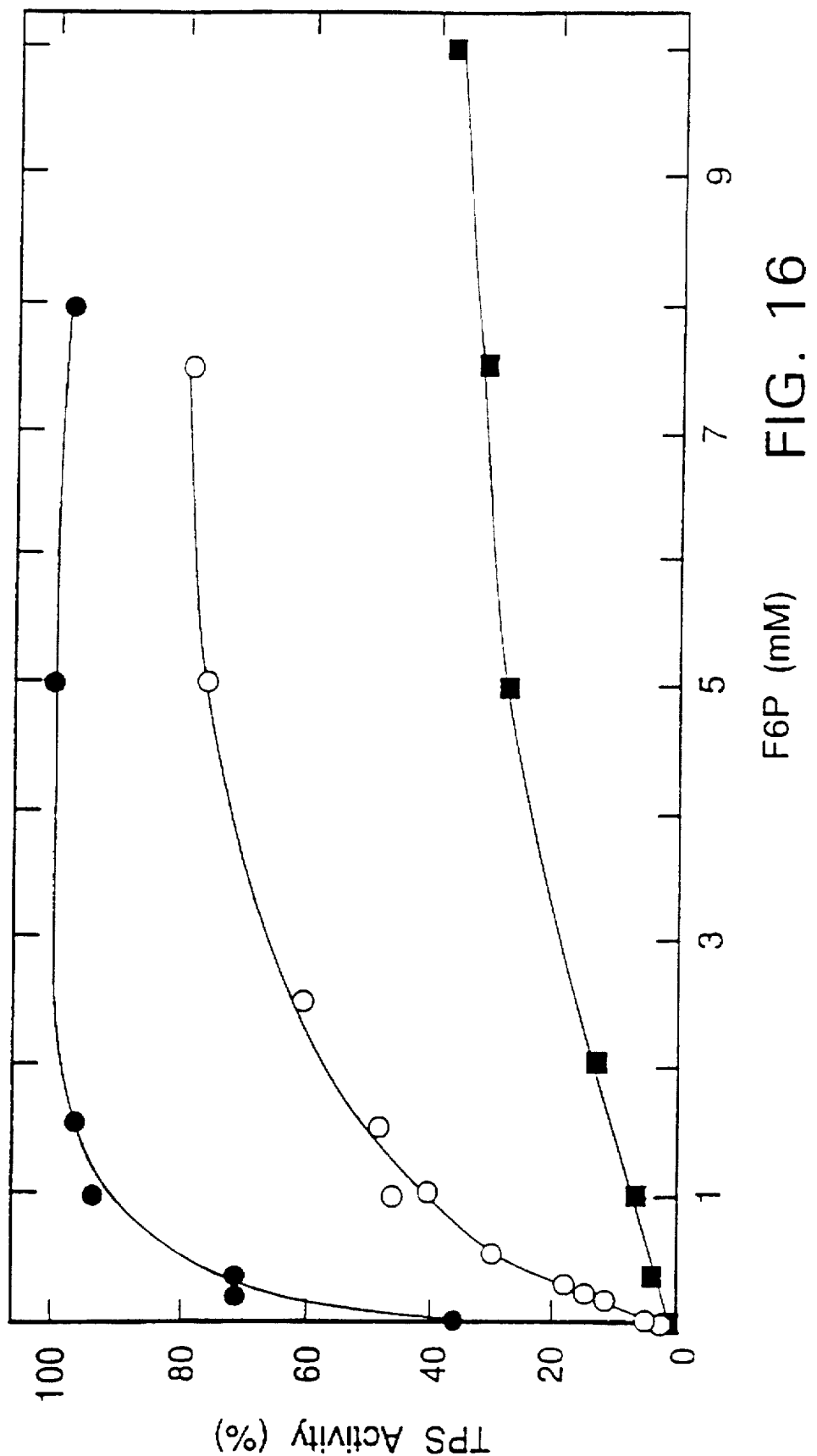

FIG. 16. The effect of fructose 6-phosphate on the Tre6P synthase activity of intact trehalose synthase at different phosphate concentrations The Tre6P synthase activity of native trehalose synthase was measured between zero and 10 mM F6P. Other conditions were as in the standard Tre6P synthase assay with (●) no changes, (○) 1.3 mM K phosphate pH 6.8 added or (■) 4 mM K phosphate pH 6.8 and 0.1M KCl added and the MgCl$_2$ concentration decreased to 2.5 mM. Activities are shown as percentages of that in the standard assay (i.e., at 5 mM F6P and no phosphate).

Figure 17:
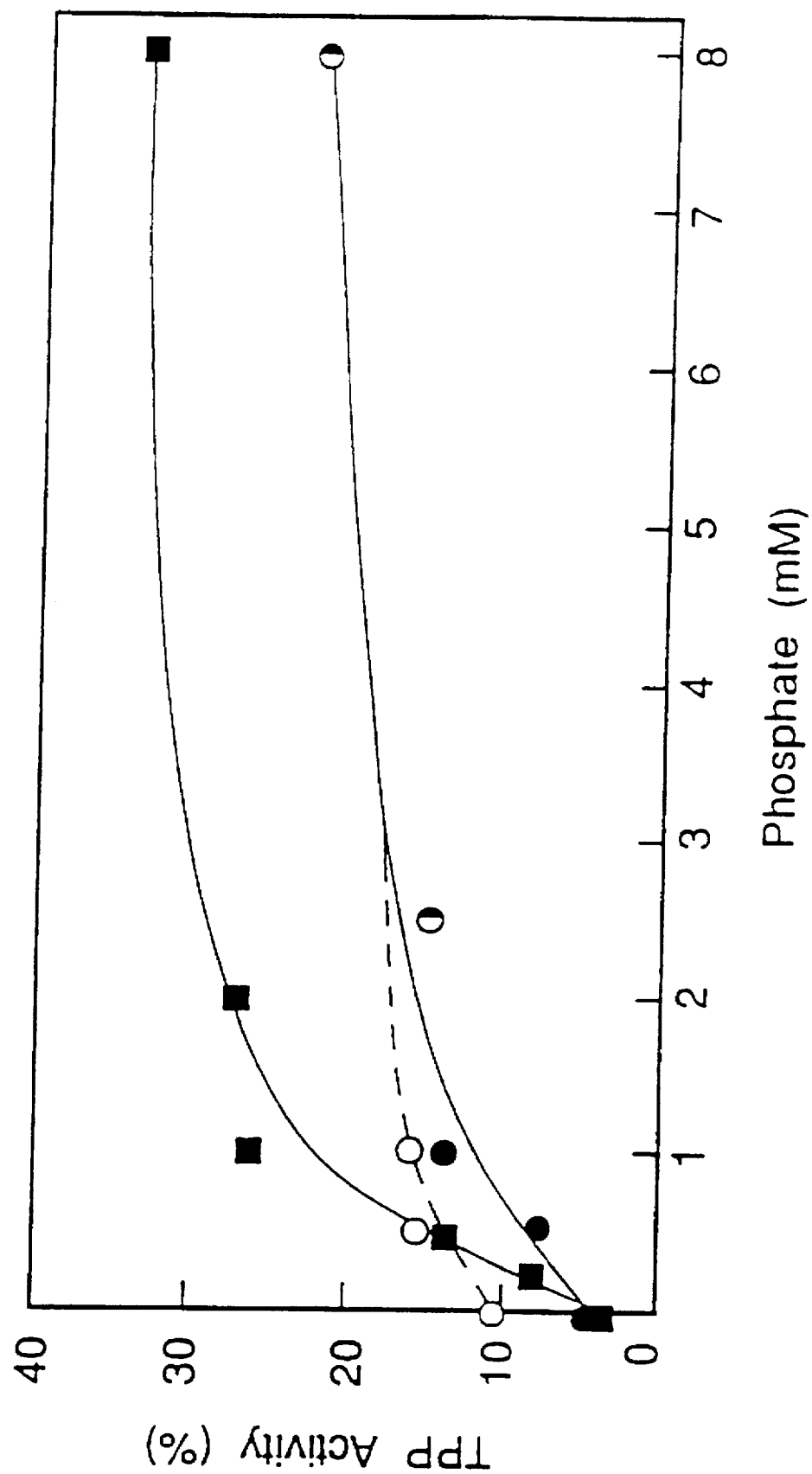

FIG. 17. Activation of the Tre6Pase activities of intact and truncated trehalose synthase by phosphate Tre6Pase activities were measured at 0.5 mM [$^{14}$C]-trehalose-6-phosphate in assay mixtures containing 50 mM Hepes pH 6.8, 1 mg bovine albumin/ml and the indicated concentrations of K phosphate pH 6.8 and are shown as percentages of the standard Tre6P synthase activity. Initial rates are shown for the (■) intact and (●) truncated enzyme. Rates during the second five minutes of the accelerating reaction obtained with truncated enzyme are also shown (○).

Figure 18:
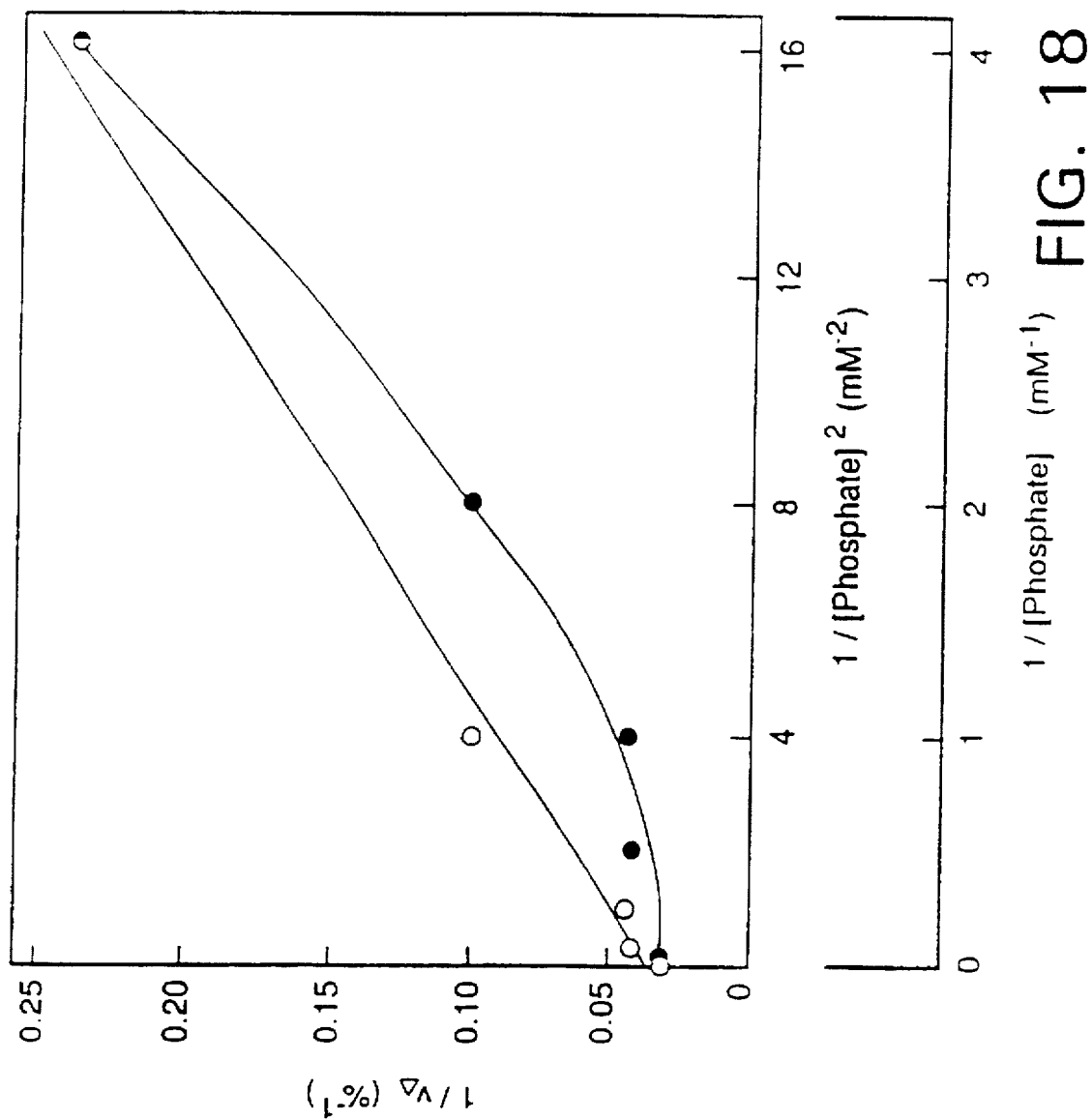

FIG. 18. Phosphate-dependence of the Tre6Pase activity of intact trehalose synthase The reciprocal of the increase in rate ($V_A$) caused by the phosphate is plotted against (○) [phosphate]$^{-2}$ or (●) [phosphate]$^{-1}$. $V_A$ is shown as a percentage of the standard Tre6P synthase activity.

Figure 19A:
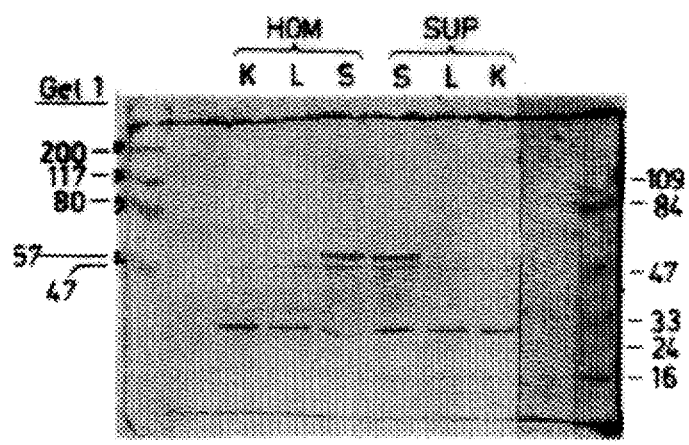
Figure 19B:
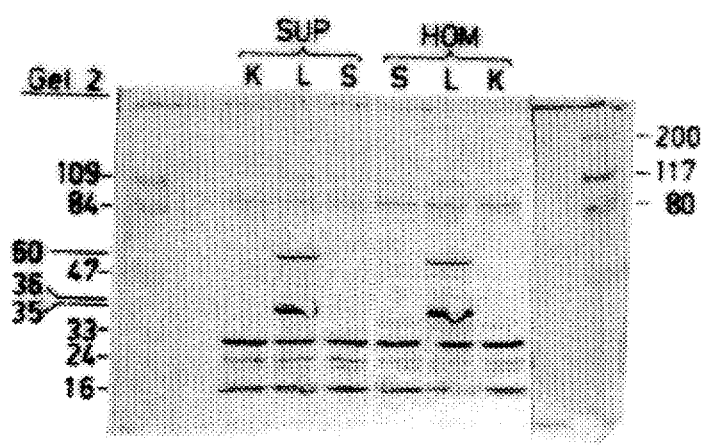

FIG. 19. Western analyses of E. coli transformed with TPS1 and TSL1

The gels were loaded with samples of whole homogenates (HOM) equivalent to 300±12 μg fresh cells or 28 000 g supernatants (SUP) equivalent to 340±25 μg fresh cells. The letters above the lanes indicate the cell types: K, control (HB101) cells; L, ALKO3568 (HB101 transformed with TSL1); S, ALKO3566 (HB101 transformed with TPS1). Gel 1 was probed with anti-57K serum (1/20 000) and gel 2 with anti-93K serum (1/20 000). The positions of the 57 kDa short chain and about 60, 36 and 35 kDa fragments of the 123 kDa long chain are shown. Molecular mass standards are labelled in kDas.

FIG. 20. Some plasmids containing TPS1 and TSL1 pBluescript containing (a) TPS1 with its own promoter, (b) TPS1 without its promoter and (c) TSL1 with its own promoter are shown.

Figure 21:
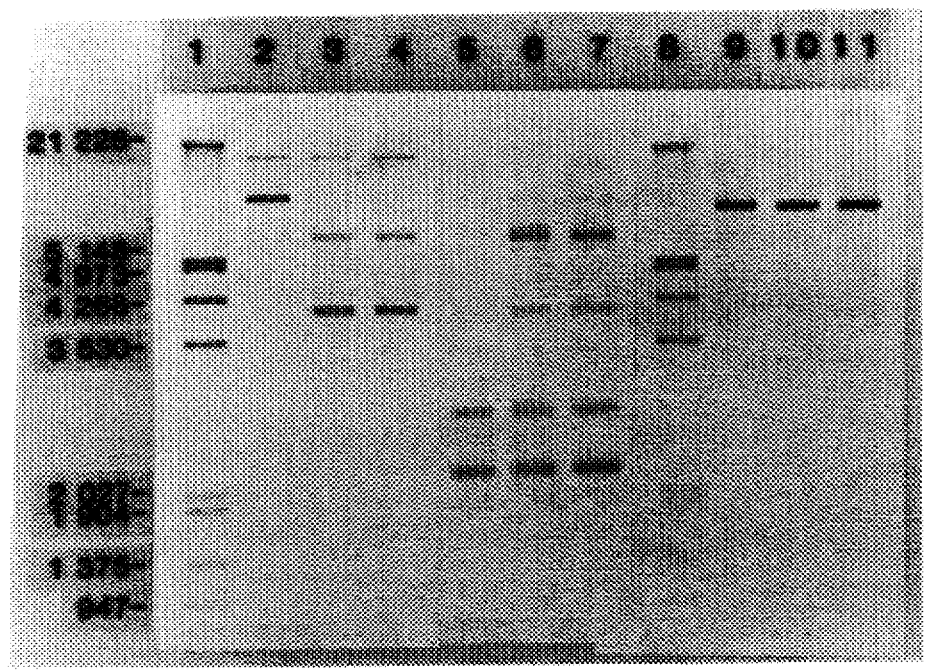

FIG. 21. Southern analysis of two tps1 disruptants of S.cerevisiae.

ClaI digests of DNA from control yeast (S150-2B; lanes 2,5 and 9), and two tps1 disruptants, ALKO 3569 (lanes 3, 6 and 10) and ALKO 3570 (lanes 4,7 and 11) were probed with TPS1 (lanes 2 to 4), LEU2 (lanes 5 to 7) and TSL1 (lanes 9 to 11). Lanes 1 and 8 contain DNA standards FIG. 22. Increased temperature tolerance of a pALK732 transformant The yeast strain S150 (○) and its transformant (●) with pALK732 containing the coding sequences of TPS1 and TSL2 under the control of ADC1 promoters were grown on minimal media with 2% glucose and all essential amino acids (S150) or lacking leucine (the transformant). At an initial $A_{600}$ of 0.27, 5 ml portions were placed in screw-capped tubes in the slots of a temperature gradient block. After 28 h the tubes were vigorously mixed and their $A_{600}$ determined.

Figure 23:
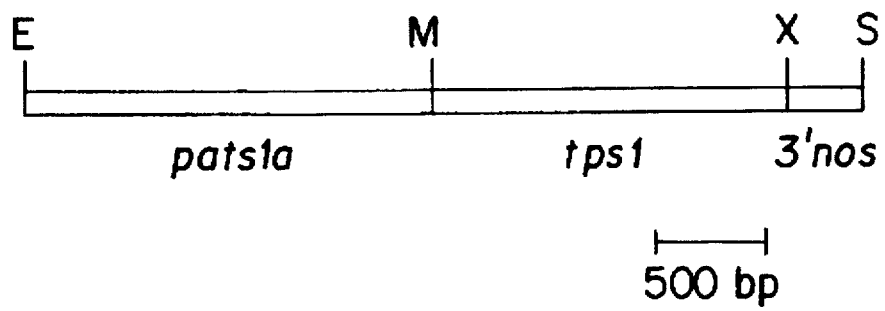

FIG. 23. The chimeric pATS1a/TPS1 construct used to transform tobacco.

The figure depicts the schematic structure of the chimeric gene construct containing the *A. thaliana* Rubisco small subunit promoter (pATS1a) fused to the yeast TPS1 gene encoding the Tre6P synthase subunit and the transcription stop signal from the nopaline synthase gene of *Agrobacterium tumefaciens* (nos). Only the part of the plasmid pKOH51 with the chimeric gene is shown. Unique restriction enzyme cleavage sites for the chimeric gene construction are shown.

Figure 24:
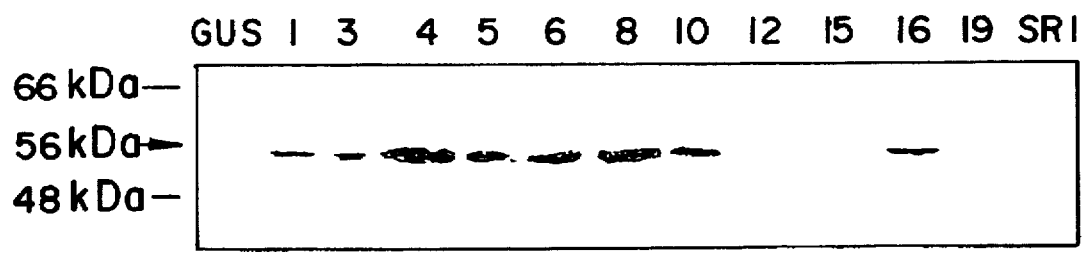
Figure 25A:
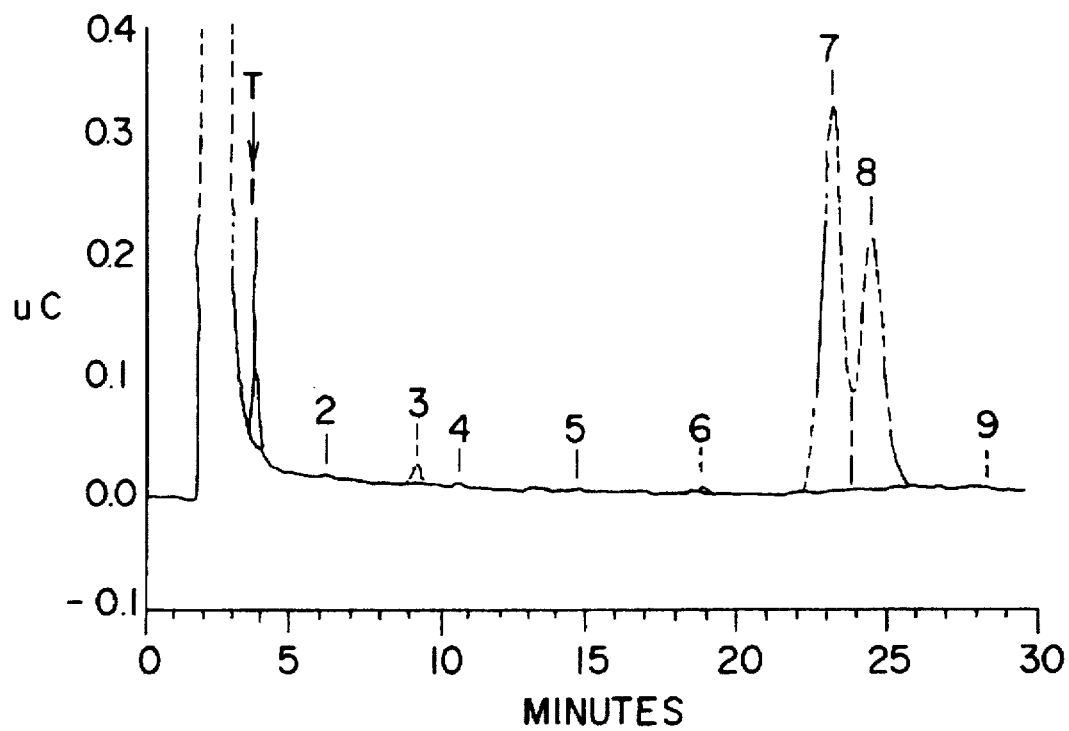
Figure 25B:
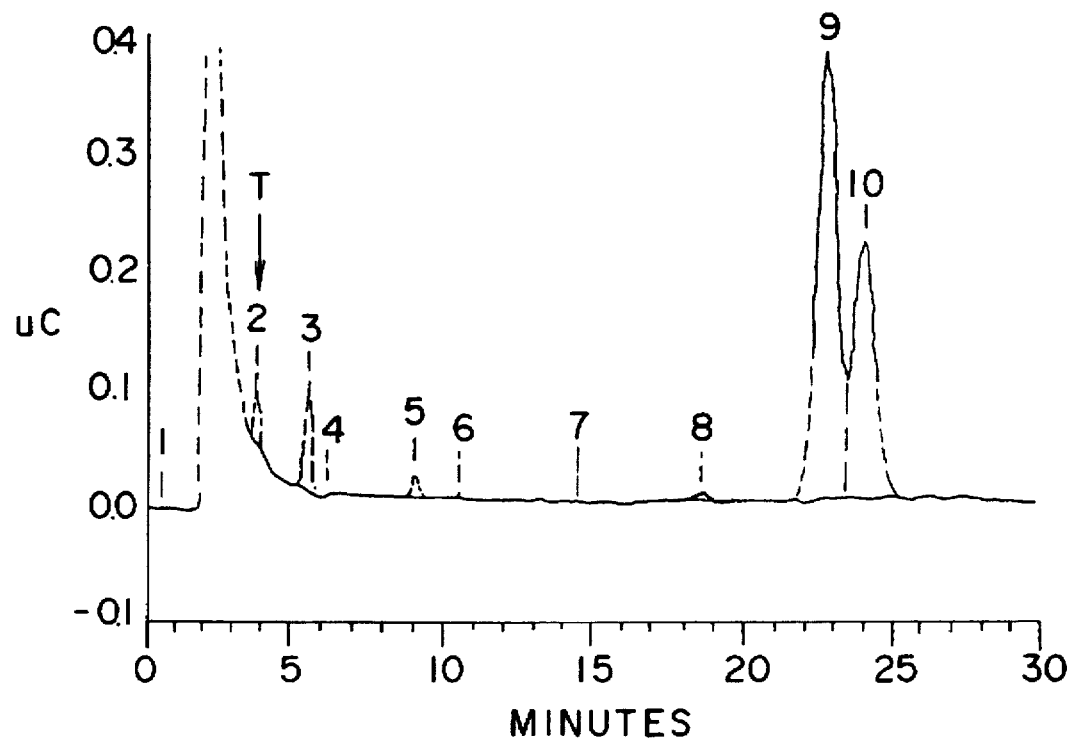
Figure 25C:
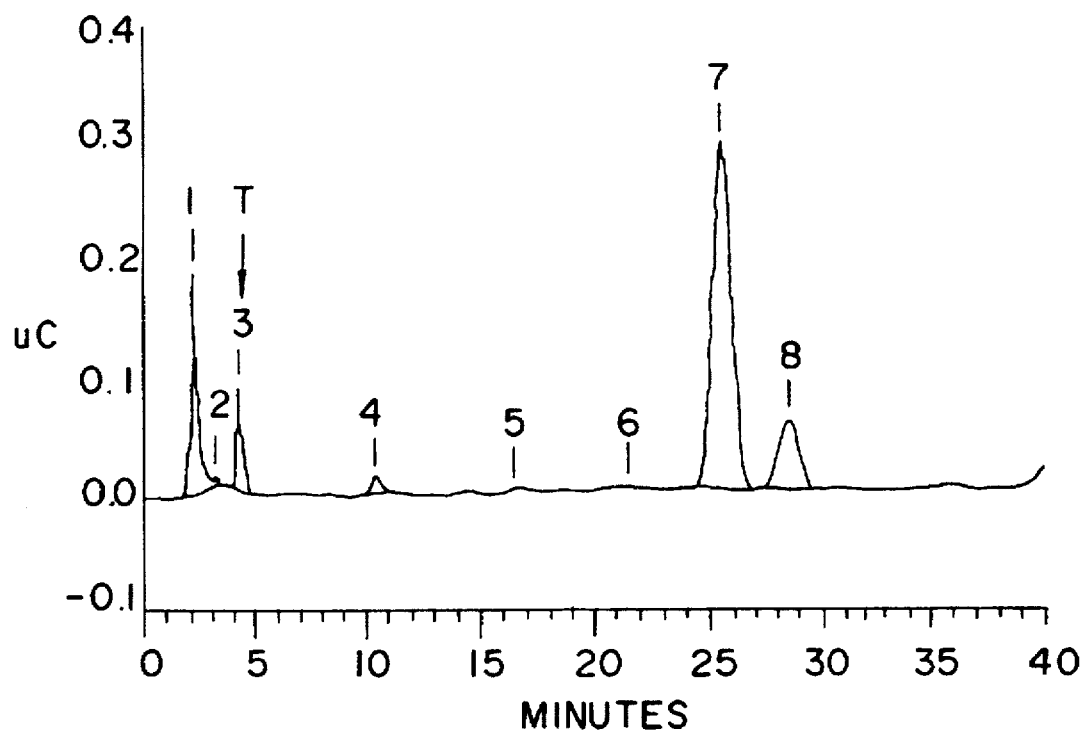
Figure 25D:
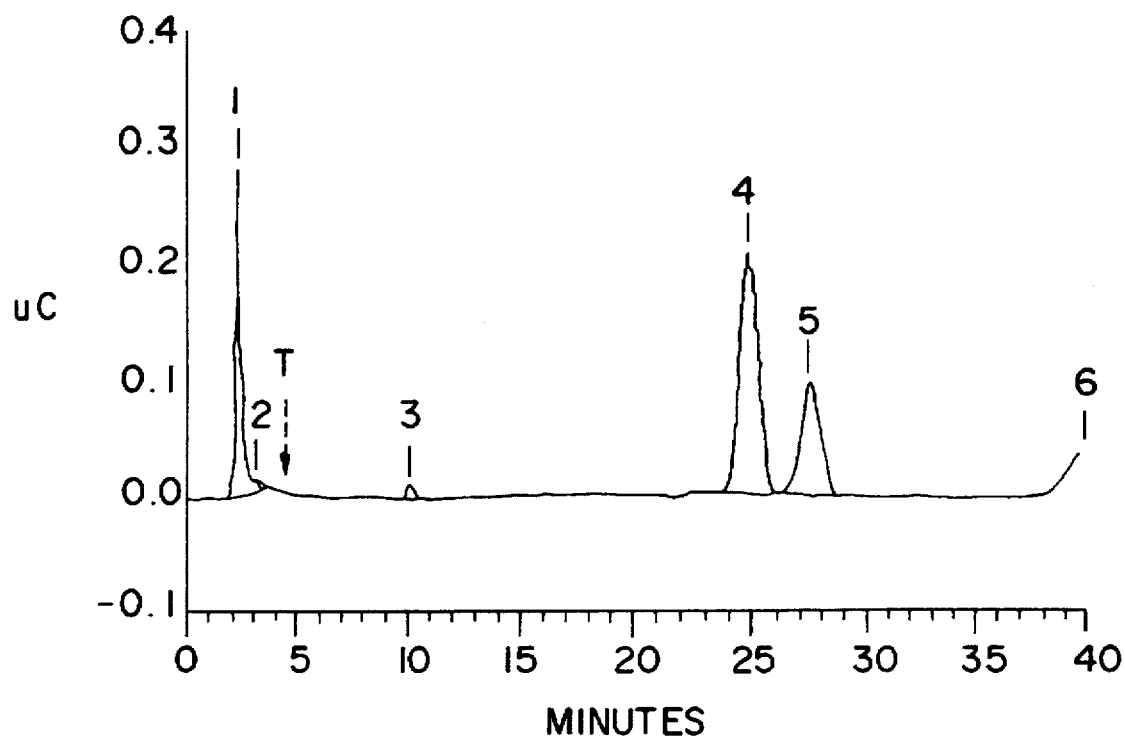

FIG. 24. Western blot analysis of transgenic tobacco plants.

The 56 kDa TPS1 product is indicated by an arrow. Proteins were extracted from the transformed tobacco plants containing (1, 3, 4, 5, 6, 8, 10, 12, 15, 16 and 19) the construct described in FIG. 23, or (GUS) another chimeric gene with the Cauliflower mosaic virus 35S promoter fused to the β-glucuronidase gene (UIDA) in the same vector or (SR1) from untransformed tobacco plants. Equal amounts of protein were loaded in each lane. The antiserum used (anti-57K) was raised against the 56 kDa Tre6P synthase subunit from yeast.

FIG. 25. Chromatographic identification of trehalose.

Samples (20 µl) of water extracts of tobacco leaves were analyzed by HPLC as described in General Materials and Methods. Extracts A and B contained 192 mg of greenhouse-grown Transformant 19 ml$^{-1}$ (A) before and (B) after treatment with trehalase. Extracts C and D contained 149 mg leaf ml$^{-1}$ from (C) Transformant 4 or (D) a control plant transformed with plasmid pDE1001 lacking the TPS1 gene, both grown under sterile conditions. Trehalose peaks are indicated with T. The two large peaks at about 25 min (peaks 7 and 8 in A) are glucose and sucrose.

DETAILED DESCRIPTION OF THE INVENTION

In the following description, trehalose-6-phosphate synthase (Tre6P synthase) and trehalose-6-phosphate phosphatase (Tre6Pase) refer to catalytic activities, not to proteins, unless specifically stated otherwise, whereas trehalose synthase refers to a protein that can convert uridine diphosphoglucose (UDPG) and glucose-6-phosphate (G6P) into trehalose, and also exhibits as partial reactions Tre6P synthase and Tre6Pase activities. TPS1 (earlier called TSS1; the name has been changed in accordance with a 1993 initiative by Dr. Gancedo to standardize the names of this gene), TSL1, and TSL2 are structural genes that encode, respectively, the short (57 kDa) and the about 130 and 99 kDa long chains of trehalose synthase. It is well known that mutations occur in genes and can cause changes in the amino acid sequence of the encoded polypeptide. Changes can also be introduced by genetic engineering techniques. As used herein, the term TPS1 (or TSL1 or TSL2) gene includes all DNA sequences homologous with the sequences herein disclosed for TPS1 (or TSL1 or TSL2) and encoding polypeptides with the functional or structural properties of the 57 kDa (or about 130 kDa or 99 kDa, respectively) polypeptide. Sequences articially derived from these genes but still encoding polypeptides with the desired functional or structural properties are also included.

The present inventors previously reported the isolation of a partially degraded protein preparation that contained a short (57 kDa) polypeptide chain and two fragments (86 and 93 kDa) of a long polypeptide chain and possessed both Tre6P synthase and Tre6Pase catalytic activities [Londesborough, J & Vuorio, O. (1991) Journal of General Microbiology 137, 323–330]. The size of the full-length intact long chain, from which both the 86 and 93 kDa fragments were then believed to be derived, and whether one or other polypeptide possessed one or other of the catalytic activities were not known at that time.

The inventors have now isolated an undegraded trehalose synthase that contains the 57 kDa short chain, and two long chains of about 130 kDa and 99 kDa as its major polypeptides. Traces of other polypeptides are also present that appear to be degradation products of the about 130 and 99 kDa chains. Two genes, TPS1 and TSL1, that encode, respectively, the short and about 130 kDa long chains have been cloned and sequenced. Because the size of this long chain is now known from its gene to be 123 kDa, it is hereafter called the 123 kDa long chain. TPS1 encodes a polypeptide with a theoretical molecular weight of 56.2 kDa; however, this short chain and the 99 kDa long chain are still called after their apparent molecular weights by SDS-PAGE analysis, the error in such analyses being at least ±10 kDa at 130 kDa.

The sequences of TPS1 and the polypeptide it encodes are disclosed as SEQ ID NOS:1 and 2, respectively. The sequences of TSL1 and the polypeptide it encodes are disclosed as SEQ ID NOS:83 and 82, respectively (earlier versions of these sequences, lacking the 5'- and N-terminal regions, are listed as SEQ ID NOS:3 and 4). Genetic evidence is disclosed that shows that a functional TPS1 gene is involved in the expression of both Tre6P synthase and Tre6Pase catalytic activities in *S. cerevisiae*: (1) both activities are absent from a mutant strain (Klg 102) that lacks a properly functional TPS1 gene and does not express the short chain in a form recognizable in Western blots although it does express immunologically recognisable long chain; (2) disruption of TPS1 eliminates Tre6P synthase and Tre6Pase activities, abolishes the short chain signal from Western blots and prevents the accumulation of trehalose, and these defects are simultaneously reversed by transformation with TPS1, which also increased the resistance of the cells to freezing stress; and (3) transformation of *Escherichia coli* with TPS1 causes a large increase in the Tre6P synthase activity of the transformants (but no detected increase in their Tre6Pase activity).

We disclose biochemical evidence that the Tre6Pase catalytic activity of a truncated trehalose synthase requires a functional long chain: incorporation of about 1 mole of $^{14}$C-N-ethylmaleimide into the 93 kDa long chain fragment per mole of truncated trehalose synthase results in complete loss of Tre6Pase activity but only a slight loss of Tre6P synthase activity. Furthermore, we have been able to isolate the 99 kDa polypeptide and show that it possesses residual Tre6Pase activity but no Tre6P synthase activity. Also, intact trehalose synthase is partially resolved into a 99 kDa-enriched form with a relatively high Tre6P phosphatase/synthase ratio and a 123 kDa-enriched form with a lower Tre6P phosphatase/synthase ratio. However, truncation of the 123 kDa long chain has dramatic and important effects on the Tre6P synthase activity of trehalose synthase: removal of the N-terminal 330 or so amino acids decreases the sensitivity of the Tre6P synthase catalytic activity to inhibition by phosphate and almost eliminates its activation by fructose-6-phosphate. Further, transformation of *E. coli* with TSL1 causes an increase in the Tre6P synthase activity of the transformants (but no detected increase in their Tre6Pase activity).

Thus, both the short and the long chains make essential contributions to both the Tre6P synthase and the Tre6Pase catalytic activities of trehalose synthase. The situation is therefore that there are at least two different structural genes for a trehalose synthase, neither of which can be completely described as the structural gene of either a trehalose-6-phosphate synthase protein or a trehalose-6-phosphate phosphatase protein.

We disclose that the amino acid sequences of peptides isolated from both the 86 and 93 kDa long chain fragments found in the truncated enzyme described by Londesborough & Vuorio [(1991) loc. cit] are encoded by TSL1. Surprisingly, however, none of the peptides isolated from the 99 kDa polypeptide in the intact enzyme is encoded by TSL1. Therefore, the structural genes encoding polypeptides of yeast trehalose synthase include a third member, TSL2. The 99 kDa polypeptide encoded by TSL2 was not visible in SDS-PAGE analyses of truncated enzyme. However, one of the 6 peptides isolated from the 93 kDa fragment was not encoded by TSL1 and had an amino acid sequence also found in a peptide isolated from the 99 kDa polypeptide. Thus, traces of a degradation product of the 99 kDa polypeptide are present in truncated enzyme, and migrate with the 93 kDa fragment during SDS-PAGE.

The inventors have not yet sequenced this third structural gene, TSL2, but disclose information that provides obvious methods for its isolation and cloning by a person ordinarily skilled in the art. Also a clone (pALK756) comprising at least part of this gene has been deposited (Accession number, DSM 7425; Deutsche Sammlung von Mikroorganismen und Zellkulturen, Mascheroder Weg 1 B, D-3300 Brauschweig)

We disclose that the genes TPS1 and TSL1 contain extensive similarities such that the amino acid sequence of the entire short chain is 37% identical to residues 495 to 814 of the long chain.

A novel feature of the present invention, therefore, is that in order to increase the capacity of a yeast or some other host organism for trehalose synthesis it can be necessary to increase the expression of the TPS1, TSL1 and TSL2 genes or modify these genes in some other way, not because either Tre6P synthase or Tre6Pase activity is "rate-limiting", but because more than one gene affects each activity. Thus, the results summarised above disclose that both TPS1 and TSL1 affect Tre6P synthase activity and both TPS1 and TSL2 affect Tre6Pase activity. However, these results also disclose that the TSL2 gene product (the 99 kDa polypeptide) isolated by chromatography is itself a trehalose-6-phosphatase whereas the TPS1 gene product expressed in *E. coli* or *Nicotiana tabacum* is a trehalose-6-phosphate synthase, although the catalytic efficiency of these separate polypeptides can be less than when they are correctly assembled in a trehalose synthase complex.

A surprising finding was that the TPS1 gene is identical with a gene variously called FDP1 or CIF1. This gene has pleiotropic effects on the utilization of sugars by *S. cerevisiae*. In particular, haploid yeast bearing certain alleles of this gene (the so-called fdp1 and cif1 mutants) are unable to grow on mannose, or on mannose or sucrose, or on mannose, sucrose or fructose, or on mannose, sucrose, fructose or glucose, depending upon the severity of the defect [Van de Poll & Schamhart, (1977) Molecular and general Genetics 154, 61–66; Bañuelos, M. & Fraenkel, D. G. (1982) Molecular and Cellular Biology 2, 921–929]. Such mutants grow normally on galactose. Therefore, during the selection of strains in which the TPS1 gene has been deleted or modified it is sometimes essential and always advisable to grow the transformants on galactose, because in many cases the desired transformant will be unable to grow on any other common sugar, including the routinely used glucose. This is an unexpected methodological consideration that would not be obvious even to a person skilled in the art: special knowledge about the sequence and chromosomal location of the TPS1 gene is required, which we now disclose.

Since our disclosure of the identity of TPS1 with FDP1 and CIF1 in U.S. Pat. No. 841,997, a confirmation has been published by Bell, W., et al. [(1992) European Journal of Biochemistry 209, 951–959)] The inventors' previous work [Londesborough & Vuorio (1991) loc. cit.] showed that the Tre6P synthase catalytic activity of what is now known to be trehalose synthase requires a so-called TPS-Activator protein, which is a dimer of 58 kDa subunits. We have identified this protein by the amino acid sequences of peptides it contains and by its catalytic activity and disclose that it is yeast phosphoglucoisomerase. We disclose that fructose-6-phosphate (F6P), which could be made by phosphoglucoisomerase from the glucose-6-phosphate (G6P) in the assay mixtures used to measure Tre6P synthase activity, is a powerful activator of the Tre6P synthase activity of intact trehalose synthase. Also, when the assay mixture contains an equilibrium mixture of G6P and F6P the TPS-Activator has no further effect, so that its phosphoglucoisomerase activity is a complete explanation of the activation it causes. Furthermore, the Tre6P synthase activity of truncated trehalose synthase does not require F6P, and is not so strongly inhibited by phosphate as is that of the native enzyme. Thus, a trehalose synthetic pathway can in principle be transferred to any organism by transforming the organism with the structural genes for yeast trehalose synthase: it is not necessary to simultaneously introduce the TPS-activator, because F6P is a ubiquitous component of cells. Furthermore, if the amounts of F6P in an organism are inadequate, or phosphate concentrations are too high, the organism can be transformed with a truncated version of TSL1 encoding the truncated long chain that confers insensitivity to phosphate and F6P. This aspect of the present invention is particularly significant, because it both allows the introduction of a trehalose synthetic pathway to organisms in which the cytosolic phosphate and F6P concentrations would prevent the efficient function of yeast trehalose synthase, and also may permit trehalose synthase to function efficiently at stages of yeast growth when native trehalose synthase would be inhibited by cytosolic phosphate. We disclose that intact trehalose synthase can be liberated from phosphate inhibition by treatment with trypsin in vitro.

From the knowledge gained from the present invention, it is possible to produce trehalose recombinantly by transforming a host cell with the appropriately modified TPS1, TSL1 and TSL2 genes. Methods of transformation and appropriate expression vectors are well-known in the art. In a preferred embodiment of the invention, the host is co-transformed with TPS1 and one or both of the other genes. However, examples are disclosed in which transformation with TPS1 alone caused the appearance of Tre6P synthase activity in *E. coli* and both Tre6P synthase activity and trehalose in *Nicotiana tabacum*.

Expression vectors are known in the art for both eukaryotic and prokaryotic systems, and the present invention contemplates use of both systems. For transformation of yeast at least two classes of promoters are contemplated. Yeast that accumulates more trehalose but at the usual time (i.e., after consumption of fermentable carbon sources) can be made by inserting extra copies of the genes under their own promoters, or stronger promoters with similar control. Such yeast can have improved storage properties and stress resistance and be more economic sources of trehalose. Yeast that synthesizes trehalose during fermentation can be made by replacing the genes' own promoters with promoters (such as ADC1) that are active during fermentation. As explained above, such yeast can have increased fermentation rates, ethanol yields and resistance to osmotic and temperature stress during fermentation.

Also contemplated are modifications of the DNA sequence which would provide "preferred" codons for particular expression systems (e.g., bacteria and higher plants). In addition, the TPS1, TSL1 and TSL2 DNA sequences may be modified by certain deletions or insertions, provided the translated polypeptides are enzymatically functional. Expression of functional polypeptides from TPS1, TSL1 and TSL2 may be confirmed by assaying for Tre6P synthase and/or Tre6Pase activity in the expression system by the methods described herein. Deletion of the first 330 amino acids or so from the 123 kDa long chain to give an enzyme active at higher phosphate and lower F6P concentrations has already been mentioned.

It is well known that proteins with the same function in different organisms are often homologous. The gene encoding a particular protein in one organism can often be isolated using probes and PCR primers designed from the sequence of the gene encoding the corresponding protein of another organism. The sequences now disclosed for TPS1 and TSL1 can be used to clone the genes of polypeptides of other microbial synthases.

The genes of the present invention and those encoding components of other microbial trehalose synthase systems may be transferred to and expressed in plants. DNA vectors or ballistic methods can be used to transfer the genes. This may be done preferably by functionally joining the coding sequences of the genes to appropriate plant promoters. Constitutive promoters (such as the Cauliflower mosaic virus 35S promoter), tissue specific promoters (such as the patatin promoter) or non-constitutive promoters could all be used, with particular advantages in particular cases. However, although the accumulation of trehalose at certain times (e.g., during exposure to stress or in a mature plant) and in certain tissues (e.g. storage organs or, at appropriate times, frost-sensitive tissues) is expected to be beneficial, or at least harmless to a plant, there is a distinct possibility that at other times and in other tissues the accumulation of trehalose may be harmful to a plant (Veluthambi et al. [1981] Plant Physiol. 68, 1369-1374). It would therefore be advantageous to use a plant promoter that does not permit full expression of the microbial gene(s) causing trehalose synthesis until the plant is mature or encounters environmental conditions, including drought and low temperature, in which the benefits of trehalose outweigh its possible disadvantages to the plant. Several examples of such non-constitutive plant promoters are known to those familiar with the art, including the small subunit ribulose-1,5-bisphosphate carboxylase (Rubisco) promoter, which drives the light-induced expression of the small subunit of RUBISCO (Krebbers et al. [1988] Plant Mol. Biol. 11, 745-759).

We disclose tobacco plants transformed with the coding sequence (open reading frame, ORF) of the yeast TPS1 gene correctly fused to the ATS1A promoter of a Rubisco small subunit gene. We disclose that the transformed plants are healthy and fertile and contain trehalose in their leaves. Untransformed tobacco or tobacco transformed with a similar vector lacking the TPS1 gene does not contain trehalose.

One of these transformed tobacco plants (Transformant 4) is shown to contain Tre6P synthase activity. The free 56 kDa subunit is known to be unstable when isolated from the intact trehalose synthase complex of yeast (Example 9).

Methods are described by which a person skilled in the art can co-transform plants with the TPS1 gene and one or both of the other yeast trehalose synthase genes (TSL2 and TSL1) under the control of appropriate promoters, e.g. the ATS1A promoters. Such co-transformation is expected to increase the trehalose content of the plants compared to that of plants containing only TPS1, because the subunits encoded by TSL2 and TSL1 will stabilise the 56 kDa subunit.

Plants containing trehalose as a result of transformation with one or more of these yeast genes for trehalose synthase can be used in several ways. For example, trehalose can be extracted from the plants on a commercial scale and used to preserve the flavor and structure of food stuffs during drying. For this application the trehalose would preferably be accumulated in a storage organ, such as the tuber of a potato or the fruit of a banana. Plant promoters are known in the art (e.g., the patatin promoter) that cause expression specifically in storage organs. In one aspect of the present invention, the coding sequences of microbial genes for trehalose synthase, such as TPS1, TSL2 and TSL1, are fused to such promoters in the same way as the TPS1 coding sequence was fused to the ATS1A promoter, and suitable plants are transformed with these DNA constructions. The trehalose accumulated in the storage organs may then be extracted. In other cases (e.g., tomatoes), the trehalose accumulated in the edible storage organ of the plant may confer a longer shelf life than exhibited by the corresponding parts of untransformed plants Transformed plants containing trehalose may also be more resistant to drought, frost and other stresses than the untransformed plants. In this aspect of the invention, the plant promoter used may be one that is induced by stress. Such promoters are known in the art, e.g. LTI78 (Nordin et al. [1993] Plant Mol. Biol. 21, 641-653) and RAB18 (Lång & Palva [1992] Plant Mol. Biol. 20, 951-962). This will prevent the accumulation of trehalose until it is needed. In plants able to grow well whilst containing trehalose, this aspect of the invention can be achieved without resource to a stress-induced promoter, but the use of stress-induced promoters to prevent trehalose production until it is needed has the additional advantage of avoiding the yield penalty that would otherwise result from the diversion of photosynthetic capacity to trehalose synthesis.

In yet another aspect of the invention, microbial genes for trehalose synthase subunits are appropriately fused to a plant promoter (e.g., LTI78 or RAB18) that is activated by a specific event or set of conditions (e.g. cold or drought stress) so that accumulation of trehalose in the plant can be triggered to occur in the mature plant shortly before harvesting, avoiding any deleterious effects of trehalose on the early development of certain plants.

Based on the above disclosure, the transgenic plants according to the invention can be monocotyledonous plants, such as corn, oats, millet, wheat, rice, barley, sorghum, amaranth, onion, asparagus or sugar cane, or dicotyledonous plants such as alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea or coffee.

We disclose that the yeast gene TPS1 and its product are compatible with the biochemical machinery of tobacco: the gene was highly expressed and the 56 kDa subunit caused the appearance of trehalose. However, it is known in the art that plant genes often have lower A+T ratios than microbial genes, and that the expression level of heterologous genes in plants can be increased by altering the codon usage, particularly near the start of the coding sequence, towards that found in plants and similar modifications of microbial genes may be useful in the present invention.

The following examples are for illustration of the present invention and should not be construed as limiting the present invention in any manner.

EXAMPLES

General Materials and Methods
Materials

Fructose 6-phosphate (F6P) and adenosine 5'-diphosphoglucose (ADPG) were from Sigma Chemicals. Glucose 6-phosphate (G6P), phenylmethylsulphonyl fluoride (PMSF), uridine 5'-diphosphoglucose (UDPG) and other commercial reagents were from the sources stated in Londesborough & Vuorio [(1991) loc. cit.]. Truncated trehalose synthase (proteolytically activated "TPS/P") and TPS activator were prepared as described in Londesborough & Vuorio [(1991) loc. cit.]. The antisera, anti-TPS/P, anti-57K and anti-93K were made in rabbits using as antigen, respectively, truncated trehalose synthase, the short (57 kDa) chain and the 93 kDa fragment of the long chain of trehalose synthase as described in Londesborough & Vuorio [(1991) loc. cit.]. Vacuolar trehalase was partially purified as described by Londesborough & Varimo ([1984] Biochem. J. 219, 511–518) from a suc⁻gal⁻mel⁻mal⁻yeast strain (ALK02967) and did not hydrolyze sucrose, maltose or melibiose. A plasmid (YCplac111/TPS2) provided by Drs. Claudio De Virgilio and Andres Wiemken, Botanisches Institut der Universität Basel, Switzerland contained the gene TPS2 cloned into the SacI site of plasmid YCplac111. This gene is needed for Tre6Pase activity in yeast (De Virgilio et al [1993] Eur. J. Biochem. 212, 315–323) and encodes the amino acid sequences SEQ ID NOs: 29 to 38 and 44 to 49) and so is identical to the TSL2 gene disclosed by the inventors in 1992.

Buffers for enzyme extraction and purification

Two standard cocktails, HBMED (25 mM Hepes/KOH pH 7.0/1 mM benzamidine/1 mM MgCl₂/0.1 mM EDTA/1 mM dithiothreitol) and HB2M1ED (HBMED but with final concentrations of 2 mM MgCl₂ and 1 mM EDTA) were used as basal buffers during preparation of cell extracts and purification of enzyme. Where indicated, the Hepes and benzamidine concentrations were increased to 50 mM and 5 mM, respectively.

Yeasts

Commercial baker's yeast was from Alko's Rajamäki factory. The standard laboratory strains of *S. cerevisiae* used were X2180 (ATCC 26109) and S288C (ATCC 26108). Mutant strains are described in the Examples and Table 1 lists important strains of microorganisms and plasmids. Laboratory yeast were routinely grown on 1% yeast extract/2% peptone (YP) containing the indicated carbon source in aerobic shake flasks at 30° C. and 200 r.p.m. Cells were harvested by centrifugation for 5 minutes at 3000 g, resuspended in distilled water and again centrifuged 5 minutes at 3000 g. The pellets were suspended in about 20 volumes of HB2M1ED and centrifuged in tared tubes for 10 minutes at 15,000 g. Tubes and pellets were weighed to give the mass of fresh yeast. For trehalose determinations, portions of the pellets were treated as described by Lillie, S. H. & Pringle, J. R. [(1980) Journal of Bacteriology 143, 1384–1394]. The washed cells were broken by suspending them at 0° C. in 1 to 4 volumes of HB2M1ED, adding fresh stock PMSF/pepstatin (1 mg pepstatin A/ml 0.1M PMSF in methanol) to give final concentrations of 10 μg pepstatin/ml and 1 mM PMSF, and shaking with glass beads for three 1 minute periods in a Braun MK II homogenizer or (for amounts less than 0.3 g fresh yeast) by vortexing in an Eppendorf tube. The glass beads were removed and the volume of homogenate was measured. Samples for SDS-PAGE were made at once by dilution with Laemmli sample buffer [Laemmli, U. K. (1970) Nature, London 227, 680–685]. The homogenates were then centrifuged as indicated (usually 5 min at 5,000 g or 20 minutes at 28,000 g). Enzyme assays were made on the homogenates and supernatants and protein determined in the supernatants from A280 and A260 measurements.

TABLE 1

List of important strains and plasmids

| Name | Description | Source |
|---|---|---|
| *Saccharomyces cerevisiae* | | |
| X2180 (ATCC 26109) | Standard laboratory yeast (diploid) | — |
| S288C (ATCC 26108) | Standard laboratory yeast (haploid) | — |
| Klg 102 | cif1-102, leu1, ura1, trp5, MATα | 1 |
| MV6807 | fdp1, leu2, ura3, his3, lys2, ade8, trp1, MATα | 2 |
| S150-2B | leu2, his3, trp1, ura3, Mata | — |
| ALK03569 | tps1::LEU2 (from S150-2B) | This work |
| ALK03570 | tps1::LEU2 (from S150-2B) | This work |
| WDC-3A | cif1::HIS3, his3, ura3, ade2, MATα | 3 |
| *Escherichia coli* | | |
| DH5α | | |
| MC1061 | | |
| HB101 (ALKO 683) | | |
| ALK03566 | HB101 containing pALK752 | This work |
| ALK03568 | HB101 containing pALK754 | This work |
| Plasmids | | |
| pALK751 | pBluescript containing an 8.2 kb insert comprising TSL1 | This work |
| pALK752 | pBluescript containing a 2.5 kb insert comprising TPS1 | This work |
| pALK753 | pBluescript containing a 3.3 kb insert comprising the ORF of TPS1 | This work |
| pALK754 | pBluescript containing a 4.4 kb insert comprising TSL1 | This work |
| pALK756 | pBluescript containing a 3.5 kb insert comprising at least part of TSL2 | This work |
| pALK757 | pBluescript containing an insert comprising the ORF of TSL1 | This work |
| pMB14 | YEp352 containing CIF1 | 3 |
| pGSFR401 | Source of ATS1A promoter | |
| PDE1001 | Plant transformation vector | |
| pKOH51 | pDE1001 carrying pATS1A-TPS1-3'G7 chimeric gene | This work |

Sources:
1. Dr. D. Fraenkel, Harvard Medical School, U.S.A.
2. Dr. J. Thevelein, Lab voor Plantenbioch., Heverlee, Belgium.
3. Dr. C. Gancedo, CSIC, Madrid, Spain.

Enzyme Assays

With microbial materials, Tre6Pase and Tre6P synthase standard assays and other kinetic measurements were made as described by Londesborough & Vuorio [(1991) loc. cit.] except that the standard Tre6P synthase assay mixture contained 5 mM F6P unless stated otherwise. Where appropriate, Tre6P synthase assays were corrected by measuring UDP production from UDPG in the absence of G6P and F6P.

For work with plant material, the Tre6P synthase assay system of Lapp et al ([1971] J. Biol. Chem. 246, 4567–4579)

was modified as follows. About 500 mg of frozen plant material was weighed and then ground to a fine powder with a mortar and pestel on solid $CO_2$. The powder was transferred to 0.7 ml of HB2M1ED containing 50 mM HEPES, 1 mM PMSF, and 10 µg/ml each of pepstatin A and leupeptin and allowed to melt. The resulting homogenate was centrifuged 10 min at 17 000 g. A 10 µl sample of the supernatant was added to 90 µl of reaction mixture containing 40 mM HEPES/KOH pH 7.0, 10 mM $MgCl_2$, 10 mM glucose 6-phosphate, 5 mM fructose 6-phosphate, 5 mM uridine-diphosphoglucose (UDPG) and 1 mg/ml bovine albumin and incubated at 30° C. for the required time. The reaction was stopped by 2 min at 100° C. Sugar derivatives (including any sucrose formed) except for trehalose and trehalose 6-phosphate were destroyed by adding 50 µl 0.6M HCl and heating for 5 min at 100° C. and then 50 µl of 8% NaOH and heating for 15 min at 100° C. Remaining carbohydrate (i.e., trehalose and trehalose 6-phosphate) were then determined with the anthrone assay (Trevelyan & Harrison |1956| Biochem. J. 63, 23–33).

Trehalose Assays of Plant Materials

About 500 mg of frozen plant material was quickly weighed into a glass tube. Hot, distilled water (1 ml) was added and the mixture was boiled for 20 min, the leaf material being broken up at intervals with a blunt glass rod. The liquid phase was collected with a pasteur pipette and the solid re-extracted with 0.5 ml of water. The combined liquid phases were centrifuged. The supernatant was analyzed (in some cases after treatment with alkaline phosphatase or a specific trehalase) by using a Dionex DX-300 liquid chromatograph equipped with a 42039 electrochemical combination detector with a 42300 PED-2 gold working electrode and Ag/AgCl reference. Samples (25 µl; in triplicate) were injected via a 43096 Carbopac PA-1 (4×50 mm) pre-column onto a 35391 Carbopac PA-1 (4×250 mm) column and eluted with water at 1 ml/min. The eluate was mixed with post-column reagent (0.6 ml/min of 0.3M NaOH). Trehalose emerged at about 3 min, well before the glucose and sucrose peaks, which emerged at ca 20 min.

DNA manipulations

Stratagene's (La Jolla, Calif.) *Escherichia coli* strain XL-1 Blue {recA1, endA1, gyrA96, thi, hsdR17, supE44, relA1, lac, [F´ proAB, lacIq ADM15, Tn10 (tetR)]} were used as host bacteria. The *E. coli* strains DH5α and MC1061 were also used for preparing plasmids for use in plant transformations. When needed, XL-1 Blue cells were made competent by the method of Mandel & Higa (1970) Journal of Molecular Biology 53, 159–162]. The cloning vector was Stratagene's Lambda Zap II, predigested with EcoRI, where the cloning site is near the N-terminus of the gene for β-galactosidase, thus enabling the color selection of recombinant clones. The sequencing vectors M13mp18 and M13mp19 from Pharmacia LKB Biotechnology were also used.

High molecular mass DNA from the haploid S288C strain was prepared as described Johnston, J. R. |(1988) in Yeast, A Practical Approach, IRL Press, Oxford| and partially digested with either HaeIII or EcoRI restriction enzyme. For the large scale HaeIII digestion, e.g., a reaction mixture of 330 µl containing 30 µg of DNA and 4.8 U of enzyme was incubated at 37° C. for 60 minutes. The reaction was stopped with 10 µl of 0.5M EDTA and transferred to ice. The methods for such digestions and their agarose gel electrophoretic analysis are well known in the art and are described, e.g., in Sambrook et al., Molecular Cloning, A Laboratory Manual [Cold Spring Harbor Laboratory Press, 2nd ed., (1989)|.

Plasmid DNA was isolated using standard methods for small scale purification Sambrook et al. |(1989) Molecular Cloning, A Laboratory Manual, 2nd ed., Cold Spring Harbor Laboratory Press, hereby expressly incorporated by reference|. Large scale purifications of plasmid DNA were done with Qiagen tip-100 columns from Diagen following their instructions.

DNA sequences were determined either manually by the dideoxy-chain termination method |Sanger et al. (1977) Proceedings of the National Academy of Sciences U.S.A. 74, 5463–5467|, sequencing directly from pBluescript plasmids, or automatically with the Applied Biosystems Model 373A automatic DNA sequencer, sequencing either directly from these plasmids or from M13 subclones.

Southern and Western hybridizations and other standard manipulations were carried out by well known procedures |see, e.g., Sambrook et al. (1989) loc. cit.|. For Western analyses of plant materials, proteins were extracted with the following buffer: 50 mM Tris/HCl pH 7.2, 250 mM sucrose, 5 mM EDTA, 10 mM $MgCl_2$, 1 mM $CaCl_2$, 10 mM β-mercaptoethanol, 1 mM PMSF, 30 µM pepstatin, 50 µM leupeptin and 15 µM aprotinin. Insoluble material was removed by two centrifugations (13.000 g for 10 min). The protein concentration in the supernatants was measured according to Bradford (|1976| Anal. Biochem. 72, 248–254) using bovine albumin as standard. Equal amounts of soluble proteins were loaded onto SDS-PAGE for immunological studies.

Example 1

Purification of intact trehalose synthase

Intact trehalose synthase was purified from commercial baker's yeast. The method described by Londesborough & Vuorio |(1991) loc. cit.| for purification of "proteolytically activated TPS/P" was modified as follows:

1. All buffers contained 2 mM $MgCl_2$ and 1 mM EDTA. This increased yields in the early steps and probably helped to decrease proteolysis in the later steps.
2. In the first ammonium sulphate fractionation, the EDTA concentration was increased to 2.5 mM before addition of ammonium sulphate.
3. All buffers were adjusted to between 0.4 and 1 mM PMSF and between 4 and 10 µg pepstatin A/ml by addition, immediately before use, of the appropriate amount of a freshly prepared stock solution containing 1 mg pepstatin A/ml 0.1M PMSF in methanol (called, stock PMSF/pepstatin). When, as in chromatography, buffers were used for several hours, more stock PMSF/pepstatin was added at intervals, but so as not to exceed 1.5% methanol in the buffer, or a fresh lot of buffer was taken into use, because of the short half-life of PMSF in aqueous solution. All columns were equilibrated with at least one bed volume of buffer containing PMSF and pepstatin A immediately before application of enzyme.
4. Experience permitted the enzyme-containing fractions (a total of 17.8 ml in the preparation of Table 2) from Heparin-Sepharose to be identified as soon as they were eluted. Stock PMSF/pepstatin (150 µl) and 0.1M EDTA (200 µl) were immediately added to them. Then 7.2 g of powdered ammonium sulphate was slowly added (over 20 min). After 30 min equilibration, the mixture was centrifuged 15 min at 28.000 g. The pellets were packed for 5 min at 28.000 g and expressed buffer was removed with a pasteur pipette. The pellets were dissolved to 2.0 ml in HB2M1ED containing 0.8 mM PMSF and 8 µg pepstatin A/ml, centrifuged 5 min at 28.000 g and applied to a 2.6×34 cm column of Sepharose 6B freshly equilibrated with HB2M1ED containing 50 mM NaCl, 0.4 mM PMSF and 4 µg pepstatin A/ml. The interval between elution from Heparin-Sepharose and application to Sepharose 6B was 5 h. In the Londesborough & Vuorio |(1991) loc. cit.| procedure, the Heparin-Sepharose eluates were stored at about 3° C., without addition of PMSF or pepstatin A, for 5 days before the second ammonium sulphate fractionation and application to Sepharose 6B.

5. Fractions (3.7 ml) from the Sepharose 6B column were immediately mixed with 20 µl of stock PMSF/pepstatin and then assayed. Again, experience permitted the correct fractions to be pooled, based on activity and A280 measurements without SDS-PAGE analysis, and immediately applied to a 0.7×7 cm column of UDP-Glucuronate-Agarose equilibrated with HB2M1ED containing 50 mM NaCl, 0.4 mM PMSF and 4 µg pepstatin A/ml. The enzyme was eluted as described by Londesborough & Vuorio [(1991) loc. cit.] and 10 µl of stock PMSF/pepstatin added to each 1.7 ml fraction. Each fraction was divided into three. Two portions were stored at −70° C. and one at 0° C.

Table 2 summarizes a purification and FIG. 1 shows the SDS-PAGE analysis of fractions eluted from UDP-Glucuronate-Agarose. No obvious differences were apparent between enzyme eluted by 0.2M NaCl and that eluted by 10 mM UDPG/0.4M NaCl. The major bands present had molecular masses of 57, 99 and 123 kDa. Several weaker bands were present between the 123 kDa band and about 90 kDa. In Western analyses the 123 kDa, 99 kDa and most, if not all, of the fainter bands in this region were recognized by the anti-TPS/P and anti-93K sera. This suggests that the fainter bands are partially degraded long chains. The weak bands at 68 kDa also reacted with the anti-93K serum, but could be removed by chromatography on DEAE-cellulose (see Example 9). When the antibodies from anti-93K serum that bound to the 99 kDa band were eluted from a nitrocellulose blot [as described by Pringle, J. R. (1991) Methods in Enzymolgy 194, 565–590] and used to probe another blot, they bound also to the 123 kDa band, showing that the two long chains of trehalose synthase have epitopes in common.

Intact enzyme binds less tightly to the UDP-Glucuronate-Agarose than the truncated enzyme purified by Londesborough & Vuorio [(1991) loc. cit.] and the proportion of enzyme remaining bound at 0.2M NaCl varied from preparation to preparation. When #9 of Table 2 was re-run on the same column, 76% of the Tre6P synthase activity was again recovered at 0.2M NaCl (and 25% by 0.4M NaCl/10 mM UDPG), so that overloading of the column is not the reason why this enzyme eluted at 0.2M NaCl. However, when enzyme eluted at 0.2M NaCl was truncated with trypsin as described in Example 10, it then bound to the column at 0.2M NaCl and was only recovered at 0.4M NaCl/10 mM UDPG. Thus, as well as altering the kinetic properties of the enzyme (see Examples 10 & 12), this truncation also increases the affinity for UDP-Glucuronate-Agarose. Presumably there are subtle differences in factors such as the amount of adventitious proteolysis and state of aggregation between enzyme eluted at 0.2M NaCl and that remaining bound. For the preparation summarised in Table 2, the ratio of standard Tre6Pase and standard Tre6P synthase activities increased from 22% in #9 to 39% in #14, showing that there are differences, even though they could not be clearly detected by SDS-PAGE.

These findings disclose that a highly purified trehalose synthase, containing a 57 kDa short chain, a 123 kDa long chain and a 99 kDa polypeptide that is recognised by the anti-93K serum, possesses both Tre6P synthase activity activatable by TPS-Activator protein (or F6P) and Tre6Pase activity. The rate of hydrolysis of 1 mM G6P in either phosphate or Hepes buffer was less than 1% of that of 0.5 mM trehalose-6-phosphate, so that the Tre6Pase activity is highly specific. An unexpected finding is that this highly purified preparation contains the 99 kDa polypeptide, which is not present in the purified truncated trehalose synthase. It is disclosed later that this polypeptide is not a degradation product of the long (123 kDa) chain, whereas both the 86 and 93 kDa polypeptides of truncated enzyme contain amino acid sequences that identify them as fragments of the long (123 kDa) chain. This novel preparation possesses some unexpected catalytic properties, which are described in more detail in Example 11.

TABLE 2

Purification of intact trehalose synthase
The preparation is from 60 g of pressed baker's yeast. Tre6P synthase activities "Without Activator" were measured as described by Londesborough & Vuorio [(1991) loc. cit.], i.e., in the absence of F6P. Assays "With Activator" were determined similarly but in the presence of a saturating amount of pure TPS activator (similar values were obtained when some fractions were later assayed in the presence of 5 mM F6P instead of TPS activator, and are shown in parentheses). ND, not determined.

| Fraction | Volume (ml) | Without Activator | | | With Activator | | |
|---|---|---|---|---|---|---|---|
| | | U/ml | U/mg | Total U | U/ml | U/mg | Total U |
| 1st (NH₄)₂SO₄ Precipitate | 13.4 | 58 | 1.0 | 810 | ND | ND | ND[b] |
| G25 eluate | 22.2 | 30 | 1.1 | 668 | ND | ND | ND |
| Heparin-Sepharose eluate | 18.2 | ND | ND | ND | ≈21 | ≈11 | ≈380 |
| Sepharose 6B eluate | 26 | 1.4 | 5.1 | 36 | 4.7 | 17 | 121 |
| UDP-glucuronate agarose eluates: | | | | | | | |
| at 0.2 M NaCl | | | | | | | |
| #9 | 1.7 | 4.6 | 3.1 | — | 11.5(12) | 12 | |
| #10 | 1.7 | ND | ND | ND | 12.2 | 21 | |
| #11 | 1.7 | ND | ND | ND | 6.3 | 23 | 58 |
| #12 | 1.7 | ND | ND | ND | 3.9(3.3) | 22 | |
| at 0.4 M NaCl/10 mM UDPG | | | | | | | |
| #13 | 1.7 | 2.1 | — | — | 5.9(6.2) | 25–30* | |
| #14 | 1.7 | 3.7 | — | — | 9.3 | 25–30* | 27 |
| #15 | 1.7 | ND | — | — | 0.8 | — | |

*based on protein contents estimated from Coomassie blue-stained SDS-PAGE gels
[b]Results from other preparations show that the activity with excess TPS-activator (or 5 mM F6P) is not, at this step, more than 10% greater than that without activator.

Example 2
Increased expression by S. cerevisiae of the long and short chains of trehalose synthase after consumption of glucose Three 500 ml lots of YP/2% glucose in 1 l shake flasks were each inoculated with 1 ml of a suspension of X2180 cells of A600 1.0 and shaken at 200 r.p.m. at 30° C. At the times shown in Table 3, the cells were harvested, broken and analyzed as described in General Materials and Methods. The 28,000 g supernatants were stored for a week at −18° C., thawed and re-centrifuged for 20 min at 28,000 g. Portions of 150 µl (each equivalent to 53 mg of fresh yeast) were mixed with 30 µl of anti-TPS/P serum, equilibrated for 30 min at 0° C. and centrifuged for 10 min at 10,000 g. The pellets were washed with 250 µl of HBMED and then dissolved in Laemmli sample buffer and subjected to SDS-PAGE (FIG. 2). Bands at 57, 99 and 123 kDa were strong in the sample (C) from stationary phase yeast and in the sample (B) harvested immediately after disappearance of glucose from the medium, but were absent or very weak in the sample (A) from yeast growing in the presence of 1.2% glucose.

TABLE 3

Appearance of Tre6P synthase and Tre6Pase activities in X2180 yeast grown on YP/2% glucose.
Enzymes were assayed in the 28,000 g supernatants.

|  | A | B | C |
| --- | --- | --- | --- |
| Age (h) | 16.1 | 18.1 | 39.0 |
| Residual glucose (g/100 ml medium) | 1.2 | ≦0.001 | ≦0.001 |
| Fresh yeast mass (mg/ml medium) | 7.6 | 14.8 | 29.5 |
| Trehalose (mg/g dry yeast) | 0.73 | 3.1 | 94 |
| Tre6P synthase (U/g fresh yeast) | 1.2 | 7.4 | 10.5 |
| Tre6Pase (U/g fresh yeast) | 0.29 | 2.2 | 3.0 |
| Tre6P phosphatase/synthase (%) |  | 2430 | 29 |

Control experiments (not shown) indicated that pre-immune serum did not precipitate the 57, 99 and 123 kDa bands, and that using 50 µl of serum instead of 30 µl did not precipitate more of these three bands from the C sample.

These results disclose that the co-ordinate, 7-fold increase in Tre6P synthase and Tre6Pase activities that occurs during less than 2 h when glucose disappears from the medium is accompanied by increases in the amounts in yeast of three polypeptides, of mass 57, 99 and 123 kDa, that are immunoprecipitated by anti-TPS/P serum. These polypeptides are those found in the intact trehalose synthase purified in Example 1. Thus, increase in the amount of enzyme protein is a major mechanism by which the capacity of yeast to synthesize trehalose is increased.

Example 3
Determination of the N-terminal amino acid sequences of peptides isolated from the various polypeptides of trehalose synthase The 57, 86 and 93 kDa polypeptides of the truncated trehalose synthase were separated by SDS-PAGE, digested on nitrocellulose blots and fractionated by HPLC as described by Londesborough & Vuorio |(1991) loc. cit.|. Also, these polypeptides and polypeptides of molecular mass 57, 99 and 123 kDa immunoprecipitated from yeast extracts as described in Example 2 were separated by SDS-PAGE and digested in the gel with lysylendopeptidase C as described by Kawasaki, H., Emori, Y. and Suzuki, K. (in press). The derived peptides were separated by HPLC using a DEAE pre-column before the reverse-phase column essentially as described by Kawasaki et al |(1990) Analytical Biochemistry 186, 264–268|. The 99 kDa polypeptide isolated by chromatography on phosphocellulose in the absence of triton (see Example 9) was digested with lysylendopeptidase C and the peptides separated by HPLC. In all cases, isolated peptides were sequenced in a gas-pulsed liquid phase sequencer as described by Kalkinen, N. & Tilgman, C |(1988) Journal of Protein Chemistry 7, 242–243|, the released PTH-amino acids being analysed by on-line, narrow-bore, reverse-phase HPLC. The sequences are shown in Table 4.

TABLE 4

Figure 3B:
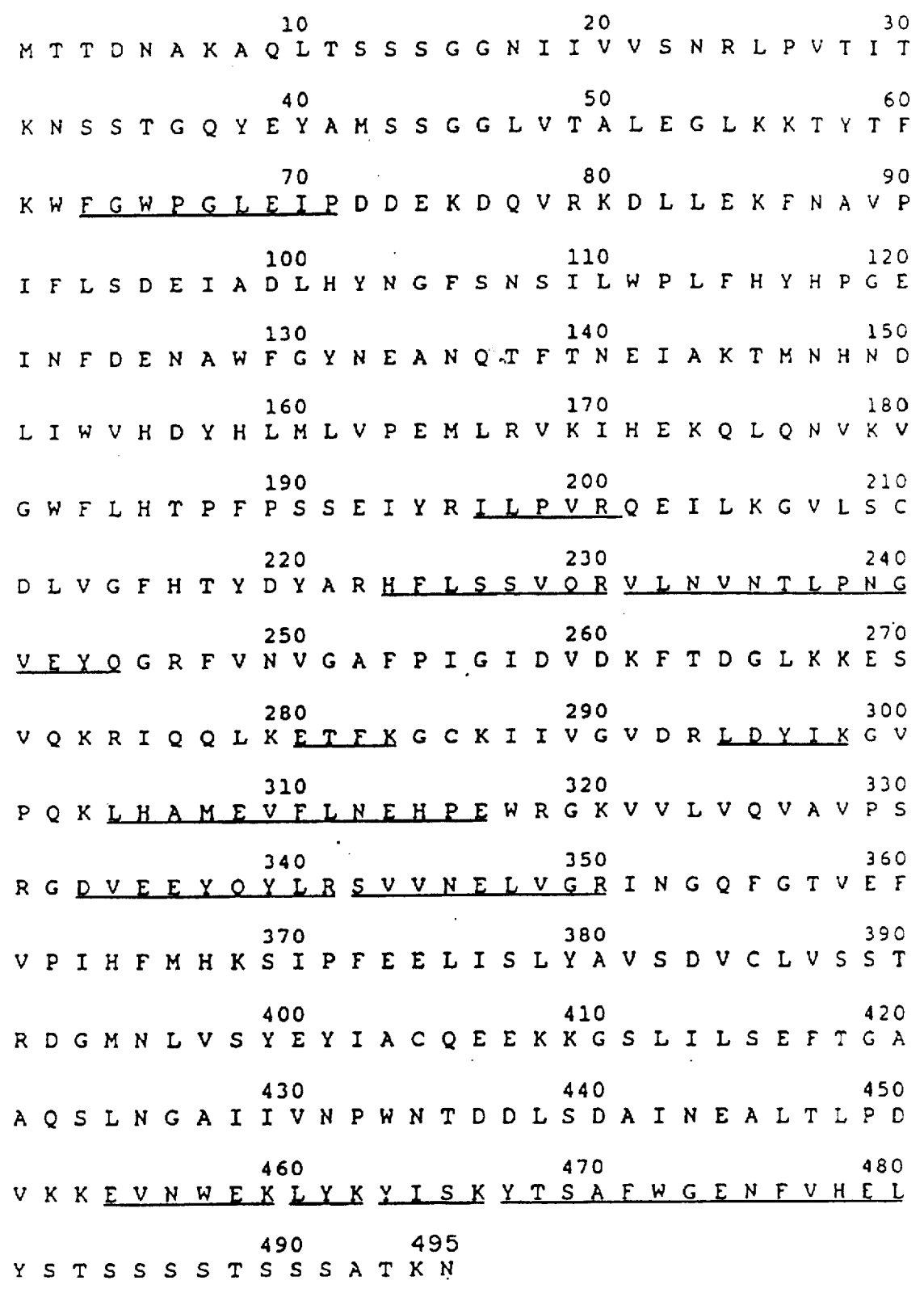

N-terminal amino acid sequences of peptides isolated from (fragments of) the polypeptides of trehalos synthase.
When two sequences were obtained from the same HPLC peak, they are shown as a and b sequences, where possible according to the sequences predicted from the genes. Tentative identifications from the amino acid sequencer are shown by the one letter codes followed by double queries. Unidentified residues are shown by Xaa. (In the Sequence Listings, also tentatively identified residues are indicated as Xaa). The location of each amino acid sequence in the short (S) and long (123 kDa) (L) chains of FIGS. 3b and 4b is shown below the sequence.

Short (57 kDa) chain peptides
Tryptic peptides from blots of the 57 kDa polypeptide tide from truncated trehalose synthase.

| 848 | Tyr—Ile—Ser—Lys |
|  | (SEQ ID NO:5) (S 463–66) |
| 850 | Asp—Val—Glu—Glu—Tyr—Gln—Tyr—Leu—Arg |
|  | (SEQ ID NO:6) (S 333–41) |
| 859 | His—Phe—Leu—Ser—Ser—Val—Gln—Arg |
|  | (SEQ ID NO:7) (S 223–30) |
| 862a | Val—Leu—Asn—Val—Asn—Thr—Leu—Pro—Asn—Gly—Val—Glu—Tyr—Gln |
|  | (SEQ ID NO:8) (S 231–44) |
| 862b | Ser—Val—Val—Asn—Glu—Leu—Val—Gly—Arg |
|  | (SEQ ID NO:9) (S 342–50) |
| 863 | Leu—Tyr—Lys |
|  | (S 460-2) |
| 864 | Glu—Thr—Phe—Lys |
|  | (SEQ ID NO:10) (S 280–3) |
| 866 | Leu—Asp—Tyr—Ile—Lys |
|  | (SEQ ID NO:11) (S 294–8) |
| 870 | Ile—Leu—Pro—Val—Arg |
|  | (SEQ ID NO:12) (S 196–200) |

From lysylendopeptidase C digests of immunoprecipitated 57 kDa band

| 966a | Glu—Val—Asn—Xaa—Glu—Lys |
|  | (SEQ ID NO:13) (S 454–9) |
| 966b | Phe—Tyr—Asp—Xaa—L?? |
|  | (SEQ ID NO:14) (not found) |
| 980 | Leu—Xaa—Ala—Met—Glu—Val—Phe—Leu—Asn—Glu—Xaa—Pro—Glu |
|  | (SEQ ID NO:15) (S 304–16) |
| 981 | Tyr—Thr—Ser—Ala—Phe—Trp—Gly—Glu—Asn—Phe—Val—Xaa—Glu—Leu |
|  | (SEQ ID NO:16) (S 467–80) |
| 987 | Phe—Gly—Xaa—Pro—Gly—Leu—Glu—Ile—Pro |
|  | (SEQ ID NO:17) (S 63–71) |

Long (123 kDa) chain peptides
Tryptic peptides from blots of the 86 and 93 kDa fragments.

| 889 | D??—Gly—Ser—Val—Met—Gln |
|  | (SEQ ID NO:18) (L 587–592) |
| 890/891 | Leu—Pro—Gly—Ser—Tyr—Tyr—Lys |
|  | (SEQ ID NO:19) (L 917–23) |
| 892a | Ala—Ile—Val—Val—Asn—Pro—Met—Asp—Ser—Val—Ala |
|  | (SEQ ID NO:20) (see peptide 1299) |
| 892b | Met—Ile—Ser—Ile—Leu |
|  | (SEQ ID NO:21) (L 842–7) |

From lysylendopeptidase digest of combined 86 and 93 kDa fragments.

| 1171 | Arg—Arg—Pro—Gln—Trp—Lys |
|  | (SEQ ID NO:22) (L 770–5) |

TABLE 4-continued

From lysylendopeptidase digest of the 86 kDa fragment.

| | | |
|---|---|---|
| 1479 | Thr—Leu—Met—Glu—Asp—Tyr—Gln—Ser—Ser—Lys (SEQ ID NO:52) (L 816–26) | |
| 1483a | Ala—Phe—Glu—Asp—His—Ser—Trp—Lys (SEQ ID NO:78) (L 445–52) | |
| 1483b | Ala—Gly—His—Ala—Ile—Val—Tyr—Gly—Asp—Ala—Thr—Ser—Thr—Tyr—Ala—Lys (SEQ ID NO:79) (L 1064–79) | |
| 1481 | Glu—Arg—Leu—Pro—Gly—Ser—Tyr—Tyr—Lys (SEQ ID NO 80) (L 914–23) | |

From lysylendopeptidase digest of the 93 kDa fragment.

| | | |
|---|---|---|
| 1480 | Thr—Leu—Met—Glu—Asp—Tyr—Gln (SEQ ID NO:81) (L 816–23) | |
| 1484a | Ala—Phe—Glu—Asp—His—Ser—Trp—Lys (SEQ ID NO:78) (L 445–52) | |
| 1484b | Ala—Gly—His—Ala—Ile—Val—Tyr—Gly—Asp—Ala—Thr—Ser—Thr—Tyr—Ala—Lys (SEQ ID NO:79) (L 1064–79) | |
| 1485 | Glu—Arg—Leu—Pro—Gly—Ser—Tyr—Tyr—Lys (SEQ ID NO:80) (L 914–23) | |

From lysylendopeptidase digests of immunoprecipitated 123 kDa band

| | |
|---|---|
| 1047 | Ser—D??—Pro—Gln—Lys (SEQ ID NO:23) (not found) |
| 1048 | Phe—Tyr—Arg—Asn—Leu—Asn—Gln—Arg—Phe—Ala—Asp—Ala—Ile—Val—Lys (SEQ ID NO:24) (L 453–67) |
| 1054a | Asp—Gly—Ser—Val—Met—Gln—W??—Xaa—Gln—Leu—I?? (SEQ ID NO:25) (L 587–97) |
| 1054b | Asn—Ala—Ile—Asn—Thr—Ala—Val—Leu—Glu—Asn—Ile—Ile—Pro—H??—Xaa—H??—Val—Lys (SEQ ID NO:26) (L 360–77) |
| 1061 | Leu—Val—Asn—Asp—Gln—Ala—Ser—Glu—Gly—Gln—Val—Lys (SEQ ID NO:27) (L 1052–63) |
| 1063 | V??—Gln—Asp—Ile—Leu—Leu—Asn—Asn—Thr—Phe—N?? (SEQ ID NO:28) (not found) |
| 1375 | Phe—Leu—Val—Glu—Asn—Pro—Glu—Tyr—Val—Glu—Lys (SEQ ID NO:50) (L 629–39) |
| 1376 | R??—Ile—Thr—Pro—His—Leu—Thr—Ala—Xaa—Ala—Ala (SEQ ID NO:51) (L 245–55) |
| 1377 | Thr—Leu—Met—Glu—Asp—Tyr—Gln—Ser—Ser—Lys (SEQ ID NO:52) (L 816–26) |
| 1378-I | Ile—Leu—Glu—Gly—Leu—Thr—Gly—Ala—Asp—Phe—Val—Gly—Phe—Gln—Thr (SEQ ID NO:53) (L 521–35) |
| 1378-II | Gln—Ile—Leu—Xaa—Pro—Thr—Leu—Xaa—Tyr—Gln—Ile—Pro—Asp—Asn (SEQ ID NO:54) (L 427–40) |
| 1380 | Phe—Gly—Gly—Tyr—Ser—Asn—Lys (SEQ ID NO:55) (L 319–25) |
| 1381 | Phe—Xaa—Thr—Glu—Asn—Ala—Glu—Asp—Gln—Asp—Xaa—Val—Ala—Xaa—Val—Ile—Gly—G??—Ala—Ile—Xaa—Xaa—Ile (SEQ ID NO:56) (L 931–53) |
| 1382 | Xaa—Val—Gly—Thr—Val—Gly—Ile—Pro—Thr—Asp—Glu—Ile—Pro—Glu—Asn—Ile—Leu—Ala (SEQ ID NO:57) (L 378–95) |

The 99 kDa polypeptide
From lysylendopeptidase digests of immunoprecipitated 99 kDa band

| | |
|---|---|
| 959 | Asp—Thr—Thr—Gln—Thr—Ala—Pro—Val—T??—Asn—Asn—Val—Xaa—Pro (SEQ ID NO:29) |
| 961 | Asn—Gln—Leu—Asp—Ala—A??—Asn—Tyr—Ala—Glu—Val (SEQ ID NO:30) |
| 1002a | Asn—Leu—Ser—Arg—Trp—Arg—Asn—Tyr—Ala—Glu (SEQ ID NO:31) |
| 1002b | Trp—Gln—Gly—Lys (SEQ ID NO:32) |
| 1043 | Ile—Gln—Leu—Gly—Glu—Ser—Asn—Asp—Asp—D??—L?? (SEQ ID NO:33) |
| 1055 | Glu—Val—Pro—Thr—Ile—Gln—Asp—Xaa—Thr—Asn—Lys (SEQ ID NO:34) |
| 1287 | Xaa—Tyr—Xaa—Tyr—Val—Lys (SEQ ID NO:35) |
| 1297a | Asn—Gln—Leu—Gly—Asn—Tyr (SEQ ID NO:36) |
| 1297b | Val—Ala—Leu—Thr (SEQ ID NO:37) |
| 1299 | Asp—Ala—Ile—Val—Val—Asn—Pro—Xaa—Asp—Ser—Val—Ala (SEQ ID NO:38) |
| 1306 | Ser—Leu—Leu—Asp—Ala—Gly—Ala—Lys (SEQ ID NO:44) |
| 1307a | Glu—Lys—Pro—Gln—Asp—Leu—Asp—Asp—Asp—Pro—Leu—Tyr—Leu—Thr (SEQ ID NO:45) |
| 1307b | D??—Gln—Xaa—His—Gln—Asp—Xaa—Xaa—Asn—Leu—Thr (SEQ ID NO:46) |
| 1308 | Phe—Asn—Asp—Glu—Ser—Ile—Ile—Ile—Gly—Tyr—Phe—P??—Xaa—Ala—Pro (SEQ ID NO:47) |
| 1309 | Ser—Arg—Leu—Phe—Leu—Asp—Tyr—Asp—Gly—Thr—Leu—Thr—Pro (SEQ ID NO:48) |

From lysylendopeptidase digest of 99 kDa protein purified on phosphocellulose

| | |
|---|---|
| 1451 | Gln—Leu—Gly—Asn—Tyr—Gly—Phe—Tyr—Pro—Val—Tyr (SEQ ID NO:49) |

Apart from peptide 966b, all the amino acid sequences determined from the short chain samples have been located in the protein sequence deduced from the TPS1 gene (see FIG. 3b). Apart from peptides 892a, 1047 and 1063, all the amino acid sequences determined from the 86 and 93 kDa fragments of the long chain and from the intact 123 kDa long chain itself have been located in the protein sequence deduced from TSL1. The HPLC profiles obtained from digests of the 86 kDa fragment were essentially identical with those from digests of the 93 kDa fragment when either trypsin or lysylendopeptidase C was used (not shown). Also, corresponding HPLC peaks from 86 and 93 kDa digests yielded the same sequences or double sequences (peptide pairs 890 & 891; 1479 & 1480; 1483a,b & 1484a,b; 1481 & 1485). These results disclose that both the 86 and 93 kDa polypeptides in truncated enzyme are derived from the 123 kDa long chain encoded by TSL1. In particular, it is not the case that one or other of these fragments is derived from the 99 kDa polypeptide, although contamination with minor amounts of (degradation products of) that polypeptide is probable (see below).

None of the 16 amino acid sequences obtained from the 99 kDa polypeptide is encoded by TSL1. The first 5 residues of peptide 1451 from the 99 kDa polypeptide purified on phosphocellulose are identical with the last 5 residues of peptide 1297a from immunoprecipitated 99 kDa polypeptide. This confirms that the 99 kDa polypeptide immunoprecipitated by anti-TPS/P serum from yeast extracts is the same as the 99 kDa polypeptide in purified intact enzyme. These results disclose that the 99 kDa polypeptide is not encoded by TSL1 (or TPS1) but by another gene, which the inventors call TSL2.

The origin of peptides 1047 and 1063 found in the digest of the intact (123 kDa) long chain is not known. The only peptide from the long chain fragments of truncated enzyme not encoded by TSL1 is 892a from the 93 kDa fragment. This is identical with the last 11 residues of peptide 1299 from the 99 kDa polypeptide. This suggests that the 93 kDa band was contaminated with some material derived from the 99 kDa polypeptide, although this polypeptide itself was not visible in SDS-PAGE analyses of the truncated enzyme. The identical HPLC profiles of digests of the 86 and 93 kDa fragments and the fact that only one peptide derived from the 99 kDa polypeptide was identified in these digests shows that the contamination was at a low level. This discloses that a functional truncated trehalose synthase with both Tre6P synthase and Tre6Pase activities probably requires only polypeptides encoded by TPS1 and TSL1.

Example 4
Cloning and sequencing of TPS1
(a) Preparation and screening of a yeast genomic DNA library A genomic library was constructed in the bacteriophage lambda vector, Lambda Zap II, using a partial HaeIII digest of *S. cerevisiae* strain S288C chromosomal DNA, according to Stratagene's Instruction Manual for the Zap-cDNA synthesis kit. The DNA from the ligation reaction was packaged into Giga II Gold packaging extract (Stratagene) according to the manufacturer's instructions (1990). The titer of the recombinants was determined on Luria broth plates containing X-β-galactoside (5-bromo-4-chloro-3-indoyl-β-D-galactopyranoside) as a chromogenic substrate for β-galactosidase and IPTG (isopropyl β-D-thiogalactopyranoside) as an inducer. About 50,000 recombinants were amplified on large (150 mm) NZY-plates according to Stratagene's instructions. The titre of the resulting library was $5 \times 10^9$ pfu/ml with a total of 150 ml.

Several positive clones were found by screening with anti-TPS/P serum. After three rounds of purification, all clones were positive. They were screened again, now with anti-57K serum.

For further manipulations of DNA, the plasmid part, pBluescript, of the Lambda Zap vector was excised as described in the manual for Predigested Lambda ZapII/ EcoR1 Cloning Kit (1989).

(b) Sequencing of TPS1
A strongly positive clone from the Lambda ZapII library was selected and sequenced manually. The sequence obtained included an open reading frame that encoded a 58 kDa protein, but none of the short chain peptide sequences disclosed in Example 3 was found in the amino acid sequence encoded by this ORF.

Therefore, a second clone was selected, from a group of clones that gave distinct restriction maps compared with the group including the first clone. It also responded less strongly to anti-57K serum, which is why it was not chosen in the first place. It was sequenced using the Exonuclease III/Mung Bean nuclease system for producing series of unidirectional deletions. The deletions were prepared according to Stratagene's manual for the pBluescript Exo/Mung DNA sequencing system. The plasmid was first digested with the restriction enzymes SacI, which leaves a 3' overhang, and BamHI, which leaves a 5' overhang. For filling in possible recessed 3' termini created by Mung Bean nuclease, 2.5 μl of 10× nick-translation buffer, 1 μl of dNTP (a mixture of all four dNTPs, each at 2 mM) and 1 μl (2U) of Klenow fragment were added. The reaction proceeded for 30 min at room temperature and was then stopped with 1 μl of 0.5M EDTA [Sambrook et al. (1989) loc. cit.]. The deletion time points were run on a 0.8% low melting agarose gel. The bands were cut out, melted and ligated according to Stratagene's instructions. Portions (5 μl) of each ligation mixture were used to transform XL-1 Blue cells.

The clone proved to encode all the short chain peptide sequences disclosed in Example 3, except the poorly defined pentapeptide, 966b. It is notable that the anti-57K serum alone was an inadequate tool for cloning this gene: the amino acid sequence data disclosed in Example 3 were also essential. Comparison of sequences with the Microgenie Data Bank showed that the gene sequence of the clone was available as an unknown reading frame in the post-translational region of the gene for yeast (*S. cerevisiae*) vacuolar $H^+$-ATPase. The data in the bank contain sequence errors, and have thus been erroneously interpreted as two short unidentified ORFs instead of one long ORF. The complete sequence of the TPS1 gene with 800 bp of promoter and 200 bp of terminator regions is disclosed as SEQ ID NO:1 and the amino acid sequence deduced from its ORF (starting at nucleotide 796) as SEQ ID NO:2. SEQ ID NO:1 now incorporates the following minor corrections to the promoter region, made since February 14th 1992: the original nucleotides 60 and 61 (CA) become AC, original nucleotides 646 to 653 (CGCGTGGT) become GCCGGG and the original nucleotide 711 (C) is deleted. FIG. 3A shows the promoter and terminator regions, and FIG. 3b shows the deduced amino acid sequence.

Example 5
Cloning and sequencing of TSL1 and TSL2
(a) Preparation and screening of genomic DNA libraries The gene TSL1 was first found in the same library as described in Example 4. Screening was done using first anti-TPS/P serum and then anti-93K serum. Later, another library was constructed from a partial EcoR1 digest of chromosomal DNA from *S. cerevisiae*, strain S288C, using the methods described in Example 4. The anti-93K positive clones were classified by restriction mapping into groups, not all of which can represent TSL1.

(b) Sequencing of TSL1
Clones from one group of anti-93K positive clones from the HaeIII library were partially sequenced manually and then automatically from pBluescript exonuclease deletion series as described in Example 4.

The HaeIII clones did not contain the whole of this long gene, and the N-terminus was not found in any clone. Therefore, the new EcoR1 library was constructed and screened, first with anti-93K serum and then with nucleotide probes derived from the sequenced parts of TSL1.

Several anti-93K positive clones, which also hybridized with the nucleotide probes, were obtained. These contained a plasmid with an 8.2 kb insert. From this plasmid a 2 kb fragment was cut with restriction enzymes StuI and ScaI, religated into the pBluescript SmaI site and sequenced using exonuclease deletions. The deletions were started using the enzymes SacI and SpeI. Sequencing was done with the automatic sequencer. The sequence of TSL1 was thus completed.

The complete sequence is contained in the 8.2 kb insert of the EcoRI clones, and has been deposited as plasmid pALK751 on Feb. 18, 1992 with the Deutsche Sammlung von Microorganismen (DSM), Gesellschaft fur Biotechnologische Forschung GmbH, Grisebachstr. 8, 3400 Göttingen, Germany and given the accession number DSM 6928.

The sequence is shown as SEQ ID NO:83. Nucleotides 2282 to 5575 comprise an ORF that encodes the amino acid sequence SEQ ID NO: 82. The promoter and terminator regions and amino acid sequence are also shown in FIG. 4. The amino acid sequence includes the amino acid sequences obtained from (fragments of) the long (123 kDa) chain of trehalose synthase disclosed and discussed in Example 3.

(c) Isolation and sequencing of TSL2

The information disclosed about the 99 kDa polypeptide (especially in Examples 1 & 3) provides obvious procedures for the isolation and characterization of the TSL2 gene by one ordinarily skilled in the art. Because the anti-93K serum recognizes the 99 kDa polypeptide, anti-93K positive clones isolated as described above can include clones representing TSL2. Several positive clones not representing TSL1 were identified by restriction mapping. One of these was deposited on Jan. 28th 1993 as the plasmid pALK756 (see Table 1) with the Deutsche Sammlung von Mikroorganismen und Zellkulturen GmbH. Mascheroder Weg 1 B. D-3300 Braunschweig, Germany (Accession number DSM 7425). This plasmid comprises a 3.5 kb insert in pBluescript. The insert was not cut by the restriction enzymes, NotI, SacI, SpeI or XhoI. The sequences of these and similar clones can be examined to identify an ORF that encodes the amino acid sequences of peptides isolated from the 99 kDa polypeptide (viz., SEQ ID NO:S 29 to 38 and 44 to 49). Another well established procedure is to use these amino acid sequences to design nucleotide primers that can be used to amplify parts of the TSL2 gene by the polymerase chain reaction. When a part of the TSL2 gene has been isolated and sequenced by either procedure, the rest of the gene can be easily isolated as described for TSL1.

Example 6
Characterization of TPS1 and TSL1

The nucleotide sequence of TPS1 encodes a polypeptide of 495 amino acid residues with a calculated molecular mass of 56 kDa. This open reading frame starts with an ATG codon and ends with two TGA codons. The promoter region contains a TATA box at −178 (see FIG. 3) and the sequence CCCCGC at −270, which has been implicated in catabolite repression [Nehlin & Ronne, (1990) European Molecular Biology organization Journal 9, 2891–2898]. This may account for the low expression of trehalose synthase in the presence of glucose disclosed in Example 2.

The open reading frame of TSL1 encodes a polypeptide of 1098 amino acids, corresponding to a calculated molecular mass of 123 kDa. This ORF starts with an ATG codon and ends with a TAA codon. Sixty base pairs downstream from the TAA codon is a possible TATATA transcription termination element [Russo et al. (1991) European Molecular Biology Organization Journal 10, 563–571].

The promoter sequence of TSL1 contains two putative TATA boxes at −100 and −117. The promoter was searched for possible heat shock elements and four AAGGGG elements were found (−166, −180, −232 and −378). Of these, the one furthest upstream, at −378, was part of the sequence GGTAAAAGGGGCGAA, which corresponds well to the UAS$_{-360}$ heat shock stress control element GGTAAGGGGCCAA [Marchler, G. et al (1992) Yeast 8, S154]. Two copies of the canonical heat shock element GAANNTTC were found, one at −353 and the other at −425; thus, one on either side of the UAS$_{-360}$ element.

The sequence GCCCCTGCATTTT at −327 could be a MIG1 protein binding site (the consensus sequence is TCCCCRGATTNT). MIG1 appears to act as a repressor of transcription in the presence of glucose [Nehlin, J. O. & Ronne, H. (1990) European Molecular Biology organization Journal 9, 2891–2898; Nehlin, J. O. et al (1991) ibid 10, 3373–3378]. These features of the TSL1 sequence are shown in FIG. 4.

The amino acid sequence encoded by TSL1 contains two polyglutamine tracts, four Qs starting at amino acid 42 and five Qs starting at 164. Such glutamine-rich sequences have been associated with heteromeric protein-protein interaction [Gancedo, J.-M. (1992) European Journal of Biochemistry 206, 297–313].

FIG. 5 discloses that the entire TPS1 gene exhibits 37% identity at the amino acid level to a 502 amino acid stretch from the middle of the TSL1 product. The genes are obviously closely related.

Most surprisingly, the TPS1 gene is identical to the CIF1 gene that has been recently cloned and sequenced by Gancedo's group [Gonzales et al (1992) Yeast 8 183–192]. This disclosure reveals that special methodology is required to handle mutants containing modified forms of the TPS1 gene, because cif1 mutants have severe defects in sugar metabolism, as discussed in the Detailed Description. It also explains, of course, why no recognisable short chain is present in the Klg 102 mutants, which carry the cif1 mutation (see Example 7). Previously, it has been (tacitly) assumed that failure of cif1 and fdp1 mutants to express Tre6P synthase activity is the consequence of a lengthy cascade of regulatory effects. The findings disclosed here and in Example 7 show that absence of the short chain of trehalose synthase is the primary defect, from which, in an as yet completely obscure way, the other regulatory defects of these mutants result.

S.cerevisiae chromosomes were separated by pulsed field electrophoresis, with pulse times of 60 sec for 15 h and 90 sec for 9 h at 200 volts, as recommended by the instruction manual for the CHEF-DR II BioRad Laboratories, Richmond, Calif.]. Genes were located using digoxigenin-labelled non-radioactive probes, following the instructions in the manual by Boehringer Mannheim. The following probes were used: a 2.1 kb DraI restriction fragment from TSL1 and a 1.9 kb NarI-SmaI restriction fragment of TPS1 (the SmaI site is in the linker between the insert and the vector; important restriction sites in TPS1 and TSL1 are shown in FIG. 6). TPS1 was located exclusively on Chromosome 2, which is where both FDP1 [Van de Poll and Schambert (1977) loc. cit.] and CIF1 [Gonzales et al. (1992) loc. cit.] have been located. This disclosure further strengthens the evidence for the identity of TPS1 with CIF1 and FDP1. By using the Gal4 gene as a marker for chromosome 16 TSL1 was located exclusively on the adjacent Chromosome 13. Immediately downstream of TSL1 lies, in opposite orientation, the ARGRII gene, sequenced by Messenguy et. al. [(1986) European Journal of Biochemistry 157, 77–81]. The start of the overlapping sequence is shown in FIG. 4.

Example 7
A functional TPS1 gene is required for expression of both Tre6P synthase and Tre6Pase activities The S. cerevisiae mutant Klg 102, was obtained from Dan Fraenkel (Harvard Medical School) and has the genotype MATαA, ural, leu1, trp5, cif1-102. It was routinely grown on YP/2% galactose or YP/2% glucose, and long term storage was under liquid nitrogen. As reported by others [Navon, G., et al. (1979) Biochemistry 18, 4487-4499; Ba$\bar{n}$uelos, M. & Fraenkel, D. G. (1982) Molecular and Cellular Biology 2, 921–929], this mutant would not grow on YP/2% fructose, though revertants were frequent.

Six individual colonies from each of two substrains of Klg 102, ALKO 2669 and ALKO 2670, that differed in reversion frequency and colony size, were streaked onto YP/2% fructose and YP/2% glucose at 30° C. After 45 h, all 12 streaks were growing on glucose, although slower than the control yeast, X2180, but none showed any growth on fructose. After 4 days, five of the ALKO 2669 streaks showed several large, but isolated colonies on fructose and one ALKO 2670 streak showed several small colonies on fructose. From the glucose plates, three streaks from each substrain were chosen for the smallest number of revertants on the corresponding fructose plate, and used to inoculate 100 ml portions of YPD in 250 ml shake flasks, and grown at 200 r.p.m. and 30° C. Three parallel flasks were inoculated with X2180. A600 and residual glucose in the media were monitored and samples were plated out quantitatively onto YP/2% glucose and YP/2% fructose. The ALKO 2669 cultures grew faster than the ALKO 2670 cultures, and both grew much slower then X2180 (not shown).

At appropriate times the cells were harvested, broken and analyzed as described in the General Materials and Methods. The results in Table 5 show that Tre6P synthase activity was below the detection level in the Klg 102 samples and less than 0.5% of the value in X2180, which is typical of wild type *S. cerevisiae*. This agrees with previously reported results [Paschoalin, V. M. F., et al. (1989) Current Genetics 16, 81–87]. Surprisingly, however, Tre6Pase activities were also very low, between≦1% and 5% of the X2180 values. Even this residual ability to hydrolyse trehalose-6-phosphate is likely to be due to non-specific phosphatases. Paschoalin et al. [(1989) loc. cit.] claim that Klg 102 specifically lacks UDPG-linked Tre6P synthase activity, but that, like the wild-type yeast S288C (which is the haploid form of X2180), it contains an ADPG-linked activity. If this were true, and accepting the conventional view that trehalose synthesis in yeast proceeds via free trehalose-6-phosphate, Klg 102 should contain significant Tre6Pase activity. Our results disclose that this is not the case. Furthermore, when we tested whether wild type yeast (X2180) was able to synthesise [$^{14}$C]-trehalose from [$^{14}$C]-G6P in the presence of UDPG or ADPG, we found significant activity only in the presence of UDPG. The assay systems used by Paschoalin et al. [(1989) loc. cit.] have been criticised by Vandercammen et al. [(1989) loc. cit.], so we tested the overall reaction directly. Yeast extracts were incubated in 40 mM HEPES pH 6.8 containing 1 mg BSA/ml, 10 mM MgCl$_2$ and 10 mM [U $^{14}$C]-G6P (736 c.p.m./nmol) in the presence or absence of 5 mM UDPG or 2.5 mM ADPG and presence or absence of 5 mM K phosphate. Reactions were stopped by boiling for 2 min and addition of AG1-X8 (formate) anion exchange resin, as in the Tre6Pase assay system described by Londesborough & Vuorio [(1991) loc. cit.]. Results are shown in FIG. 7. Without UDPG or ADPG, radioactivity appeared in the resin supernatants, presumably due to phosphatases active on G6P. UDPG caused a clear increase in this rate in the absence of phosphate and a marked increase in the presence of 5 mM phosphate, which stimulates the Tre6Pase activity and inhibits the Tre6P synthase activity of trehalose synthase. With UDPG and 5 mM phosphate, the increase in rate corresponded, after a lag phase, to 0.94 μmol/min/g of fresh yeast, which is about 50% of the Tre6Pase activity of this yeast at 20 mM phosphate. ADPG, however, did not cause any significant increase in the rate of appearance of radioactivity in the resin supernatant, indicating that no ADPG-linked Tre6P synthase activity was present.

TABLE 5

Growth of Klg 102 and X2180 strains on YPD

| Strain | Age (h) | Residual Glucose (g %) | Cell Mass (mg/ml) | PGI (U/G) | TPS (U/G) | TPP (U/G) | Trehalose (mg/g) | Viability Fru/Glu (%) |
|---|---|---|---|---|---|---|---|---|
| Klg 102 cultures | | | | | | | | |
| 2669/1 | 24 | ND | 4.3 | 88 | ≦0.02 | ND | ND | 2.4 |
| 2669/2 | 48 | ≦0.02 | 11.6 | 81 | ≦0.03 | 0.034 | ND | ≦1.7 |
| 2669/3 | 114 | none | 10.3 | ND | ND | ≦0.02 | ≦0.22 | ≦1.8 |
| 2670/1 | 110 | | | | | | | 1.4 |
| 2670/2 | 110 | none | 9.7 | 89 | ≦0.03 | 0.081 | ND | 4.0 |
| 2670/3 | 114 | none | 11.2 | ND | ND | ≦0.02 | ≦0.19 | ≦0.3 |
| X2180 cultures | | | | | | | | |
| 1 | 24 | ND | 19.1 | 93 | 6.3 | 1.7 | ND | ND |
| 2 | 110 | none | 31.7 | 126 | 6.3 | 2.3 | ND | ND |
| 3 | 114 | none | 34.4 | ND | ND | 2.9 | 29.3 | ND |

The cultures were performed as described in the text. Residual glucose and cell mass are given as, respectively, g/100 ml and mg/ml of growth medium. Phosphoglucoisomerase (PGI) was determined as described in Example 11. PGI, Tre6P synthase (TPS) and Tre6Pase (TPP) are given as U/g of wet cells (Tre6P synthase was determined in the presence of 5 mM F6P). Trehalose is given as mg/g of wet cells. Viability Fru/Glu shows the number of cells able to grow on fructose as a percentage of the number of cells able to grow on glucose at the time of harvesting. Cells from the cultures 2670/1 and 2670/2 were combined for breakage and subsequent analysis.
ND, not determined.

Western blots of the homogenates of Klg 102 and X2180 yeast are shown in FIG. 8. The origin of the bands marked D is not clear: they may be degraded short chain. X2180 shows a strong 57 kDa band, due to the short chain of trehalose synthase and several weak bands at 100 to 130 kDa due to intact and truncated versions of the long chain. In contrast, although the Klg 102 samples showed stronger long chain bands, because more yeast sample was applied to the gel, they showed no trace of a short chain band. Thus, Klg 102 does not contain a recognisable form of the product of the TPS1 gene (it might contain a truncated version lacking the epitopes recognised by our polyclonal antibodies), but contains normal amounts of the TSL1 product. Furthermore, the TSL1 product appears to increase as Klg 102 traverses the diauxic lag (compare e.g. lanes 3 and 2 of FIG. 8), suggesting that expression of the long chain of trehalose synthase in this yeast increases when all glucose is consumed. In wild type yeast, increases in both short and long chains occur concomitant with the increases in Tre6P synthase and Tre6Pase activities when glucose is consumed (Example 2).

These results disclose that the failure of Klg 102 to express immunologically recognisable short chain of trehalose synthase is correlated with the absence of both Tre6P synthase and Tre6Pase activities. This unexpected behaviour, in contradiction of the views of Paschoalin et al. [(1989) loc. cit.], indicates that a functional short chain is required to assemble a trehalose synthase with either partial activity.

Similar experiments were done with S. cerevisiae, strain MV6807 (obtained from Johan Thevelein, Laboratorium voor Moleculaire Celbiologie, Instituut voor Plantkunde, Heverlee, Belgium), which carries the fdp1 mutation, which is allelic to CIF1 and TPS1. This strain grew poorly on glucose (fructose was not tested) and so was grown on galactose. Stationary phase cells contained 6±6% of normal Tre6P synthase but about 20% of normal Tre6Pase. Western analyses showed the presence of a band at 57 kDa recognised by anti-57K serum as well as normal long chain bands, so the mutation in MV6807 must be an aminoacid substitution. Apparently, this substitution causes a greater decrease in Tre6P synthase activity than Tre6Pase activity.

Example 8

Biochemical evidence that a long chain of trehalose synthase is required for Tre6Pase activity Truncated trehalose synthase containing the short (57 kDa) chain and the 86 and 93 kDa long chain fragments was prepared according to the method of Londesborough & Vuorio (1991) loc. cit.] for proteolytically activated TPS/P complex. Tre6P synthase and Tre6Pase activities were assayed as described by Londesborough & Vuorio [(1991) loc. cit.]. [N-ethyl-1-$^{14}$C]-maleimide (ethyl-labelled NEM; 40 mCi/mmol) was NEC-454 from New England Nuclear. N-ethyl-[2,3-$^{14}$C]-maleimide (ring-labelled NEM; 6 mCi/mmol) was CFA 293 from Amersham International. Both were obtained as solutions in n-pentane and the manufacturer's stated specific activities were assumed to be correct. Unlabelled N-ethyl-maleimide (NEM) was E-3876 from Sigma. It was dissolved in 25 mM HEPES pH 7.0 immediately before use and standardized by absorption measurements at 305 nm, assuming an $E^{mM}$ of 0.62.

Treatment of truncated trehalose synthase with 1.9 mM NEM at 24° C. in the presence of about 0.17 mM dithiothreitol (which presumably rapidly consumes about 0.34 mM NEM) caused a rapid and essentially complete (≧98%) loss of Tre6Pase activity, but little (≦24%) loss of Tre6P synthase activity (FIG. 9). This suggested that NEM modified one or more amino acid (presumably cysteine) side chains that are required intact for Tre6Pase but not for Tre6P synthase.

To permit quantitative experiments with low concentrations of labelled NEM, the dithiothreitol in the enzyme preparation was removed by gel-filtration through Pharmacia NAP5 columns equilibrated with 1 mg BSA/ml of 25 mM HEPES pH 7.0 containing 2 mM $MgCl_2$, 1 mM EDTA and 0.2M NaCl. Recoveries of Tre6P synthase and Tre6Pase activities through this gel-filtration were above 85%.

In one experiment, 2.0 μl of 2.4 mM ethyl-labelled NEM was mixed with 150 μl of gel-filtered enzyme and incubated at 23° C. Samples (10 μl) taken at various times up to 190 min were mixed with 60 μl of Laemmli sample buffer (the mercapto-ethanol in this buffer should destroy residual NEM), boiled for 5 min and subjected to SDS-PAGE. At closely similar times (and also at 23 h) other samples (10 μl) were mixed with 100 μl (for Tre6P synthase) or 700 μl (for Tre6Pase) of 5 mg BSA/ml 25 mM HEPES pH 7.0 containing 2 mM $MgCl_2$, 1 mM EDTA, 0.2M NaCl and 1 mM dithiothreitol (the dithiothreitol should destroy residual NEM) and assayed for Tre6P synthase and Tre6Pase. The enzyme dilution used for the Tre6Pase assay was sufficient that radioactivity from the NEM (about ½ of which remains in the resin supernatant) did not interfere with the Tre6Pase determinations.

After electrophoresis, the upper (cathode) buffer, containing most of the added radioactivity, was completely removed before disassembling the apparatus. The gel was then fixed, stained and destained as described by Laemmli [(1970) Nature, London 227, 680–685] and dried. An autoradiogram of this gel (FIG. 10) showed that the 93 kDa band (and also BSA) became labelled during the experiment, while the 86 and 57 kDa bands were much more weakly labelled. The Coomassie blue stained bands and adjacent, empty areas (as blanks) were cut out of the dried gel (in later experiments, they were cut from undried gels), broken up and extracted overnight with 1 ml of 5% SDS in pre-blanked scintillation vials. Then 10 ml of a toluene/Triton X100-based scintillant was added, and the tubes were repeatedly counted using a wide energy window to minimise quench effects. After 10 h constant counting levels were reached. Excess radioactivity was calculated by subtracting a blank value obtained from empty regions of the gel. Results are shown in FIG. 11. In control experiments, in which enzyme was omitted, it was shown that the excess radioactivity found in the 93 and 86 kDa bands did not originate from potential labelling of impurities in the BSA.

FIG. 11 shows that label from NEM enters mainly the 93 kDa fragment of the long chain, with relatively small amounts entering the 86 kDa fragment and the 57 kDa short chain. Also, the amount of label entering the long chain fragments (93+86 kDa) is roughly proportional to the loss of Tre6Pase activity, but lags increasingly behind this loss: at 10.5 min 30% of the initial Tre6Pase was lost and 0.20 moles of NEM had entered the long chain fragments per mole (150 Kg) of enzyme, whereas at 190 min, 56% of Tre6Pase was lost and 0.32 moles of NEM had entered the long chain fragments. Possibly, since trehalose synthase may be an octamer (its native molecular mass is about 800 kDa), reaction of one long chain with NEM can eventually lead to loss of activity associated with the other long chains in the octamer. FIG. 12 collates data from several experiments, using both ring- and ethyl-labelled NEM. Parallel experiments with identical concentrations of ring- and ethyl-labelled NEM suggested that about 25 a of the radioactivity from ethyl-labelled NEM originally fixed in the protein was lost during SDS-PAGE processing (some loss is expected in acidic condition), and the results with ethyl-labelled NEM have been corrected accordingly. Within the limits of accuracy (a specific activity of 30 Tre6P synthase units/mg was used to calculate the mass of protein and a dimer molecular mass of 150 kDa was assumed for the truncated enzyme) complete loss of Tre6Pase reflected incorporation of rather less than 1 mole of NEM into, specifically, the long chain fragments.

Another reagent with high specificity for cysteine, dithiodinitro-benzoate (DTNB), also caused a specific loss of Tre6Pase activity: after 10 min treatment with 0.9 mM DTNB over 95% of the Tre6Pase was lost and less than 28% of the Tre6P synthase.

These findings disclose that Tre6Pase activity requires a long chain with a proper structure, because modification of a single amino acid (presumable cysteine) residue in the 93 kDa fragment eliminates Tre6Pase but not Tre6P synthase activity. Sequencing data given in Example 3 disclosed that the 93 kDa band contained material from both the 99 kDa and 123 kDa long chains. Thus, the present results disclose that either the 99 kDa or the 123 kDa or both long chains are involved in Tre6Pase activity.

Example 9
An isolated 99 kDa polypeptide from trehalose synthase contains Tre6Pase activity Because the long and short chains of trehalose synthase were difficult to separate by usual chromatographic procedures, fractionations were attempted in the presence of a non-ionic detergent. During fractionation with a NaCl gradient on DEAE-cellulose (Whatman DE52) in 1% Triton X100 at pH 8.0, the enzyme was recovered in about 90% yield at 140 mM NaCl. Some minor polypeptides (e.g. the weak 68 kDa polypeptides visible in FIG. 1) were removed, but the main 57, 99 and 123 kDa polypeptides were not resolved. However, the ratio of the 99 and 123 kDa bands changed from about 1.5 to 0.3 across the enzyme peak, while concomitantly the Tre6P phosphatase/synthase ratio decreased steadily from 0.54 to 0.42 (data not shown). This suggested that the procedure was partially resolving trehalose synthase molecules enriched in the 99 kDa polypeptide from those enriched in the 123 kDa polypeptide and that the former had a relatively higher Tre6Pase activity. By extrapolation it can be calculated that the Tre6P phosphatase/synthase ratio of (hypothetical) enzyme containing only 57 and 99 kDa chains would be 0.65±0.10, whereas that of enzyme with only 57 and 123 kDa chains would be 0.32±0.10.

Because the long chain appears to contain an avid phosphate binding site (see Examples 10 and 12), chromatography on phosphocellulose was attempted. Native trehalose synthase (4.2 Tre6P synthase units) was transferred above a PM10 membrane in an Amicon cell to 25 mM HEPES pH 7.0 containing 2 mM MgC12, 1 mM EDTA, 1 mM dithiothreitol and 0.3% Triton X100 (HMED/0.3 %T) and applied to a 0.7×4.2 cm column of phosphocellulose (Whatman P11-cellulose) equilibrated with the same buffer. The column was washed with 4 ml of HMED/0.3 %T and developed with a linear gradient from zero to 0.6M NaCl in 60 ml of HMED/0.3 %T at 5 ml/h. By 0.35M NaCl only traces of Tre6P synthase had been eluted (≦3% in the first 9 ml and s 9% spread between 0.15 and 0.35M NaCl). The gradient was interrupted and the column was washed sequentially with (a) 8 ml of 10 mM fructose-6-phosphate in HMED/0.3 %T/0.35M NaCl, (b) 6 ml of HMED/0.3 %T/0.6M NaCl and (c) 0.2M K phosphate pH 7.0/2 mM MgCl$_2$/1 mM EDTA/1 mM dithiothreitol. No Tre6P synthase or Tre6Pase activity was recovered except in a single 1.5 ml fraction in which the 0.6M NaCl began to elute. This contained 12% of the applied Tre6Pase, but≦0.1% of the applied Tre6P synthase.

Fractions were examined by SDS-PAGE (FIG. 13), which showed: (1) almost pure short chain eluted at and just before the start of the NaCl gradient in fractions devoid of enzyme activity; (2) traces of short and long chain eluted diffusely at about 0.2 to 0.35M NaCl in fractions containing altogether≦7% of the applied Tre6P synthase activity; (3) at least 50% and possibly all of the applied 99 kDa polypeptide eluted at 0.6M NaCl in the fraction containing 12% of the applied Tre6Pase activity; and (4) most of the 123 kDa polypeptide remained bound to the column.

Intact trehalose synthase has also been fractionated on phosphocellulose in the absence of Triton, and with elution by a simple linear gradient from 0 to 0.6M NaCl. Pure or nearly pure 99 kDa polypeptide eluted at about 0.45M NaCl and contained specific Tre6Pase activity ($^{14}$C-G6P was not hydrolyzed). This activity differed from the Tre6Pase activity of intact trehalose synthase in that the ratio of activities at 25 mM phosphate and 50 mM Hepes was between 1.5 and 3 in different experiments (cf. this ratio is 5 to 6 for intact trehalose synthase). Furthermore, during storage of the isolated 99 kDa polypeptide at 0° C., the Tre6Pase activity at 25 mM phosphate decreased and that at 50 mM Hepes increased, until the ratio was about 0.7 after 7 weeks.

These findings disclose that the 99 kDa polypeptide isolated from intact trehalose synthase is a specific trehalose-6-phosphatase, but that its catalytic properties are unstable and differ from the Tre6Pase activity of intact trehalose synthase. Together with the disclosure in Example 7 that yeast requires a properly functional TPS1 gene to exhibit Tre6Pase activity, the results suggest that proper folding of the 99 kDa polypeptide requires the presence of the 57 kDa chain. These findings also disclose that when the short chain is separated from the long chain by chromatography in a buffer containing 0.3% Triton, in which intact trehalose synthase is stable, it rapidly looses any Tre6Pase or Tre6P synthase activity it possessed when correctly folded in the trehalose synthase.

The findings also indicate that the full-length long chain has extraordinarily high affinity for phosphocellulose, which is consistent with the location of a high affinity phosphate binding site in a terminal portion of this chain as suggested by Examples 10 and 12.

Example 10
Truncation of the 123 kDa long chain of trehalose synthase by trypsin in vitro dramatically increases Tre6P synthase activity Removal of the N-terminal 325 or so amino acids from the 123 kDa long chain of intact trehalose synthase by treatment with trypsin in vitro produces an enzyme with catalytic properties like those of the truncated enzyme purified by Londesborough & Vuorio [(1991) loc. cit.]. In one experiment intact trehalose synthase (0.28 Tre6P synthase units, ≈9.4 µg) was incubated with or without 0.5 µg of trypsin at 30° C. in 250 µl of 13 mM HEPES pH 7.0 containing 1 mM MgCl$_2$, 0.5 mM EDTA, 0.5 mM dithiothreitol, 0.2M NaCl and 0.5 mM benzamidine. Its Tre6P synthase activity was determined at intervals using standard assay mixtures (containing 5 mM F6P) containing no or 4 mM K phosphate pH 6.8, and samples were prepared for SDS-PAGE analysis immediately before and 48 min after addition of the trypsin.

During the first 48 min the Tre6P synthase activity measured in the absence of phosphate decreased faster in the presence of trypsin than in its absence. However, in the first 10 min, trypsin caused a 4-fold increase in the activity measured at 4 mM phosphate, and by 48 min the activities with and without phosphate were essentially equal (FIG. 14). By 48 min, the 123 kDa full length long chain had disappeared and been replaced by a doublet of polypeptides at 85 kDa (FIG. 15). In contrast, the short chain (57 kDa) was unchanged and the 99 kDa band was only slightly decreased in strength. The changes in Tre6P synthase activity were accompanied by loss of about 50% of the Tre6Pase activity.

Which part of the 123 kDa chain was removed by trypsin was determined as follows. Intact trehalose synthase (180 µg) was transferred to 0.5 ml of 25 mM HEPES pH 7.0 containing 2 mM MgCl$_2$, 1 mM EDTA, 1 mM dithiothreitol and 0.2M NaCl using a Centricon 30 tube, and then treated with 11 µg trypsin at 25° C. The standard Tre6 synthase activity did not decrease during the trypsin treatment, whereas Tre6P synthase activity measured in the absence of F6P and presence of 10 mM phosphate increased from 26% to 73% of the standard activity during the first 30 min of treatment. After 68 min treatment, when SDS-PAGE analysis showed the complete disappearance of the 123 and 99 kDa bands and appearance of a doublet with apparent molecular mass about 85 kDa (the components differing by about 1.5 kDa), the mixture was centrifuged through a Centricon 30 tube to separate the tryptic peptides from the core enzyme. The retentate was then boiled in 0.5% SDS and again centrifuged through the Centricon 30 tube. The combined filtrates were diluted to 0.1% SDS and incubated for 18 h at 25° C. with 4% by weight of endoproteinase Glu-C (Boehringer). The peptides were then separated by HPLC using a DEAE pre-column and sequenced as described in Example 3.

Twenty sequences were obtained (Seq ID NOs 58 to 77 in Table 6). Fifteen of these were found in the N-terminal 325 amino acids coded by TSL1. One (peptide 1407, recovered at less than half the yield of the others) was amino acids 1089–1093, i.e., 5 amino acids from the C-terminus of the protein coded by TSL1. This peptide is presumably derived by endoproteinase Glu-C cleavage of the tryptic peptide starting after Lys 1079. Both the 86 and 93 kDa long chain fragments in the truncated trehalose synthase purified by Londesborough & Vuorio |(1991) loc. cit.| are disclosed in Example 3 to contain a peptide (1483b & 1484b) derived from Ala1064 to Lys1079, confirming that the truncated polypeptides extend at least this close to the C-terminus of the full length 123 kDa chain. The N-terminal peptide furthest from the N-terminus was peptide 1443, obtained by cleavage after Arg 335. Thus, the truncated long chain extends from Ser 336 to Lys 1079 or Asp 1098, and is predicted to have a molecular mass of 87.3 or 86.2 kDa. The SDS-PAGE analysis of trypsin-treated enzyme suggests both of these truncated chains are formed, and because the Tre6P synthase activity in the presence of F6P changes little during the trypsin treatment, the two truncated chains probably have similar activities.

Of the remaining four peptides in Table 5, two (1419b and 1437b) are still unidentified, but may originate from the 99 kDa polypeptide, whereas two (1442 and 1451) clearly originate from that polypeptide. Thus, peptide 1442 is identical to peptide 1307a of Table 4, and the first 5 amino acids of peptide 1451 are identical to peptide 1297a (Table 4).

These results disclose that removal of the N-terminal 325 amino acids of the long chain, with or without removal of the C-terminal 19 amino acids, results in a trehalose synthase that is relatively insensitive to inhibition by phosphate, and does not require F6P for full activity. Analysis of the secondary structure of the long chain according to Garnier et al |(1978) Journal of Molecular Biology, 120, 97–120| suggests that whereas the C-terminal 700 amino acids are likely to be in alpha-helices or beta-sheets, the N-terminal 360 amino acid portion of the protein is relatively devoid of such structures. Taken together, these data suggest that the N-terminal 330 or so amino acids comprise a distinct domain, that confers regulatory properties upon the Tre6P synthase activity of trehalose synthase, including sensitivity to inhibition by phosphate and a requirement for F6P to express full catalytic activity. Thus, the TSL1 gene product must also be involved in Tre6P synthase activity.

TABLE 6

Peptides released from intact trehalose synthase during activation by limited treatment with trypsin.
When two sequences were obtained from the same HPLC peak, they are shown as a and b sequences, assigned according to the sequences predicted from the TSL1 gene. Tentative identifications from the amino acid sequencer are shown by one letter codes and double queries; unidentified residues Xaa. (In the Sequence Listings also tentative identifications are indicated as Xaa). The location of each amino acid sequence in the long (123 kDa) chain of trehalose synthase in FIG. 4b is shown below the sequence.

| | |
|---|---|
| 1400 | Leu—Leu—Val—His—Ser—Leu—Leu—Asn—Asn—Thr—Ser—Gln—Thr—Ser—Leu—Glu—Gly—Pro—Asn<br>(SEQ ID NO:58) (181–200) |
| 1401 | Ser—Ser—Thr—Thr—Asn—Thr—Ala—Thr—Leu—Xaa—Xaa—Leu—Val—Ser—Ser—Xaa—Ile—Phe—Met—Glu<br>(SEQ ID NO:59) (84–104) |
| 1406 | Ala—G??—Asn—Arg—Pro—Thr—Ser—Ala—Ala—Thr—Ser—Leu—Val—Asn—Arg<br>(SEQ ID NO:60) (210–24) |
| 1407 | Xaa—Phe—Thr—Ile—Ile—S??<br>(SEQ ID NO:61) (1088–93) |
| 1408 | Asn—Leu—Thr—Ala—Asn—Ala—Thr—Thr—Ser—His—Thr—Pro—Thr—Ser—Lys<br>(SEQ ID NO:62) (105–19) |
| 1409 | Phe—G??—G??—Tyr—Ser—Asn—Lys<br>(SEQ ID NO:63) (319–25) |
| 1416 | S??—Pro—S??—Ala—Phe—Asn—R??<br>(SEQ ID NO:64) (77–83) |
| 1417a | Ile—Ala—Ser—Pro—Ile—Gln—T??—Glu<br>(SEQ ID NO:65) (145–52) |
| 1417b | Gln—Arg—Pro—Leu—Leu—Ala—Lys<br>(SEQ ID NO:66) (257–63) |
| 1418 | Phe—Phe—Ser—Pro—Ser—Ser—Asn—Ile—Pro—Thr—Asp—Arg<br>(SEQ ID NO:67) (133–44) |
| 1419a | Ala—Leu—Ser—Asn—Asn—Ile—Ser—Gln—Glu<br>(SEQ ID NO:68) (47–55) |
| 1419b | A??—L??—S??—Tyr—Thr—Pro<br>(SEQ ID NO:69) (not found) |
| 1420 | Ile—Ala—Ser—Pro—Ile—Gln—Gln—Gln—Gln—Gln—Asp—Pro—Thr—Ala—Asn—Leu<br>(SEQ ID NO:70) (159–74) |

TABLE 6-continued

| | | |
|---|---|---|
| 1437a | Thr—Met—Leu—Lys—Pro—Arg<br>(SEQ ID NO:71) (120-25) | |
| 1437b | Ile—Ile—Glu—Asp—Glu—Ala<br>(SEQ ID NO:72) ((not found) | |
| 1438 | Ile—Thr—Pro—His—Leu—Thr—Ala—Ser—Ala—Ala—Lys<br>(SEQ ID NO:73) (246-56) | |
| 1439 | Ser—Leu—Val—Ala—Pro—Ala—Pro—Glu<br>(SEQ ID NO:74) (56-63) | |
| 1442 | Lys—Pro—Gln—Asp—Leu—Asp—Asp—Asp—Pro—Leu—Tyr—Leu<br>(SEQ ID NO:75) (from 99 kDa) | |
| 1443 | Lys—Tyr—Ala—Leu—Leu—Arg<br>(SEQ ID NO:76) (330-35) | |
| 1451 | Gln—Leu—Gly—Asn—Tyr—G??—Phe—Tyr—Pro—Val—Tyr<br>(SEQ ID NO:77) ((from 99 kDa) | |

Example 11
Identification of the TPS activator as phosphoglucoisomerase

TPS activator was transferred to 0.1M Tris/HCl pH 9.0 above a PM10 membrane in an Amicon cell. A 300 μl sample (34 μg) was digested for 20 h at 37° C. by 0.8 μg of lysylendo-peptidase C (Wako). Peptides were separated by HPLC and sequenced as described in Example 3. All five sequences obtained and disclosed in Table 7 are identical to sequences found in yeast phosphoglucoisomerase (PGI).

TABLE 7

Peptide sequences from TPS activator

| TPS-Activator Peptide | | PGI Residues |
|---|---|---|
| TA1156 | TFTNYDGSK<br>(SEQ ID NO:39) | 51-59 |
| TA1158 | TGNDPSHIAK<br>(SEQ ID NO:40) | 241-251 |
| TA1159 | IYESQGK<br>(SEQ ID NO:41) | 24-30 |
| TA1160 | AEGATGGLVPHK<br>(SEQ ID NO:42) | 456-467 |
| TA1161 | LATELPAXSK<br>(SEQ ID NO:43) | 11-19 |

The PGI sequences are from Tekamp-Olson, P., et al. (1988) Gene 73, 153-161.

The PGI activity of a sample of TPS activator that had been stored for several months at 0° C. was measured in 50 mM HEPES/KOH pH 7.0, 5 mM MgCl$_2$, 5 mM F6P and 0.4 mg/ml NADP. A specific activity of 190 U/mg was found.

These findings disclose that TPS activator from *S. cerevisiae* is identical to PGI. Example 12 discloses that F6P is a powerful activator of the Tre6P synthase activity of intact, but not of truncated, trehalose synthase. Because the assay mixtures for Tre6P synthase contain G6P, it is clear that Tre6P synthase activator can activate Tre6P synthase by producing F6P from the substrate G6P. This is a complete explanation for the activation. Thus, at initial concentrations of 6.7 mM G6P and 1.9 mM F6P (i.e. G6P/F6P=3.5, the experimental equilibrium ratio) the rate was independent of TPS activator and equal to that at 9 mM G6P with TPS activator. Previous investigations |Londesborough & Vuorio (1991) loc. cit.| had to use crude preparations of intact trehalose synthase because pure intact trehalose synthase was not available. Although the effectiveness of TPS activator preparations was reported to vary between different enzyme preparations, under certain circumstances data were obtained that suggested TPS activator might interact stoichiometrically with native trehalose synthase |Londesborough & Vuorio (1991) loc. cit.|. The present findings show that this suggestion was completely incorrect. The findings also imply that kinetic data in the literature are confused, because some preparations of so-called "trehalose-6-phosphate synthase" will have contained PGI whereas some may not. With the former preparations, the activator F6P will have been generated from the substrate G6P, but the amount so generated will have depended upon the details of the experimental procedure used.

Example 12
The different kinetic behaviours of intact and truncated trehalose synthase Truncated trehalose synthase was prepared as described by Londesborough & Vuorio [(1991) loc. cit.] and contained the 57 kDa short chain and 86 and 93 kDa fragments of the long chain. Intact trehalose synthase was prepared as in Example 1. Kinetic assays were done at 30° C. as described in General Methods and Materials.

(a) The Tre6P synthase Partial Activity

TABLE 8

Inhibition of the Tre6P synthase activities of intact and truncated enzyme by phosphate at 5 mM F6P

| Added Phosphate | Intact Enzyme | Truncated Enzyme |
|---|---|---|
| None | 100% | 100% |
| 1.3 mM | 69% | 94% |
| 4.0 mM | 14% | 83% |

The effect of adding K phosphate pH 6.8 to standard assay mixtures (10 mM G6P, 5 mM UDPG and 5 mM F6P) is shown. For each enzyme, the activity without phosphate is set at 100%.

The Tre6P synthase activity of intact enzyme was much more sensitive to inhibition by phosphate than was that of the truncated enzyme (Table 8). The results in Table 8 underestimate the difference between the phosphate responses of intact and truncated enzyme, because F6P partially reverses the phosphate inhibition of intact enzyme (see below) but has virtually no effect on truncated enzyme. Table 9 shows the effect of shifting from the salt conditions of the standard assay (40 mM HEPES/KOH pH 6.8, 10 mM MgCl$_2$) to conditions closer to those of yeast cytosol. In the absence of F6P, the shift caused 67% inhibition of intact enzyme (from 43% to 14% of the standard activity) but only 10% inhibition of truncated enzyme (from 96% to 86%).

TABLE 9

Effect on the Tre6P synthase activity of intact and truncated enzyme of shifting to more physiological salt conditions

|  | Standard Cond. | | Physiological Cond. | |
|---|---|---|---|---|
|  | (5 mM F6P) | No F6P | 5 mM F6P | No F6P |
| Intact | 100% | 43% | 72% | 14% |
| Truncated | 100% | 96% | 90% | 86% |

For measurement at "physiological conditions", 1.3 mM K phosphate and 0.1M KCl were added to the standard assay mixtures and the MgCl$_2$ was decreased from 10 to 2.5 mM.

These results disclose the insensitivity of the Tre6P synthase activity of truncated trehalose synthase to physiological phosphate concentrations and the presence or absence of F6P at a concentration well above the normal value in yeast cytosol (between 0.1 and 1 mM; Lagunas, R. & Gancedo, C. (1983) European Journal of Biochemistry 137, 479–483).

FIG. 16 illustrates the F6P-dependence of the Tre6P synthase activity of intact enzyme at different phosphate concentrations. Double-reciprocal plots of these data (not shown) indicate that at 1.3 mM phosphate, and perhaps at 4 mM phosphate, sufficiently high concentrations of F6P completely overcome the inhibition by phosphate. With no added phosphate, F6P caused a maximum activation of 2.5-fold, with a $K_{1/2}$ of 60 μM. At 1.3 mM phosphate, the maximum activation was at least 20-fold, and the $K_{1/2}$ was 1.4 mM F6P. The slopes of these double-reciprocal plots varied linearly with the square of the phosphate concentration, suggesting that two phosphate binding sites are involved. At 4 mM phosphate, which is still within the probable range of phosphate concentrations in yeast cytosol [Lagunas & Gancedo (1983) loc. cit], inhibition was so severe that even 10 mM F6P permitted only 40% of the activity observed under standard conditions. Thus, expression of a truncated trehalose synthase in yeast would be expected to cause a large increase in the intracellular specific activity of the enzyme.

Fructose-1-phosphate, fructose-1,6-bisphosphate, fructose-2,6-bisphosphate and glucose-1-phosphate were tested at sub-optimal F6P concentrations (1 mM F6P at 1.3 mM phosphate). None caused activation at 5 or 2.5 mM concentrations; instead inhibitions of about 25% occurred, probably due to competition with G6P and F6P.

(b) The Tre6Pase Partial Activity

At phosphate concentrations equal to or less than 1 mM, the progress curves of Tre6Pase reactions catalysed by truncated trehalose synthase accelerated markedly over at least the first 10 min of reaction. This did not happen with intact enzyme. For the initial rates of reaction, intact enzyme was activated by smaller phosphate concentrations than was truncated enzyme (FIG. 17). For truncated enzyme, double-reciprocal plots of the activation (vΔ= the rate with phosphate, $v_{pi}$, minus the rate without phosphate, $v_o$) were linear when 1/vΔ was plotted against 1/[phosphate], with a $K_{1/2}$ of 3 mM phosphate. For intact enzyme these plots were non-linear, and linear plots resulted when 1/[phosphate]$^2$ was used (FIG. 18). This, again, suggests that intact enzyme has two strong phosphate binding sites, one of which is lost in the truncated enzyme. For intact enzyme, half maximal activation was obtained at 0.6 mM phosphate.

In the absence of phosphate, F6P did not affect the Tre6Pase activity of intact enzyme. At sub-optimal phosphate concentrations, 5 mM F6P caused modest (20 to 30%) inhibitions of the Tre6Pase activity of both intact and truncated enzymes, and at saturating phosphate concentrations, smaller inhibitions (10 to 15%) were observed (data not shown).

These findings disclose a profound sensitivity of the Tre6P synthase activity of intact trehalose synthase to physiological phosphate and F6P concentrations that is lost by truncation of the 123 kDa long chain to about 85 kDa. The effects of truncation are less marked on the Tre6Pase activities, both enzymes being activated by physiological phosphate concentrations, and neither showing a strong response to F6P. The data suggest that intact enzyme has two strong phosphate binding sites, one of which is located in the region of the 123 kDa long chain removed by truncation. The finding that the 123 kDa long chain could not be recovered from phosphocellulose, disclosed in Example 9 supports this conclusion.

Example 13

Expression of Tre6P synthase activity in *Escherichia coli* cells transformed with TPS1 and TSL1

Figure 20A:
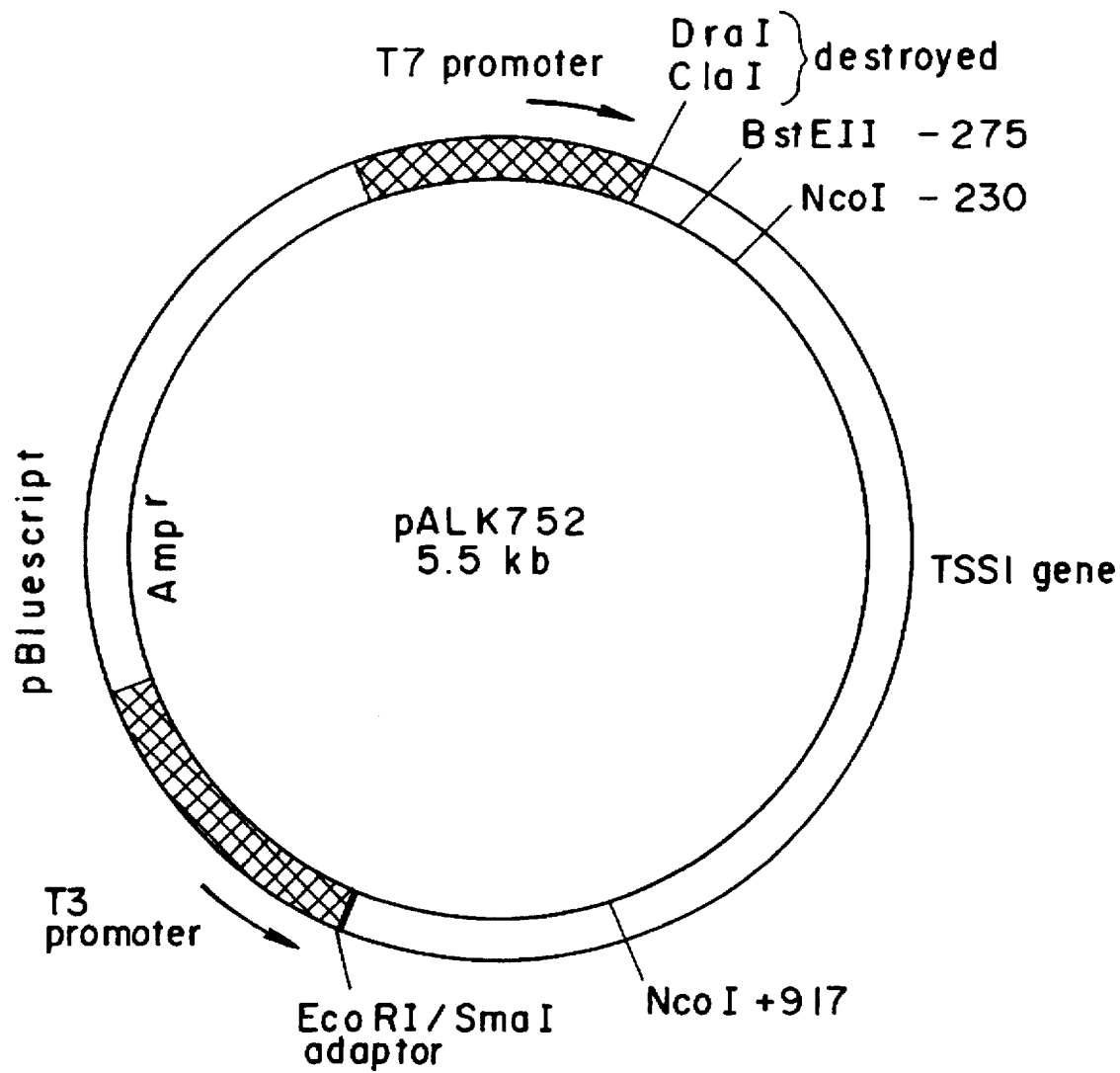
Figure 20B:
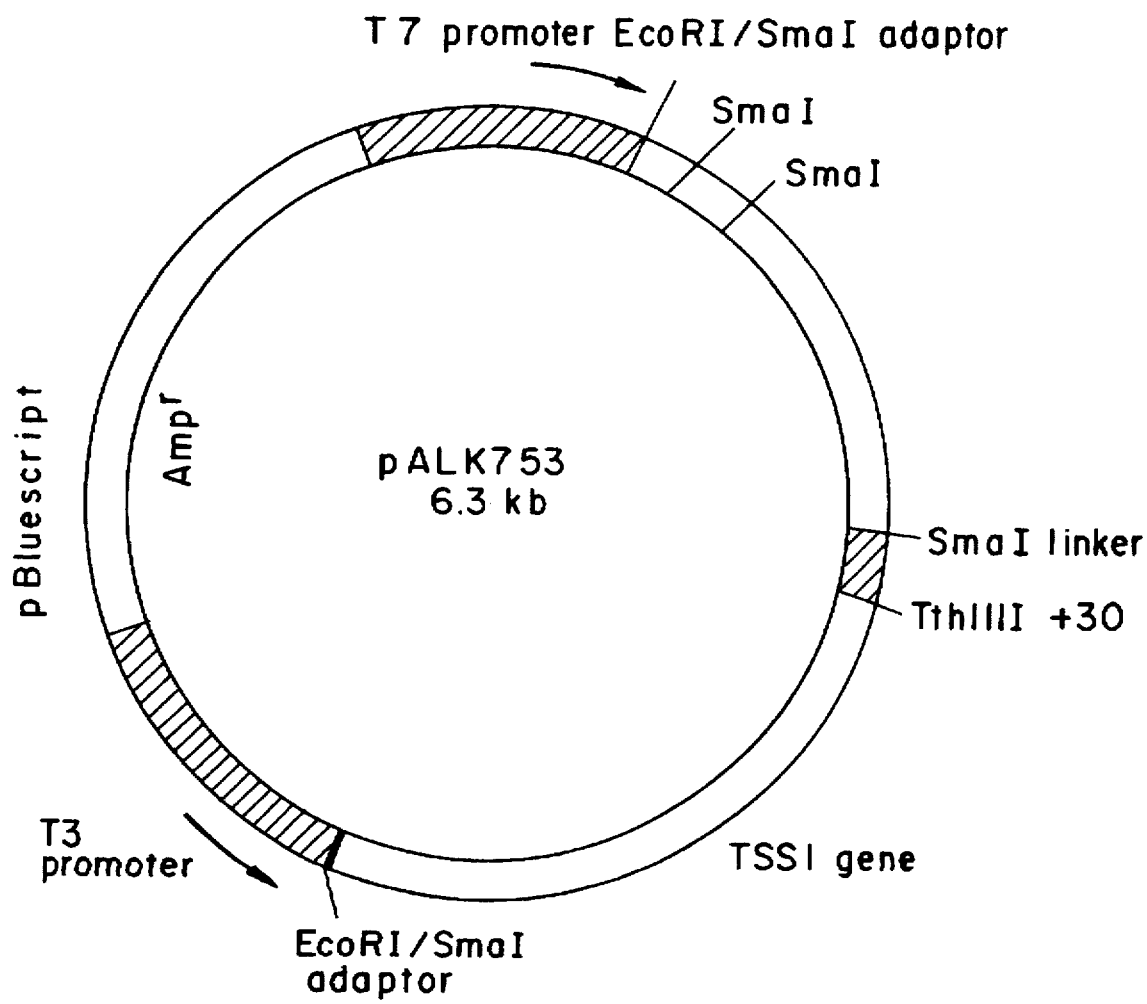
Figure 20C:
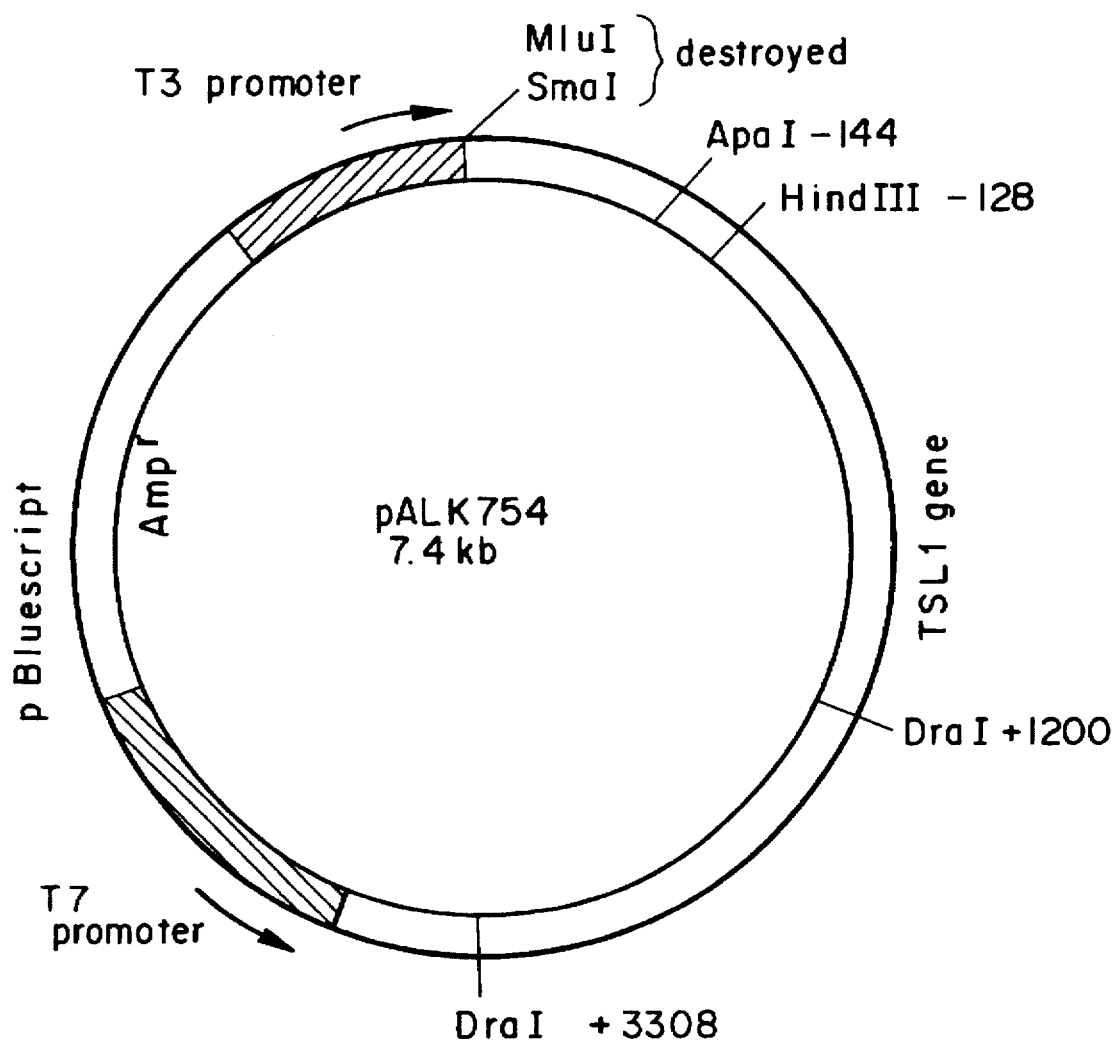

*E.coli*, strain HB101 (ALKO 683) was transformed with the plasmids pALK752 and pALK754 consisting of pBluescript containing TPS1 and TSL1, respectively (see Example 14 and FIGS. 20a and 20c). Transformants ALK03566 and ALK03568 containing, respectively, pALK752 and pALK754 were selected and maintained by growth in the presence of 50 μg/ml of ampicillin. Shake flasks containing Luria Broth with no ampicillin (ALKO 683) or 15 μg/ml ampicillin (ALK03566 and ALK03568) were inoculated with 1 ml of a suspension (A600=1.5) of the appropriate cells and shaken at 250 rpm and 30° C. for 15 h. Cells were harvested (5 min and 3000g), washed twice with water, suspended (1.5 g cells/3.7 ml) in HBMED containing 1 mM PMSF and 10 μg/ml pepstatin A, and broken by two passes through a French press (Aminco) at 15 000 psi. Samples of the homogenates were centrifuged 20 min at 28 000g. Homogenates and supernatants were assayed for Tre6P synthase and Tre6Pase at once and the protein contents of the supernatants were determined (Table 10).

TABLE 10

Expression of Tre6P synthase activity in *E. coli* transformed with TPS1 and TSL1.
Host (ALKO 683) and transformants (ALK03566 containing TPS1 and ALK03568 containing TSL1) were grown, harvested and broken as described in the text. Cell homogenates and supernatants were assayed at once for Tre6P synthase (TPS), using the standard assay and a blank assay from which G6P and F6P were omitted, and for Tre6Pase (TPS). Activities are shown as mU/g fresh cells unless stated otherwise.

|  | ALKO 683 | ALK03566 | ALK03568 |
|---|---|---|---|
| Cell yield (g/200 ml) Homogenates | 1.57 | 1.51 | 1.56 |
| Standard TPS | 361 ± 75 | 1065 ± 118 | 260 ± 23 |
| TPS Blank | 363 ± 57 | 227 ± 45 | 117 ± 77 |
| Net TPS | 0 ± 20 | 840 ± 70 | 140 ± 50 |
| Standard TPP | 1130 ± 70 | 1110 ± 100 | 1190 ± 80 |
| Supernatants |  |  |  |
| Standard TPS | 273 ± 73 | 699 ± 47 | 233 ± 68 |
| TPS Blank | 263 ± 21 | 155 ± 42 | 135 ± 9 |
| Net TPS | 10 ± 50 | 540 ± 10 | 100 ± 60 |
| Net TPS (mU/mg protein) | 0.08 | 4.50 | 0.87 |
| Standard TPP | 1130 ± 100 | 910 ± 90 | 1020 ± 80 |

Standard and blank Tre6P synthase assays both showed accelerating progress curves and results in Table 10 are mean ± range of 5 min and 10 min assays, which were handled separately to calculate the net Tre6P synthase activity. Essentially all of the standard Tre6P synthase activity measured in the host cells and about half of that in ALK03568 cells was due to a blank reaction (presumably a phospho-diesterase) generating UDP from UDPG in the absence of G6P and F6P. The net Tre6P synthase activity of host cells grown under these conditions was close to zero, whereas cells transformed with TPS1 or TSL1 contained 840 or 140 mU/g fresh cells, most of which (64% and 71%, respectively) was soluble. Compared to the host preparation, the specific activities of the net Tre6P synthase in the 28 000 g supernatants were increased about 50-fold (ALK03566) and 10-fold (ALK03568). There are probably two reasons for the very low Tre6P synthase activity of the host cells: trehalose-6-phosphate synthase of *E. coli* is induced by high osmotic strength, and although some strains also acquire activity in stationary phase, the enzyme activity itself is strongly activated by higher (0.25M) cation concentrations than in our assay conditions [Giaever et al (1988) Journal of Bacteriology 170, 2841–2849].

No significant change in the Tre6Pase activities was observed. Host cells already contained 1100 mU/g of Tre6Pase measured in 25 mM phosphate (and more than 5 U/g measured in 25 mM Hepes buffer). If transformation with the plasmids would have generated Tre6Pase activity with a Tre6P phosphatase/synthase ratio the same as in pure trehalose synthase from yeast, then the increments in Tre6Pase (about 250 and 40 mU/g for ALK03566 and ALK03568, respectively) would have been undetectable for ALK03568 and close to the experimental error for ALK03566.

Western analyses (FIG. 19) showed that ALK03566 specifically expressed a 57 kDa band recognized by anti-57K serum and more weakly reacting bands with smaller molecular masses. ALK03568 specifically expressed bands recognized by anti-93K serum at about 60, 36 and 35 kDa (strong), suggesting that extensive degradation of the long chain occurs in ALK03568 or that TSL1 is not correctly transcribed and translated.

These results disclose (1) Tre6P synthase activity can be transferred to heterologous cells by either TPS1 or TSL1, (2) a TPS1 gene product has Tre6P synthase activity and (3) also one or more (degraded) products of TSL1 has Tre6P synthase activity. This latter finding is unexpected, because yeast containing a defective (Example 7) or disrupted (Example 14) TPS1 gene lack Tre6P synthase activity. Possibly ALK03568 accumulates fortuitously degraded proteolytic products of the 123 kDa long chain of trehalose synthase that exhibit Tre6P synthase activity even in the absence of the TPS1 product.

Obviously, transformation with TPS1 (or TSL1) alone can be used to introduce a trehalose synthetic pathway to an organism, such as *E. coli* HB101, that already has the capacity to generate trehalose from trehalose-6-phosphate, possibly via a non-specific phosphatase.

Example 14
Transformation of Yeast
(1) Assembly of complete genes and truncated versions of TSL1

Plasmids comprising the complete ORFs of TPS1 and TSL1 and a truncated ORF of TSL1 were assembled from appropriate immunopositive clones of the HaeIII and EcoRI libraries used in Examples 4 and 5 to sequence these genes:
(a) The TPS1 gene with its promoter (pALK 752)

A 516 bp fragment was cut from HaeIII clone 7 with restriction enzymes DraI and BstEII (see FIG. 6 for restriction sites). The DraI site marks the beginning of the disclosed TPS1 sequence. This fragment was joined to HaeIII clone 20 after this had been digested with BstEII and ClaI (the ClaI site was in the polylinker) and the ClaI end filled with Klenow fragment. The sequence at the junction at the BstEII site in the religated plasmid (shown in FIG. 20a) was confirmed by sequencing.
(b) The TPS1 gene without its promoter (pALK753)

HaeIII clone 21 was cut with the restriction enzyme Tth111I. To this site the following linker (SEQ ID NO:84, synthesized with the ABI DNA Synthesizer) was added:

5'-CGGGAAGACA TAGAACTATG ACTACGGATA
ACGCTAAGGC GCAACTGACC -3'
3'-GCCCTTCTGT ATCTTGATAC TGATGCCTAT
TGCGATTCCG CGTTGACTGG -5'

This includes nucleotides −13 to +33 of TPS1 (see FIG. 4) but, when correctly orientated, introduces a SmaI site at nucleotide −16 from the ATG start site. The plasmid (shown in FIG. 20b) can be used to release with SmaI the ORF of the TPS1 gene and about 200 bp of its terminator for further constructions (e.g. expression vectors containing a new promoter).
(c) The TSL1 gene with its promoter (pALK754)

EcoRI clone 10 was cut with the restriction enzymes MluI and NdeI, and the resulting 4.4 kb fragment was religated into the pBluescript SmaI site. This procedure destroyed all these sites, so that these restriction enzymes cannot be used in further manipulations. The plasmid is shown in FIG. 20c.
(d) The TSL1 gene without its promoter (pALK757)

Primers for the polymerase chain reaction (PCR) were made against the beginning of the TSL1 gene and the sequence at +318. PCR (Techne PHC-2 Heat/Cool Dri-Block®) was used to synthesize (at 55° C.) a 325 bp fragment, which had at one end a SpeI site and close to the other end a BsmI site. This fragment was digested with BsmI and can be ligated to pALK754 after cutting the latter with SpeI (at the site in the pBluescript polylinker) and BsmI and filling the SpeI site with Klenow fragment. For further manipulations, the gene can be isolated by cutting the resulting plasmid with SpeI and, for example, ClaI.
(e) A truncated TSL1 gene A truncated version of TSL1 can be made by cutting pALK754 with StuI and joining the following linker (SEQ ID NO:85) to this site:

5'-GGGCCCAACA ACACAATGGT TACCCCGAAA
TCGAGGGCGG GCAACAGG -3'
3'-CCCGGGTTGT TGTGTTACCA ATGGGGCTTT
AGCTCCCGCC CGTTGTCC -5'

The linker recreates the StuI site and creates a new ATG start codon at +627 in frame with the coding sequence. Thus, this version of the gene encodes a truncated 123 kDa long chain lacking the first 209 amino acids. It was disclosed in Example 10 that removal of the first 325 or so amino acids proceeds without loss of catalytic activity, but releases trehalose synthase from strong inhibition by phosphate and the requirement for F6P. Hence, this construction can encode a truncated 123 kDa polypeptide leading to a trehalose synthase with increased activity at physiological phosphate and F6P concentrations. A new SmaI site is included in the linker. The sequence flanking the new ATG on the 5'-side resembles the original ATG flanking sequence and the surrounding nucleotides are in accordance with the sequences known to occur most frequently at positions −7 to +4.
(2) Disruption mutants.
(a) Disruption of TPS1

The TPS1 gene was disrupted to confirm that it is an essential gene in trehalose synthesis. The one-step gene disruption method [Rothstein, R. J. (1983) Methods in Enzymology 101, 202–211)] was used as follows:

Plasmid pALK752 was cut with XcmI. A blunted SalI-XhoI fragment containing the LEU2 gene from plasmid yEp13 [Broach, J et al (1979) Gene 8, 121-133] was ligated to the blunted XcmI site. The resulting plasmid was cut with NsiI and PvuI and the reaction mixture was run through a 0.8% low-melting point agarose gel. A band of 4 kb was excised from the gel and purified. S. cerevisiae strain S150-2B was transformed (using the one-step alkali-cation method of Chen et al [(1992) Current Genetics 21, 83-84]) with the 4 kb DNA fragment containing the TPS1 gene interrupted by the LEU2 gene. Leu$^+$ transformants were selected on minimal plates lacking leucine and containing glucose or galactose, and the clones obtained were then grown on YPD or YP/2% galactose, respectively.

As expected the phenotype of the disruptants resembled the fdp1 and cif1 phenotypes (see Example 2). Only one transformant (ALK03569) was isolated on glucose and the several transformants isolated on galactose were unable to grow on glucose. The glucose transformant and the tested galactose transformant (ALK03570) did not accumulate trehalose in stationary phase (≦0.2% of dry wt.), lacked Tre6P synthase and had low Tre6Pase activity (≦10% of wild type). The 57 kDa band could not be seen on Western blots. Southern analysis (FIG. 21) showed that the TPS1 gene had been disrupted by a LEU2 gene, but the TSL1 gene was intact.

Another mutant, WDC-3A (see Table 1) with a disrupted TPS1 gene was obtained from the laboratory of Dr. C. Gancedo (Instituto de Investigaciones Biomédicas, CSIC, Madrid, Spain) as a cif1::HIS3 disruptant. This mutant was easier to transform than were the tps1::LEU2 disruptants, and so it was used to confirm that the TPS1 gene on a plasmid can confer Tre6P synthase and Tre6Pase activities, trehalose accumulation and improved stress resistance. WDC-3A was transformed with the plasmid pMB4 (see Table 1; the plasmid contains an intact CIF1 ≡TPS1 gene and a selectable URA3 marker) and transformants selected in the absence of uracil. Western analyses (not shown) indicated that the transformants has acquired the 57 kDa band absent from WDC-3A. The parent and a transformant were grown in parallel in minimal medium containing 2% galactose and (transformant) no uracil or (parent) no uracil. Duplicate cultures of each strain were harvested in early stationary phase after 28 h growth samples taken for studies of stress resistance, and the rest used for trehalose and enzyme assays (Table 11).

TABLE 11

Analysis of WDC-3A and its DMB14 transformant.
Duplicate cultures were analyzed separately for trehalose and combined for enzyme assays. Tre6P synthase (TPS) activities were corrected for UDPGase activity in the absence of G6P and F6P.

|  | WDC-3A (tps1: :HIS3) | pMB14 (TPS1) Transformant |
|---|---|---|
| Cell mass (g/100 ml medium) | 2.6 | 2.8 |
| Trehalose (% of dry wt.) Whole homogenates | 0.84, 0.81 | 2.9, 3.0 |
| Tre6pase (U/g fresh yeast) | 0.02 | 0.84 |
| TPS (U/g fresh yeast) 28,000 g supernatants | 0.84 ± 0.37 | 17.9 ± 3.5 |
| Tre6pase (U/g fresh yeast) | 0.01 | 0.67 |
| TPS (U/G fresh yeast) | 0.22 ± 0.20 | 14.6 ± 3.3 |
| TPS (mU/mg protein) | 4.0 | 223 |

These results disclose that introduction of TPS1 on a plasmid can restore both Tre6P synthase and Tre6Pase activities and increase the trehalose content of an organism. The Tre6P phosphatase/synthase ratio (5%) is much lower than that (about 35%) of purified trehalose synthase whereas the baker' yeast used in Example 1 and the X2180 used in Example 2 both have Tre6P phosphatase/synthase ratios in their homogenates close to that of pure enzyme. This suggests that transformation with TPS1 in pMB14 increases Tre6Pase only up to a limit set by the genetic background of the host (probably the amounts of 99 and 123 kDa polypeptides present) but causes a larger increase in Tre6P synthase due to activity associated also with 57 kDa chains not incorporated into the trehalose synthase complex.

Samples of the transformant and host were frozen in water at 1 µg yeast/ml and kept for 5 days at -20° C. The viability was then tested on plates containing YP/2% galactose. After freezing stress, 1.0±0.1% of the transformants and ≦0.05% of the host cells were viable. These results disclose that transformation of an organism with TPS1 can increase its resistance to freezing-stress.

(b) Disruption of TSL1

Alko provided the laboratory of Johan Thevelein (Lab. voor Moleculaire Celbiologie, Katholieke Universiteit Leuven, Kardinaal Mercierlaan 92, B-3001 Leuven-Heverlee, Belgium) with the TSL1 gene under an agreement dated Sep. 22nd 1992 that recognized this gene as Alko's intellectual property. Standard PCR procedures were used to make an exact deletion of the TSL1 coding sequence and introduce the URA3 gene. A search of the EMBL data base revealed a DNA sequence (accession number M88172) that encodes a polypeptide with 55% identity to the TSL1 product. Because this gene (herein called TPS3) may have a similar function as TSL1, an exact deletion of its ORF was also made and the LEU2 gene introduced by standard PCR procedures. These constructs were used to convert the yeast strain RH144-3A (TSL1 TPS3 ura2 leu2) to the double deletant (tsl1::URA3 tps3::LEU2; called ALK03702), which was then analyzed by the present inventors. Results are shown in Table 12.

TABLE 12

Increased trehalose levels in yeast with deleted TSL1 and TPS3 genes.
RH 144-3A and the tsl1Δ/tps3Δ double deletion mutant were grown for 47 h at 30° C. in YP/2 % glucose and harvested. Duplicate samples were assayed for trehalose. Cells were broken and enzyme activities determined in homogenates as described above but at the indicated phosphate (Pi) concentrations (blanks for Tre6P synthase were run with no G6P or F6P present)

|  | Control Yeast | Double deletant |
|---|---|---|
| Cell mass (mg/ml) | 23.7 | 23.2 |
| Trehalose (% of dw) | 8.0 ± 0.1 | 10.7 ± 0.2 |
| Tre6P Synthase | 12.7 | 3.8 |
| Tre6P Synthase at 4 mM Pi | 6.8 | 3.4 |
| Tre6Pase 25 mM Pi | 3.7 | 1.9 |
| Tre6Pase 2.5 mM Pi | 3.6 | 2.2 |
| Tre6Pase no PI | 0.6 | 2.0 |

These data disclose a method for increasing the trehalose content of baker's yeast by deleting the genes TSL1 and TPS3.

Paradoxically, the standard activities of Tre6P synthase and phosphatase were both lower in the double deletant than in the control yeast, which is consistent with the 123 kDa subunit stabilizing the trehalose synthase complex. However, the synthase was less inhibited by physiological levels of phosphate whereas the phosphatase had lost its requirement for phosphate, which is consistent with the regulatory properties of the 123 kDa subunit disclosed in, especially, Examples 10 and 12. The increased trehalose content of the deletant appears to result from the more efficient activity in vivo of a smaller amount of enzyme. In one embodiment of this invention, the TSL1 gene is replaced by a truncated TSL1, so that favourable regulatory properties are obtained without sacrificing enzyme stability.

(3) Strategies for transformatione

Laboratory strains of S. cerevisiae bearing auxotrophic markers such as his3, leu2, lys 2, trp1 and ura3 can be easily transformed with the trehalose synthase genes by essentially the same methods described for transformation of tps1 disruptants with TPS1. Versions of the genes in which the natural promoters and terminators are intact or have been replaced by (stronger and regulatable) promoters and terminators from other yeast genes can be used. For example, PGKI [pMA91; Mellor et al (1983) Gene 24, 1–14], ADC1 [pAAH5; Ammerer (1983) Methods in Enzymology 101, 192–201] and MEL1 [pALK3537, pALK41, etc., Suominen, P. L. (1988) Doctoral dissertation, University of Helsinki] systems have been used to increase the expression levels of genes in S. cerevisiae and other yeast. The MEL1 system has the advantage that the expression can be regulated, being repressed by glucose and induced by galactose. The use of promoters that can be regulated, for example by adding substances to the growth medium or by changing the temperature, has been described [see, e.g., Mylin et al. (1990) Methods in Enzymology 185, 297–308; Sledziewski et al. (1990) Methods in Enzymology 185, 351–366]. Standard vectors are available [episomal and integrating and centromere yeast plasmids are reviewed by Rose & Broach (1990) Methods in Enzymology 185, 234–279 and Stearns, T., Ma, H & Botstein, D. (1990) Methods in Enzymology 185, 280–291] that incorporate auxotrophic markers such as HIS3, LEU2, TRP1 and URA3, which can be used to select the transformants. Vectors based on these principles, but suited to a particular task can be constructed by a person familiar with the art.

The basic strategy is to leave the yeast with an intact version of its natural genes for trehalose synthase and introduce, either on episomes or integrated into a yeast chromosome, extra copies of the genes. This avoids problems that can be foreseen if all copies of the genes are put under tight control (such as the defects in sugar catabolism expected if TPS1 is not properly expressed; see Example 7.) Transformed yeast bearing additional copies of the genes with their natural promoters may accumulate enough trehalose to exhibit the desired improvement in stability. They may also cycle enough glucose units through trehalose during fermentative conditions to generate an ATPase that accelerates fermentation and increases the yield of ethanol on glucose. Alternatively, the promoters of one or more genes can be changed to promoters that are more active under fermentative conditions. In another aspect of the invention, copies of the ORFs of the genes can be inserted into expression vectors equipped with powerful promoters (that may be regulatable) to cause still larger increases in trehalose. This can be particularly useful for the production of trehalose.

Transforming yeast with two or all three genes can be achieved in several ways. The most obvious procedure is to use different auxotrophic markers and introduce the genes sequentially. Another method is to construct a YIp containing URA3 and a modified version of, say, TSL1 with a stronger promoter but still containing a region of homology upstream of this promoter. After directed integration of this plasmid to the chromosomal ura3 site and selection of URA+transformants, mutants in which the URA3 has again been excised (with a frequency of about $1 \times 10^{-4}$) can be selected by growth on media containing 5-fluoroorotic acid [see Stearns et al. (1990) loc. cit.]. Some of the selected cells would contain a new version of the gene, with the stronger promoter and can again be transformed, this time with, say, a modified TPS1 gene. The resultant transformants will contain one copy of TSL1 driven by the new promoter, and two copies of TPS1, one of which is still under the control of its natural promoter. Thirdly, a YIp containing two or all three genes can be used to introduce the genes in a single step.

The construction of a vector to transform yeast with the coding regions of TPS1 and TSL2 under the control of the constitutive ADC1 promoter exemplifies some of these strategies. A 2.8 kB XbaI-SacI fragment of TSL2 (the XbaI is at +149 and the SacI is in the polylinker) was cut from the YCplac111/TPS2 plasmid and ligated into pBluescript to make pALK727. A primer identical to the TSL2 sequence from −20 to +6 except that it contained a XhoI site at −10 and an adenine at −3 (the preferred nucleotide in this position for high expression in yeast) and another primer identical to +157 to +176 were synthesized and used to make a PCR product comprising the start of TSL2 but with a XhoI site at −10. The XhoI-XbaI fragment was cut from this product and ligated into the XbaI site of pALK727. The XhoI-SacI fragment of the resulting plasmid was ligated into the HindIII site between the ADC1 promoter and terminator of pAAH5 to give pALK729. This plasmid can be used to transform leu⁻ yeast to introduce the TSL2 gene encoding the Tre6Pase subunit under a constitutive promoter.

The 1.7 kB SmaI fragment of pALK753 containing the TPS1 ORF and about 15 upstream bases was similarly ligated into the HindIII site of pAAH5 to give pALK731. A 3.5 kB BamI fragment of pALK731 containing TPS1 between the ADC1 promoter and terminator was then ligated into the unique StuI site of pALK729 to make pALK732, which contains genes for both Tre6P synthase and phosphatase subunits driven by ADC1 promoters. EcoRI restriction analysis was used to distinguish the product (pALK732/21: 7.0, 5.5, 5.0 and 1.0 kB fragments) with TPS1 and TSL2 in opposite orientation from that (pALK732/22: 7.0, 5.5, 3.5 and 2.5 kB fragments) where they have the same orientation.

RH144 and S150 strains of Sacch. cerevisiae were transformed with pALK732. Table 13 shows that the RH144 transformants contained more trehalose during fermentation and also in the stationary phase. The data underestimate the effect of pALK732 on trehalose levels during fermentation because the transformants were harvested earlier (at a residual glucose of 1%) when less trehalose is expected than in the untransformed yeast (harvested at 0.6% glucose).

TABLE 13

Increased trehalose levels in yeast transformed with pALK732.
RH144 was grown on a minimal medium containing all essential amino acids and 2% glucose. The transformants were grown on the same medium lacking leucine.

|  | Untransformed | pALK732/21 | pALK732/22 |
|---|---|---|---|
| During fermentation |  |  |  |
| Residual glucose (%) | 0.61 | 1.05 | 0.97 |
| Trehalose (µg/mg wet wt.) | 0.86 | 3.1 | 3.0 |
| Stationary cells |  |  |  |
| Trehalose (µg/mg wet wt.) | 2.2 | 10.1 | 12.0 |

Figure 22:
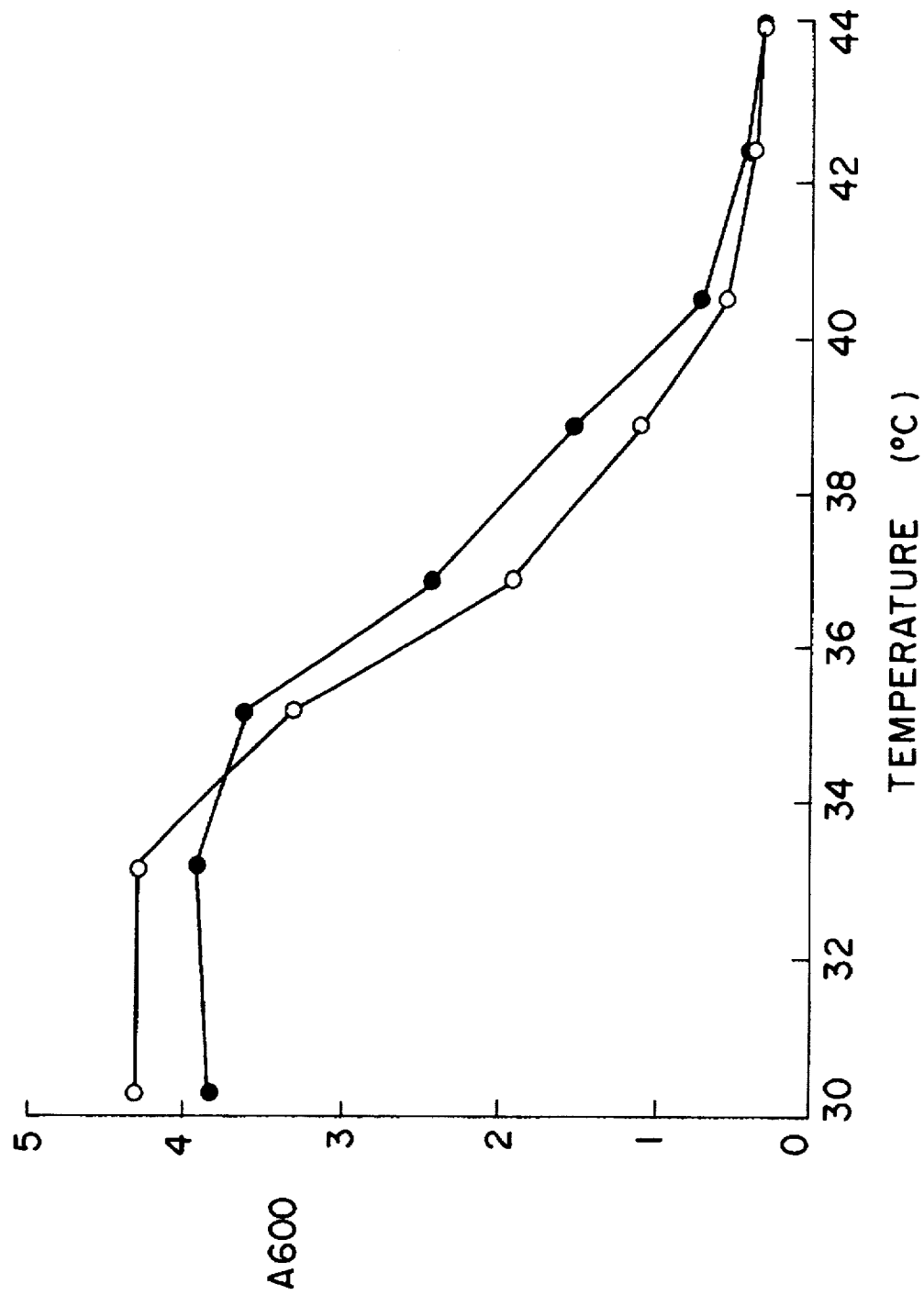

FIG. 22 shows that when the yeast was grown in 5 ml lots of the media described in Table 13 in screw-capped tubes in a temperature gradient block. S150 yeast transformed with pALK732/21 grew to a higher cell density at 38° C. than did the untransformed yeast. Under these conditions the growth is essentially fermentative. The results disclose that transformation of yeast with TPS1 and TSL2 under ADC1 promoters increases the temperature tolerance during fermentative growth.

The 2μ origin of replication in pALK732 can be destroyed by digestion with NsiI, which excises an about 1 kB fragment, leaving the rest of the plasmid functional. The resulting plasmid contains a unique StuI site within the TPS1 coding sequence, and so can be linearized with StuI and used for targetted integration at the resident TPS1 gene.

These examples illustrate how the genes encoding trehalose synthase subunits can be manipulated, their promoters changed, different genes carried in the same vector and used to transform yeast using self-replicating plasmids or by integration into the genome. Other approaches could be used and are obvious to a person skilled in the art.

Various methods to transform industrial, polyploid yeast, which lack auxotrophic markers have been described in the literature. Earlier methods have been reviewed by Knowles, J. K. C. & Tubb, R. S. [(1987) E.B.C. symposium on brewer's yeast, Helsinki, 1986. Monograph XII 169–185] and include the use of marker genes that confer resistance to antibiotics, methylglyoxal, copper, cinnamic acid and other compounds. These markers facilitate selection of transformants. Some of the marker genes are themselves of yeast origin, and so are preferred for acceptability reasons. When suitable modifications and combinations of the genes have been identified by using laboratory yeast, they may be transferred to industrial yeast using these procedures or others described in the literature, such as co-transformation with pALK2 and pALK7 [Suominen, P. I. (1988) loc. cit.]. These plasmids contain a readily selectable MEL1 marker gene on a 2 μ-based plasmid that can readily be cured, thus facilitating sequential transformation with more than one gene if it is not practicable to introduce the modified genes in one step using this co-transformation procedure.

The plasmid pALK733 is an example of a vector suitable for industrial yeast. This was constructed by ligating a 2.8 kB BamI-SalI fragment containing the MelI gene into the XhoI site of pALK732. It thus contains TPS1 and TSL2 with ADC1 promoters and the Mel1 gene for selection in most ordinary industrial strains of baker's and distiller's yeasts. Based on the results disclosed above in Tables 12 and 13, transformation of industrial strains with this plasmid is expected to cause trehalose production during the fermentative stage and also to increase stationary phase trehalose levels, without the necessity of simultaneously introducing TSL1. However, for certain applications, cotransformation with a complete or truncated TSL1 gene is envisaged to cause further improvements.

Example 15

Trehalose production by plants transformed with the TPS1 gene under the ATS1A promoter The plants used were *Nicotiana tabacum* cv. SR1 and *Arabidopsis thaliana* L. Heynh. ecotype C-24.

To construct a chimeric ATS1A-TPS1 gene the ATS1A promoter fragment, lacking the sequence for the transit peptide, was amplified by PCR from the plasmid pGSFR401. Synthetic olignucleotide primers were used to create an EcoRI site at the 5' end and an XbaI site at the 3' end of the amplified fragment. The PCR amplification product was digested with the appropriate restriction enzymes and, following purification on an agarose gel, ligated into an EcoRI and MluI digested pUC19 plasmid.

The yeast TPS1 gene was amplified from the plasmid pALK752 described above. The resulting fragment contained 5' MluI and 3' XbaI sites. After digestion and purification the fragment was ligated behind the pATS1A in pUC19. A fragment with the promoter-TPS1 construct was cut out with EcoRI and XbaI and then inserted into a pBluescriptII SK$^+$ (Stratagene) derived plasmid carrying the 3' end of the T-DNA gene G7 including its polyadenylation signal and the T-DNA right border. Finally, the entire chimeric gene was inserted as an EcoRI-SacI fragment into the plant transformation vector pDE1001 (Denecke et al. [1992] EMBO J. 11, 2345–2355) containing the chimeric kanamycin resistance gene pNOS-NEO-3' OCS as a selective marker. This resulted in the plasmid pKOH51 carrying the chimeric pATS1A-TPS1-3'G7 gene (FIG. 23). Constructions were cloned into the bacterial strain, *E. coli* DH5α by transformation, and then transferred by electroporation (Dower et al. [1988] Nucl. Acids Res. 16, 6127–6145) to *Agrobacterium tumefaciens* (C58C1rif®) containing the non-oncogenic Ti plasmid pGV2260 (Deblare et al. [1985] Nucl. Acids Res. 13, 2777–2778).

Growth of plant material

For axenic growth, sterilised explants from *Nicotiana tabacum* (SR1) were planted in glass jars containing solidified MS (Murashige & Skoog [1962] Physiol. Plant 15, 473–497) medium supplemented with 2% sucrose (MS-2). These jars were then placed in a controlled growth environment in a culture chamber where plants were allowed to grow at 22° C. with a 16 h photoperiod. Explants were regularly transferred to new jars and MS-2 medium for a continuous growth of axenic material. Greenhouse plants were grown in soil in pots and watered daily. Transformed *A. thaliana* plants were first grown axenically in baby-food jars in a controlled environment as described for tobacco above, but were later transferred to soil in pots in the greenhouse for seed production. Seeds from the primary transformants were either directly planted in soil for new seed production or surface sterilized and grown axenically in 24-well tissue culture plates for molecular analysis.

Plant transformation

Tobacco and *A. thaliana* were both transformed according to the following protocol, with starting material being excised leaves of tobacco and roots of *A. thaliana*. The transformation and tissue culture were essentially as described by Valvekens et al ([1988] Proc. Natl. Acad. Sci. U.S.A. 85, 5536–5540) with the following modifications. Isolated roots or leaves were preincubated on solidified callus-inducing medium (CIM) for 4 days, roots were cut into small segments (1–2 mm) and leaves were cut into larger pieces (10–20 mm) and transferred into 20 ml liquid CIM. 3',5'-Dimethoxy-4' hydroxyacetophenone was added (0.2 mg/l) prior to Agrobacterium (C58C1rif$^R$) infection. The bacteria used for infection were propagated overnight in YEB medium (Vervliet et al. [1975] J. Gen. Virol. 26, 33–48) containing appropriate antibiotics at 28° C., and collected by centrifugation. The bacterial pellet was then resuspended in 10 mM MgSO4, added to the plant tissue and mixed gently for about 15 min. Excess liquid was poured off and the roots blotted on sterile filter paper. After co-cultivation for 2 days on solid CIM, the plant tissue was rinsed 3–4 times with liquid CIM to wash off bacteria, and transferred to selective shoot induction medium (SIM). After 7 days of growth, explants with differentiated morphogenic sectors were transferred to fresh SIM.

Tobacco transformants containing the yeast gene (TPS1) for the Tre6P synthase subunit under the ATS1A promoter were grown up both in sterile, "in vitro", conditions and in a greenhouse. Mature plants had no obvious phenotype compared to the untransformed controls or controls transformed with the vector pDE1001 (lacking TPS1). Leaves were collected at 0900 h, frozen and stored at or below −70° C. prior to analysis.

FIG. 24 shows that the transgenic plants expressing the chimeric ATS1A-TPS1 gene produce a 56 kDa polypeptide recognized by antiserum prepared against the 56 kDa subunit of yeast trehalose synthase. Table 14 summarizes the trehalose contents of the leaves.

TABLE 14

Trehalose contents of TPS1-transformants of tobacco

| Tobacco Plant | Special Treatment | Trehalose (mg/g fresh leaf) |
| --- | --- | --- |
| In vitro plants | | |
| Untransformed SR1 | — | ≦0.002 |
| pDE1001 Control | — | ≦0.002 |
| Transformant 1 | — | 0.02 |
| Transformant 3 | — | 0.009 |
| Transformant 4 | — | 0.067 |
| Transformant 8 | — | 0.075 |
| Transformant 8 | Ethanol extraction instead of water | 0.055 |
| Greenhouse plants | | |
| pDE1001 Control | — | ≦0.002 |
| Transformant 1 | — | 0.16 |
| Transformant 4 | — | 0.16 |
| Transformant 4 | Alkaline phosphatase* | 0.13 |
| Transformant 5 | — | 0.052 |
| Transformant 6 | — | 0.044 |
| Transformant 8 | — | 0.039 |
| Transformant 8 | Specific trehalase | 0.021 |
| Transformant 19 | — | 0.053 |
| Transformant 19 | Alkaline phosphatase* | 0.060 |
| Transformant 19 | Specific trehalase | 0.016 |
| Transformant 25 | — | 0.036 |
| Transformant 26 | — | 0.11 |

*The extract was treated with alkaline phosphatase under conditions such that carrier [$^{14}$C] trehalose 6-phosphate was dephosphorylated.

These results disclose that the yeast TPS1 gene is efficiently expressed in tobacco when its promoter is replaced by the ATS1A promoter. The specific signal observed on Western blots has the correct molecular weight. The strongest signals (e.g., that from Transformant 4 grown in vitro) were only slightly weaker per unit of protein applied to the gel than the signals obtained from stationary phase yeast. Expression of TPS1 was accompanied by the appearance of trehalose in the leaf tissue, identified both by its HPLC behaviour and by the fact that it was degraded by a highly specific trehalase (see also FIG. 25). Different transformants expressed the TPS1 product to different levels for reasons that have not yet been established, and (with the apparent exception of Transformant 8) the amount of trehalose found in the leaves roughly correlated with the strength of the 56 kDa signal in the Westerns (compare FIG. 24 with Table 14). Although these transformants did not carry a gene encoding a microbial trehalose-6-phosphatase, no evidence was found that the plants accumulated more trehalose-6-phosphate than trehalose.

The results also disclose that tobacco plants expressing TPS1 under the ATS1A promoter and accumulating trehalose in their green tissues during daylight are healthy and normal in appearance.

On a protein basis, the trehalose contents of the best transformants in Table 14 (e.g.≧16 mg/g protein for Transformant 4) are already at least 20% of the level at which a clear improvement in thermotolerance is observed in yeast (De Virgilio et al [1990] FEBS Letters 273, 107–110).

Some TPS1-transformants and controls were assayed for Tre6P synthase activity. Results are shown in Table 15.

Results in Table 15 are means ± the extreme range from duplicate zero and 15 or 30 min assays. For the controls, Tre6P synthase activity did not differ from zero. For Transformant 4, an acid- and alkali-stable carbohydrate accumulated in the presence of UDPG and glucose 6-phosphate. This accumulation required glucose 6-phosphate, but not fructose 6-phosphate and was prevented when UDPG was replaced by ADPG. The accumulated carbohydrate is presumably trehalose or trehalose 6-phosphate, because other possible products are destroyed by the hydrolyses. HPLC analysis showed it was not trehalose. Thus, trehalose 6-phosphate is synthesized by extracts of Transformant 4 much faster than it is converted to trehalose. This shows that the overall rate of trehalose synthesis in the leaves will be increased by cotransformation with TSL2, which encodes the Tre6Pase subunit.

The Tre6P synthase activity of yeast extracts found by the method used in Table 15 agreed with that found by measuring the appearance of UDP as described by Londesborough & Vuorio ([1991] J. Gen. Microbiol. 137, 323–330). Furthermore, yeast extracts measured in the presence of extracts of tobacco plants were not inhibited. Thus, the absence of activity in the control plants in Table 15 is not due to interference by some factor present in tobacco extracts.

TABLE 15

Tre6P synthase activity of TPS1-transformed and control tobacco leaves (All results are with plants grown in vitro).

| | | Tre6P Synthase Activity (mU/g fresh leaf) | |
| --- | --- | --- | --- |
| Transformant | Assay Mixture | 15 min | 30 min |
| Untransformed Control | Complete | 3 ∓ 47 | 3 ∓ 21 |
| PDE1001 Control | Complete | 22 ∓ 35 | 7 ∓ 8 |
| Transformant 4, Expt. 1 | Complete | 259 ∓ 147 | 60 ∓ 6 |
| Transformant 4, Expt. 2 | Complete | 128 ∓ 39 | 155 ∓ 22 |
| | Less Glu6P | 12 ∓ 19 | −1 ∓ 12 |
| | Less Fru6P | 153 ∓ 10 | 144 ∓ 3 |
| | ADPG instead of UDPG | 0 ∓ 52 | 4 ∓ 21 |

The Tre6P synthase activity found in Transformant 4 was labile. With some extracts, the activity disappeared during a few hours storage on ice. However, the specific band seen in Western analyses was still present at nearly its original strength in extracts stored for 24 h at room temperature. Thus, it is probable that the conformation of the Tre6P synthase subunit changes during storage of tobacco extracts. These results indicate that increased Tre6P synthase activity will be achieved by transforming the tobacco simultaneously with TPS1 and one or more of the other subunits of yeast trehalose synthase, thereby increasing the conformational stability of the Tre6P synthase subunit.

Arabidopsis plants containing TPS1 under the ATS1A promoter were constructed in the same way as the tobacco transformants described above. These transformed Arabidopsis plants are also healthy and normal in appearance and produced fertile seed. It is expected that they will contain the 56 kDa subunit of yeast trehalose synthase and accumulate trehalose in their green tissues.

Example 16

Trehalose production by plants co-transformed with the yeast TPS1 gene and yeast TSL1 or TSL2 genes A person skilled in the art can prepare vectors containing the coding sequences of the yeast genes TSL1 and TSL2

51 under the control of the ATS1A promoter and use them to transform tobacco, Arabidopsis and other plants by the methods described in Example 15. Plants simultaneously transformed with TPS1 and one or both of the other genes, TSL1 and TSL2, can be obtained by cross-breeding of individual transformants, by further transformation of one transformed plant with a second gene, or by transformation with vectors containing two or three of the genes linked to appropriate promoters: for example, TPS1 can be linked to the non-constitutive ATS1A promoter, to provide control over trehalose synthesis, and the other gene(s) driven by constitutive promoters.

It is expected that the controlled expression of genes for two or more subunits of the yeast trehalose synthase complex, at least one being the 56 kDa subunit, will result in increased accumulation of trehalose in the plant, because the 56 kDa subunit will be stabilized by the presence of the other subunit(s). Furthermore, introduction of the 102 kDa, Tre6Pase subunit will be beneficial because it will decrease the potential accumulation of trehalose 6-phosphate expected when the stability of the Tre6P synthase subunit is increased.

52

Example 17

Transformation of plants with genes for trehalose synthase under the control of stress-induced promoters Plant promoters, such as LTI78 (Nordin et al |1993| Plant Mol. Biol. 21, 641–653) and RAB18 (Lång & Palva |1992| Plant Mol. Biol. 20, 951–962), are known that are induced in response to drought and cold stress. By transforming tobacco, Arabidopsis and other plants with TPS1 alone or preferably together with TSL1 and TSL2 the accumulation of trehalose in plant tissues can be made to occur only in response to these stresses. Other microbial genes encoding components of trehalose synthase can also be used. The advantage is that levels of trehalose that might be deleterious to certain tissues of certain plants and which can also represent a yield-decreasing diversion of photo-synthetic capacity, would accumulate only (1) when the plant is exposed fortuitously to stress (the benefits of the protection afforded by the trehalose then overcoming any deleterious effects) or (2) when the plant is deliberately exposed to stress in order to cause the accumulation of trehalose which will then be extracted from the harvested plant.

We claim:

1. A plant transformed with at least one DNA comprising the coding sequence of a microbial gene for a component of trehalose synthase fused in correct reading frame to a plant promoter.

2. The plant of claim 1 wherein the plant promoter is non-constitutive, so that full expression of the microbial gene is not realized until the plant is mature or encounters specific environmental conditions.

3. The plant of claim 2 wherein the plant promoter is tissue specific.

4. The plant of claim 2 wherein the plant promoter is light-induced.

5. The plant of claim 2 wherein the plant promoter is stress-induced.

6. The plant of any one of claims 1, 2, 3, 4 or 5 wherein the transforming DNA is selected from the group consisting of SEQ ID NOS: 1, 3, and 83 and DNA encoding polypeptide chains having the amino acid sequence of SEQ ID NOS: 2, 4, 29–38, and 44–49.

7. The plant according to claim 6 wherein the gene is yeast gene TPS1 and the plant promoter is ATS1A.

8. The plant of claim 5 wherein the plant promoter is LTI78 or RAB18.

9. The plant according to claim 1 wherein the plant is more tolerant of stresses such as water-deprivation, heat or cold than is the untransformed plant.

10. The plant of according to claim 9 which is monocotyledonous such as corn, oats, millet, wheat, rice, barley, sorghum, amaranth, onion, asparagus and sugar cane.

11. The plant of any of claims 1 to 9 which is dicotyledonous such as alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea and coffee.

12. The production of trehalose from the plant according to claim 1.

13. A seed produced by the plant of any of according to claim 1.

14. A method of increasing the trehalose content of plants, comprising transforming a plant with at least one DNA encoding a component of trehalose synthase expressed under the control of a suitable promoter to produce a transgenic plant.

15. The method according to claim 14 wherein the suitable promoter allows temporal or topological control over the expression.

16. The method of claim 14 or 15 wherein said at least one DNA is selected from the group consisting of SEQ ID NOS: 1, 3, and 83 and DNA encoding polypeptide chains having the amino acid sequence of SEQ ID NOS: 2, 4, 29–38 and 44–49.

17. The method of claim 16 wherein the plants are co-transformed with the TPS1 gene under the control of a non-constitutive promoter ATS1A and one or both of the genes TSL1 and TSL2 are under the control of appropriate promoters.

18. The method according to claim 14 wherein the coding sequence of at least one microbial gene encoding at least one component of trehalose synthase is fused to a plant promoter that causes expression specifically in storage organs.

19. A method of producing trehalose, which comprises cultivating the transgenic plant of any of according to claim 14 under conditions that induce the synthesis of trehalose in the plant and then extracting the trehalose from the tissues of the plant.

20. The method of claim 19 wherein the transgenic plant accumulates trehalose in a storage organ.

21. The method of claim 20 wherein the transgenic plant is a root crop such as potato, sugarbeet and turnip.

22. A method of protecting staple crops against drought, which comprises transforming a plant with the coding sequence of at least one microbial gene for at least one component of trehalose synthase fused appropriately to a plant promoter so that full expression of the microbial gene is not realized until the plant encounters conditions of drought.

23. A method of protecting plants including those producing berries or fruits against frost damage to thermally sensitive tissues, which comprises transforming the plant with the coding sequence of at least one microbial gene for at least one component of trehalose synthase fused appropriately to a plant promoter so that full expression of the microbial gene is not obtained until the plant encounters conditions conducive to frost.

* * * * *

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
        ( A ) LENGTH: 2481 base pairs
        ( B ) TYPE: Nucleotide
        ( C ) STRANDEDNESS: Doublestranded
        ( D ) TOPOLOGY: Linear ( i i ) MOLECULE TYPE: Genomic DNA ( i i i ) HYPOTHETICAL: no ( i v ) ANTI-SENSE: no ( v i ) ORIGINAL SOURCE:
        ( A ) ORGANISM: Saccharomyces cerevisiae
        ( B ) STRAIN: S288C
        ( E ) HAPLOTYPE: Haploid ( v i i ) IMMEDIATE SOURCE:
        ( A ) LIBRARY: Genomic
        ( B ) CLONE: 20

( v i i i ) POSITION IN GENOME:
        ( A ) CHROMOSOME/SEGMENT: 2R ( x i ) SEQUENCE DESCRIPTION: SEQ ID NO:1:

```
TTTTTAAACG  TATATAGATG  TCTACATGTG  TGTTTTTGTT  TTTTTACGTA           50

CGTATACCCA  CCTATATATG  CATAATCCGT  AATTGAAAAA  AAAAAAAGTA          100

AAGATCAAGG  AACACATCAC  CCTGGGCACA  TCAAGCGTGA  GGAATGCCGT          150

CCAACTGGTG  GAGACGCTTG  ATTTGCTCTT  TTTGTTCCTG  GGTCCAACCC          200

GGTCTCGAAG  AACATCAGCA  CCACGCCCGC  AACGACAAAG  AACATTGCAA          250

TACACTTGCA  TATGTGAGCA  TAGTCGAGCG  GTCCGTTCTG  TGGTTGATGC          300

TGTTGTTCTT  TCTTCTGTTT  GTCAGGGGTG  ATAGCCATAT  CTTCGTGCTC          350

TTGTTGCGAT  TGTTCTGTTC  CATCTGCACC  AGAACAAAGA  ACAAAAGAAC          400
```

| | | | | |
|---|---|---|---|---|
| AAGGAACAAA | GTCCAAGCAC | GTCAGCGCTG | TTTATAAGGG | GATTGACGAG | 450
| GGATCGGGCC | TAGAGTGCCA | GCGCGCCAGG | GAGAGGGAGC | CCCCTGGGCC | 500
| CTCATCCGCA | GGCTGATAGG | GGTCACCCCG | CTGGGCAGGT | CAGGGCAGGG | 550
| GCTCTCAGGG | GGGCGCCATG | GACAAACTGC | ACTGAGGTTC | TAAGACACAT | 600
| GTATTATTGT | GAGTATGTAT | ATATAGAGAG | AGATTAAGGC | GTACAGCCGG | 650
| GTGGTAGAGA | TTGATTAACT | TGGTAGTCTT | ATCTTGTCAA | TTGAGTTTCT | 700
| GTCAGTTTCT | TCTTGAACAA | GCACGCAGCT | AAGTAAGCAA | CAAAGCAGGC | 750
| TAACAAACTA | GGTACTCACA | TACAGACTTA | TTAAGACATA | GAACTATGAC | 800
| TACGGATAAC | GCTAAGGCGC | AACTGACCTC | GTCTTCAGGG | GGTAACATTA | 850
| TTGTGGTGTC | CAACAGGCTT | CCCGTGACAA | TCACTAAAAA | CAGCAGTACG | 900
| GGACAGTACG | AGTACGCAAT | GTCGTCCGGA | GGGCTGGTCA | CGGCGTTGGA | 950
| AGGGTTGAAG | AAGACGTACA | CTTTCAAGTG | GTTCGGATGG | CCTGGGCTAG | 1000
| AGATTCCTGA | CGATGAGAAG | GATCAGGTGA | GGAAGGACTT | GCTGGAAAAG | 1050
| TTTAATGCCG | TACCCATCTT | CCTGAGCGAT | GAAATCGCAG | ACTTACACTA | 1100
| CAACGGGTTC | AGTAATTCTA | TTCTATGGCC | GTTATTCCAT | TACCATCCTG | 1150
| GTGAGATCAA | TTTCGACGAG | AATGCGTGGT | TCGGATACAA | CGAGGCAAAC | 1200
| CAGACGTTCA | CCAACGAGAT | TGCTAAGACT | ATGAACCATA | ACGATTTAAT | 1250
| CTGGGTGCAT | GATTACCATT | TGATGTTGGT | TCCGGAAATG | TTGAGAGTCA | 1300
| AGATTCACGA | GAAGCAACTG | CAAAACGTTA | AGGTCGGGTG | GTTCCTGCAC | 1350
| ACACCATTCC | CTTCGAGTGA | AATTTACAGA | ATCTTACCTG | TCAGACAAGA | 1400
| GATTTTGAAG | GGTGTTTTGA | GTTGTGATTT | AGTCGGGTTC | CACACATACG | 1450
| ATTATGCAAG | ACATTTCTTG | TCTTCCGTGC | AAAGAGTGCT | TAACGTGAAC | 1500
| ACATTGCCTA | ATGGGGTGGA | ATACCAGGGC | AGATTCGTTA | ACGTAGGGGC | 1550
| CTTCCCTATC | GGTATCGACG | TGGACAAGTT | CACCGATGGG | TTGAAAAAGG | 1600
| AATCCGTACA | AAAGAGAATC | CAACAATTGA | AGGAAACTTT | CAAGGGCTGC | 1650
| AAGATCATAG | TTGGTGTCGA | CAGGCTGGAT | TACATCAAAG | GTGTGCCTCA | 1700
| GAAGTTGCAC | GCCATGGAAG | TGTTTCTGAA | CGAGCATCCA | GAATGGAGGG | 1750
| GCAAGGTTGT | TCTGGTACAG | GTTGCAGTGC | CAAGTCGTGG | AGATGTGGAA | 1800
| GAGTACCAAT | ATTTAAGATC | TGTGGTCAAT | GAGTTGGTCG | GTAGAATCAA | 1850
| CGGTCAGTTC | GGTACTGTGG | AATTCGTCCC | CATCCATTTC | ATGCACAAGT | 1900
| CTATACCATT | TGAAGAGCTG | ATTTCGTTAT | ATGCTGTGAG | CGATGTTTGT | 1950
| TTGGTCTCGT | CCACCCGTGA | TGGTATGAAC | TTGGTTTCCT | ACGAATATAT | 2000
| TGCTTGCCAA | GAAGAAAAGA | AAGGTTCCTT | AATCCTGAGT | GAGTTCACAG | 2050
| GTGCCGCACA | ATCCTTGAAT | GGTGCTATTA | TTGTAAATCC | TTGGAACACC | 2100
| GATGATCTTT | CTGATGCCAT | CAACGAGGCC | TTGACTTTGC | CCGATGTAAA | 2150
| GAAAGAAGTT | AACTGGGAAA | AACTTTACAA | ATACATCTCT | AAATACACTT | 2200
| CTGCCTTCTG | GGGTGAAAAT | TTCGTCCATG | AATTATACAG | TACATCATCA | 2250
| AGCTCAACAA | GCTCCTCTGC | CACCAAAAAC | TGATGAACCC | GATGCAAATG | 2300
| AGACGATCGT | CTATTCCTGG | TCCGGTTTTC | TCTGCCCTCT | CTTCTATTCA | 2350
| CTTTTTTTAT | ACTTTATATA | AAATTATATA | AATGACATAA | CTGAAACGCC | 2400

```
ACACGTCCTC TCCTATTCGT TAACGCCTGT CTGTAGCGCT GTTACTGAAG       2450

CTGCGCAAGT AGTTTTTTCA CCGTATAGGC C                           2481
```

( 2 ) INFORMATION FOR SEQ ID NO:2:

( i ) SEQUENCE CHARACTERISTICS:
        ( A ) LENGTH: 495 amino acids
        ( B ) TYPE: amino acid
        ( D ) TOPOLOGY: linear ( i i ) MOLECULE TYPE: Polypeptide ( i i i ) HYPOTHETICAL: Yes ( x i ) SEQUENCE DESCRIPTION:SEQ ID NO:2:

```
Met Thr Thr Asp Asn Ala Lys Ala Gln Leu Thr Ser Ser Ser Gly
                 5                  10                   15

Gly Asn Ile Ile Val Val Ser Asn Arg Leu Pro Val Thr Ile Thr
                20                  25                   30

Lys Asn Ser Ser Thr Gly Gln Tyr Glu Tyr Ala Met Ser Ser Gly
                35                  40                   45

Gly Leu Val Thr Ala Leu Glu Gly Leu Lys Lys Thr Tyr Thr Phe
                50                  55                   60

Lys Trp Phe Gly Trp Pro Gly Leu Glu Ile Pro Asp Asp Glu Lys
                65                  70                   75

Asp Gln Val Arg Lys Asp Leu Leu Glu Lys Phe Asn Ala Val Pro
                80                  85                   90

Ile Phe Leu Ser Asp Glu Ile Ala Asp Leu His Tyr Asn Gly Phe
                95                 100                  105

Ser Asn Ser Ile Leu Trp Pro Leu Phe His Tyr His Pro Gly Glu
                110                115                  120

Ile Asn Phe Asp Glu Asn Ala Trp Phe Gly Tyr Asn Glu Ala Asn
                125                130                  135

Gln Thr Phe Thr Asn Glu Ile Ala Lys Thr Met Asn His Asn Asp
                140                145                  150

Leu Ile Trp Val His Asp Tyr His Leu Met Leu Val Pro Glu Met
                155                160                  165

Leu Arg Val Lys Ile His Glu Lys Gln Leu Gln Asn Val Lys Val
                170                175                  180

Gly Trp Phe Leu His Thr Pro Phe Pro Ser Ser Glu Ile Tyr Arg
                185                190                  195

Ile Leu Pro Val Arg Gln Glu Ile Leu Lys Gly Val Leu Ser Cys
                200                205                  210

Asp Leu Val Gly Phe His Thr Tyr Asp Tyr Ala Arg His Phe Leu
                215                220                  225

Ser Ser Val Gln Arg Val Leu Asn Val Asn Thr Leu Pro Asn Gly
                230                235                  240

Val Glu Tyr Gln Gly Arg Phe Val Asn Val Gly Ala Phe Pro Ile
                245                250                  255

Gly Ile Asp Val Asp Lys Phe Thr Asp Gly Leu Lys Lys Glu Ser
                260                265                  270

Val Gln Lys Arg Ile Gln Gln Leu Lys Glu Thr Phe Lys Gly Cys
                275                280                  285

Lys Ile Ile Val Gly Val Asp Arg Leu Asp Tyr Ile Lys Gly Val
                290                295                  300

Pro Gln Lys Leu His Ala Met Glu Val Phe Leu Asn Glu His Pro
                305                310                  315
```

| | | | | | | | | | | | | | | |
|---|---|---|---|---|---|---|---|---|---|---|---|---|---|---|
|Glu|Trp|Arg|Gly|Lys<br>320|Val|Val|Leu|Val|Gln<br>325|Val|Ala|Val|Pro|Ser<br>330|
|Arg|Gly|Asp|Val|Glu<br>335|Glu|Tyr|Gln|Tyr|Leu<br>340|Arg|Ser|Val|Val|Asn<br>345|
|Glu|Leu|Val|Gly|Arg<br>350|Ile|Asn|Gly|Gln|Phe<br>355|Gly|Thr|Val|Glu|Phe<br>360|
|Val|Pro|Ile|His|Phe<br>365|Met|His|Lys|Ser|Ile<br>370|Pro|Phe|Glu|Glu|Leu<br>375|
|Ile|Ser|Leu|Tyr|Ala<br>380|Val|Ser|Asp|Val|Cys<br>385|Leu|Val|Ser|Ser|Thr<br>390|
|Arg|Asp|Gly|Met|Asn<br>395|Leu|Val|Ser|Tyr|Glu<br>400|Tyr|Ile|Ala|Cys|Gln<br>405|
|Glu|Glu|Lys|Lys|Gly<br>410|Ser|Leu|Ile|Leu|Ser<br>415|Glu|Phe|Thr|Gly|Ala<br>420|
|Ala|Gln|Ser|Leu|Asn<br>425|Gly|Ala|Ile|Ile|Val<br>430|Asn|Pro|Trp|Asn|Thr<br>435|
|Asp|Asp|Leu|Ser|Asp<br>440|Ala|Ile|Asn|Glu|Ala<br>445|Leu|Thr|Leu|Pro|Asp<br>450|
|Val|Lys|Lys|Glu|Val<br>455|Asn|Trp|Glu|Lys|Leu<br>460|Tyr|Lys|Tyr|Ile|Ser<br>465|
|Lys|Tyr|Thr|Ser|Ala<br>470|Phe|Trp|Gly|Glu|Asn<br>475|Phe|Val|His|Glu|Leu<br>480|
|Tyr|Ser|Thr|Ser|Ser<br>485|Ser|Ser|Thr|Ser|Ser<br>490|Ser|Ala|Thr|Lys|Asn<br>495|

( 2 ) INFORMATION FOR SEQ ID NO:3:

( i ) SEQUENCE CHARACTERISTICS:
        ( A ) LENGTH: 3000 base pairs
        ( B ) TYPE: Nucleotide
        ( C ) STRANDEDNESS: Doublestranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Saccharomyces cerevisiae
        ( B ) STRAIN: S288C
        ( E ) HAPLOTYPE: Haploid ( v i i ) IMMEDIATE SOURCE:
        ( A ) LIBRARY: Genomic
        ( B ) CLONE: 6

( v i i ) POSITION IN GENOME:
        ( A ) CHROMOSOME/SEGMENT: 13

( x i ) SEQUENCE DESCRIPTION: SEQ ID NO:3:

| | | | | | |
|---|---|---|---|---|---|
|CCTCCTCTGG|ATCTTCTGGG|TCTTCTGCGC|CACCTTCCAT|TAAAAGGATT|50|
|ACGCCCCACT|TGACTGCGTC|TGCTGCAAAA|CAGCGTCCCT|TATTGGCTAA|100|
|ACAGCCTTCT|AATCTGAAAT|ATTCGGAGTT|AGCAGATATT|TCGTCGAGTG|150|
|AGACGTCTTC|GCAGCATAAT|GAGTCGGACC|CGGATGATCT|AACTACTGCC|200|
|CTGACGAGGA|TATGTTTCTG|ATTAGGAATT|GATGACGCGA|GAGGACTACA|250|
|AGGTTCAAAG|TTCGGCGCTA|TTCATAAATC|AACTAAGAAA|TATGCGCTGT|300|
|TAAGGTCATC|TCAGGAGCTG|TTTAGCCGTC|TTCCATGGTC|GATCGTTCCC|350|

-continued

| | | | | |
|---|---|---|---|---|
| TCTATCAAAG | GTAATGGCGC | CATGAAGAAC | GCCATAAACA | CTGCAGTCTT | 400 |
| GGAGAATATC | ATTCCGCACC | GTCATGTTAA | GTGGGTCGGT | ACCGTCGGAA | 450 |
| TCCCAACGGA | TGAGATTCCG | GAAAATATCC | TTGCGAACAT | CTCTGACTCT | 500 |
| TTAAAAGACA | AGTACGACTC | CTATCCTGTC | CTTACGGACG | ACGACACCTT | 550 |
| CAAAGCCGCA | TACAAAAACT | ACTGTAAACA | AATCTTGTGG | CCTACGCTGC | 600 |
| ATTACCAGAT | TCCAGACAAT | CCGAACTCGA | AGGCTTTTGA | AGATCACTCT | 650 |
| TGGAAGTTCT | ATAGAAACTT | AAACCAAAGG | TTTGCGGACG | CGATCGTTAA | 700 |
| AATCTATAAG | AAAGGTGACA | CCATCTGGAT | TCATGATTAC | CATTTAATGC | 750 |
| TGGTTCCGCA | GATGGTGAGA | GACGTCTTGC | CTTTTGCCAA | AATAGGATTT | 800 |
| ACCTTACATG | TCTCGTTCCC | CAGTAGTGAA | GTGTTAGGT | GTCTGGCTCA | 850 |
| GCGTGAGAAG | ATCTTAGAAG | GCTTGACCGG | TGCAGACTTT | GTCGGCTTCC | 900 |
| AGACGAGGGA | GTATGCAAGA | CATTTCTTAC | AGACGTCTAA | CCGTCTGCTA | 950 |
| ATGGCGGACG | TGGTACATGA | TGAAGAGCTA | AAGTATAACG | GCAGAGTCGT | 1000 |
| TTCTGTGAGG | TTCACCCCAG | TTGGTATCGA | CGCCTTTGAT | TTGCAATCGC | 1050 |
| AATTGAAGGA | TGGAAGTGTC | ATGCAATGGC | GTCAATTGAT | TCGTGAAAGA | 1100 |
| TGGCAAGGGA | AAAAACTAAT | TGTGTGTCGT | GATCAATTCG | ATAGAATTAG | 1150 |
| AGGTATTCAC | AAGAAATTGT | TGGCTTATGA | AAAATTCTTG | GTCGAAAATC | 1200 |
| CGGAATACGT | GGAAAAATCG | ACTTTAATTC | AAATCTGTAT | TGGAAGCAGT | 1250 |
| AAGGATGTAG | AACTGGAGCG | CCAGATCATG | ATTGTCGTGG | ATAGAATCAA | 1300 |
| CTCGCTATCC | ACCAATATTA | GTATTTCTCA | ACCTGTGGTG | TTTTTGCATC | 1350 |
| AAGATCTAGA | TTTTTCTCAG | TATTTAGCTT | TGAGTTCAGA | GGCAGATTTG | 1400 |
| TTCGTAGTCA | GCTCTCTAAG | GGAAGGTATG | AACTTGACAT | GTCACGAATT | 1450 |
| TATCGTTTGT | TCTGAGGACA | AAAATGCTCC | CCTACTGTTG | TCAGAATTTA | 1500 |
| CTGGTAGTGC | ATCTTTATTG | AATGATGGCG | CTATAATAAT | TAACCCATGG | 1550 |
| GATACCAAGA | ACTTCTCACA | AGCCATTCTC | AAGGGGTTGG | AGATGCCATT | 1600 |
| CGATAAGAGA | AGGCCACAGT | GGAAGAAATT | GATGAAAGAC | ATTATCAACA | 1650 |
| ACGACTCTAC | AAACTGGATC | AAGACTTCTT | TACAAGATAT | TCATATTTCG | 1700 |
| TGGCAATTCA | ATCAAGAAGG | TTCCAAGATC | TTCAAATTGA | ATACAAAAAC | 1750 |
| ACTGATGGAA | GATTACCAGT | CATCTAAAAA | GCGTATGTTT | GTTTTCAACA | 1800 |
| TTGCTGAACC | ACCTTCATCG | AGAATGATTT | CCATACTGAA | TGACATGACT | 1850 |
| TCTAAGGGCA | ATATCGTTTA | CATCATGAAC | TCATTCCAA | AGCCCATTCT | 1900 |
| GGAAAATCTT | TACAGTCGTG | TGCAAACAT | TGGGTTGATT | GCCGAGAATG | 1950 |
| GTGCATACGT | TAGTCTGAAC | GGTGTATGGT | ACAACATTGT | TGATCAAGTC | 2000 |
| GATTGGCGTA | ACGATGTAGC | CAAAATTCTC | GAGGACAAAG | TGGAGAGATT | 2050 |
| ACCTGGCTCG | TACTACAAGA | TAAATGAGTC | CATGATCAAG | TTCCACACTG | 2100 |
| AAAATGCGGA | AGATCAAGAT | CGTGTAGCTA | GTGTTATCGG | TGATGCCATC | 2150 |
| ACACATATCA | ATACTGTTTT | TGACCACAGA | GGTATTCATG | CCTACGTTTA | 2200 |
| CAAAAACGTT | GTTCCGTAC | AACAAGTGGG | ACTTTCCTTA | TCGGCAGCTC | 2250 |
| AATTTCTTTT | CAGATTCTAT | AATTCTGCTT | CGGATCCACT | GGATACGAGT | 2300 |
| TCCGGCCAAA | TCACAAATAT | TCAGACACCA | TCTCAACAAA | ATCCTTCAGA | 2350 |

| | | | | |
|---|---|---|---|---|
| TCAAGAACAA | CAACCTCCAG | CCTCTCCCAC | TGTGTCGATG | AACCATATTG | 2400 |
| ATTTCGCATG | TGTCTCTGGT | TCATCGTCTC | CTGTGCTTGA | ACCATTGTTC | 2450 |
| AAATTGGTCA | ATGATGAAGC | AAGTGAAGGG | CAAGTAAAAG | CCGGACACGC | 2500 |
| CATTGTTTAT | GGTGATGCTA | CTTCTACTTA | TGCCAAAGAA | CATGTAAATG | 2550 |
| GGTTAAACGA | ACTTTTCACG | ATCATTTCAA | GAATCATTGA | AGATTAAATT | 2600 |
| TTACCATTTT | AAAATTTTAA | TGTTCTTGGG | TATGAACTTT | TATTTTCAAC | 2650 |
| TGCTTATTAT | ATATCAATTC | TATAAATTTT | TTCTTCTCT | CTAACGACCA | 2700 |
| ATTATAAAAT | TCATCCTCTT | ATTTATTACA | GCATCTTATA | CATTATGTAT | 2750 |
| ATGGGTAGCT | ATTATTCATT | TTTGCTTCGT | AAGGACTTTT | TTTGTCAACT | 2800 |
| TTTTCATCCT | AAGCGGCTAA | AAGTGATTGG | AGAGGAATGT | CCAGGCGACC | 2850 |
| AATGATAAAA | ACGCTTTCTC | TTGGAACAAG | AAATAGGAGC | AATTGACAGT | 2900 |
| TGTCGATGAA | CAGCGAAAAT | AGTAAGATAA | CCTTCAAGCC | CAATATTCTA | 2950 |
| ATTAAAGGCG | TTTATATATT | TGTACTTTAT | GGTATGTGCA | TATGTATTGT | 3000 |

( 2 ) INFORMATION FOR SEQ ID NO:4:

( i ) SEQUENCE CHARACTERISTICS:
       ( A ) LENGTH: 785 amino acids
       ( B ) TYPE: Amino acid
       ( D ) TOPOLOGY: Linear ( i i ) MOLECULE TYPE: Polypeptide ( i i i ) HYPOTHETICAL: Yes         ?

( v ) FRAGMENT TYPE: C-terminal ( x i ) SEQUENCE DESCRIPTION: SEQ ID NO:4:

```
Arg Gly Leu Gln Gly Ser Lys Phe Gly Ala Ile His Lys Ser Thr
                 5                  10                  15

Lys Lys Tyr Ala Leu Leu Arg Ser Ser Gln Glu Leu Phe Ser Arg
                20                  25                  30

Leu Pro Trp Ser Ile Val Pro Ser Ile Lys Gly Asn Gly Ala Met
                35                  40                  45

Lys Asn Ala Ile Asn Thr Ala Val Leu Glu Asn Ile Ile Pro His
                50                  55                  60

Arg His Val Lys Trp Val Gly Thr Val Gly Ile Pro Thr Asp Glu
                65                  70                  75

Ile Pro Glu Asn Ile Leu Ala Asn Ile Ser Asp Ser Leu Lys Asp
                80                  85                  90

Lys Tyr Asp Ser Tyr Pro Val Leu Thr Asp Asp Thr Phe Lys
                95                 100                 105

Ala Ala Tyr Lys Asn Tyr Cys Lys Gln Ile Leu Trp Pro Thr Leu
               110                 115                 120

His Tyr Gln Ile Pro Asp Asn Pro Asn Ser Lys Ala Phe Glu Asp
               125                 130                 135

His Ser Trp Lys Phe Tyr Arg Asn Leu Asn Gln Arg Phe Ala Asp
               140                 145                 150

Ala Ile Val Lys Ile Tyr Lys Lys Gly Asp Thr Ile Trp Ile His
               155                 160                 165

Asp Tyr His Leu Met Leu Val Pro Gln Met Val Arg Asp Val Leu
               170                 175                 180

Pro Phe Ala Lys Ile Gly Phe Thr Leu His Val Ser Phe Pro Ser
               185                 190                 195
```

```
Ser  Glu  Val  Phe  Arg  Cys  Leu  Ala  Gln  Arg  Glu  Lys  Ile  Leu  Glu
               200                 205                           210

Gly  Leu  Thr  Gly  Ala  Asp  Phe  Val  Gly  Phe  Gln  Thr  Arg  Glu  Tyr
               215                 220                           225

Ala  Arg  His  Phe  Leu  Gln  Thr  Ser  Asn  Arg  Leu  Leu  Met  Ala  Asp
               230                 235                           240

Val  Val  His  Asp  Glu  Glu  Leu  Lys  Tyr  Asn  Gly  Arg  Val  Val  Ser
               245                 250                           255

Val  Arg  Phe  Thr  Pro  Val  Gly  Ile  Asp  Ala  Phe  Asp  Leu  Gln  Ser
               260                 265                           270

Gln  Leu  Lys  Asp  Gly  Ser  Val  Met  Gln  Trp  Arg  Gln  Leu  Ile  Arg
               275                 280                           285

Glu  Arg  Trp  Gln  Gly  Lys  Lys  Leu  Ile  Val  Cys  Arg  Asp  Gln  Phe
               290                 295                           300

Asp  Arg  Ile  Arg  Gly  Ile  His  Lys  Lys  Leu  Leu  Ala  Tyr  Glu  Lys
               305                 310                           315

Phe  Leu  Val  Glu  Asn  Pro  Glu  Tyr  Val  Glu  Lys  Ser  Thr  Leu  Ile
               320                 325                           330

Gln  Ile  Cys  Ile  Gly  Ser  Ser  Lys  Asp  Val  Glu  Leu  Glu  Arg  Gln
               335                 340                           345

Ile  Met  Ile  Val  Val  Asp  Arg  Ile  Asn  Ser  Leu  Ser  Thr  Asn  Ile
               350                 355                           360

Ser  Ile  Ser  Gln  Pro  Val  Val  Phe  Leu  His  Gln  Asp  Leu  Asp  Phe
               365                 370                           375

Ser  Gln  Tyr  Leu  Ala  Leu  Ser  Ser  Glu  Ala  Asp  Leu  Phe  Val  Val
               380                 385                           390

Ser  Ser  Leu  Arg  Glu  Gly  Met  Asn  Leu  Thr  Cys  His  Glu  Phe  Ile
               395                 400                           405

Val  Cys  Ser  Glu  Asp  Lys  Asn  Ala  Pro  Leu  Leu  Leu  Ser  Glu  Phe
               410                 415                           420

Thr  Gly  Ser  Ala  Ser  Leu  Leu  Asn  Asp  Gly  Ala  Ile  Ile  Ile  Asn
               425                 430                           435

Pro  Trp  Asp  Thr  Lys  Asn  Phe  Ser  Gln  Ala  Ile  Leu  Lys  Gly  Leu
               440                 445                           450

Glu  Met  Pro  Phe  Asp  Lys  Arg  Arg  Pro  Gln  Trp  Lys  Lys  Leu  Met
               455                 460                           465

Lys  Asp  Ile  Ile  Asn  Asn  Asp  Ser  Thr  Asn  Trp  Ile  Lys  Thr  Ser
               470                 475                           480

Leu  Gln  Asp  Ile  His  Ile  Ser  Trp  Gln  Phe  Asn  Gln  Glu  Gly  Ser
               485                 490                           495

Lys  Ile  Phe  Lys  Leu  Asn  Thr  Lys  Thr  Leu  Met  Glu  Asp  Tyr  Gln
               500                 505                           510

Ser  Ser  Lys  Lys  Arg  Met  Phe  Val  Phe  Asn  Ile  Ala  Glu  Pro  Pro
               515                 520                           525

Ser  Ser  Arg  Met  Ile  Ser  Ile  Leu  Asn  Asp  Met  Thr  Ser  Lys  Gly
               530                 535                           540

Asn  Ile  Val  Tyr  Ile  Met  Asn  Ser  Phe  Pro  Lys  Pro  Ile  Leu  Glu
               545                 550                           555

Asn  Leu  Tyr  Ser  Arg  Val  Gln  Asn  Ile  Gly  Leu  Ile  Ala  Glu  Asn
               560                 565                           570

Gly  Ala  Tyr  Val  Ser  Leu  Asn  Gly  Val  Trp  Tyr  Asn  Ile  Val  Asp
               575                 580                           585

Gln  Val  Asp  Trp  Arg  Asn  Asp  Val  Ala  Lys  Ile  Leu  Glu  Asp  Lys
```

-continued

|  |  |  |  | 590 |  |  |  | 595 |  |  |  | 600 |
|---|---|---|---|---|---|---|---|---|---|---|---|---|
| Val | Glu | Arg | Leu | Pro 605 | Gly | Ser | Tyr | Tyr 610 | Lys | Ile | Asn | Glu | Ser | Met 615 |
| Ile | Lys | Phe | His | Thr 620 | Glu | Asn | Ala | Glu 625 | Asp | Gln | Asp | Arg | Val | Ala 630 |
| Ser | Val | Ile | Gly | Asp 635 | Ala | Ile | Thr | His 640 | Ile | Asn | Thr | Val | Phe | Asp 645 |
| His | Arg | Gly | Ile | His 650 | Ala | Tyr | Val | Tyr 655 | Lys | Asn | Val | Val | Ser | Val 660 |
| Gln | Gln | Val | Gly | Leu 665 | Ser | Leu | Ser | Ala 670 | Ala | Gln | Phe | Leu | Phe | Arg 675 |
| Phe | Tyr | Asn | Ser | Ala 680 | Ser | Asp | Pro | Leu 685 | Asp | Thr | Ser | Ser | Gly | Gln 690 |
| Ile | Thr | Asn | Ile | Gln 695 | Thr | Pro | Ser | Gln 700 | Gln | Asn | Pro | Ser | Asp | Gln 705 |
| Glu | Gln | Gln | Pro | Pro 710 | Ala | Ser | Pro | Thr 715 | Val | Ser | Met | Asn | His | Ile 720 |
| Asp | Phe | Ala | Cys | Val 725 | Ser | Gly | Ser | Ser 730 | Ser | Pro | Val | Leu | Glu | Pro 735 |
| Leu | Phe | Lys | Leu | Val 740 | Asn | Asp | Glu | Ala 745 | Ser | Glu | Gly | Gln | Val | Lys 750 |
| Ala | Gly | His | Ala | Ile 755 | Val | Tyr | Gly | Asp 760 | Ala | Thr | Ser | Thr | Tyr | Ala 765 |
| Lys | Glu | His | Val | Asn 770 | Gly | Leu | Asn | Glu 775 | Leu | Phe | Thr | Ile | Ile | Ser 780 |
| Arg | Ile | Ile | Glu | Asp 785 |

( 2 ) INFORMATION FOR SEQ ID NO:5:

( i ) SEQUENCE CHARACTERISTICS:
        ( A ) LENGTH: 4 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:5:

Tyr  Ile  Ser  Lys ( 2 ) INFORMATION FOR SEQ ID NO:6:

( i ) SEQUENCE CHARACTERISTICS:
        ( A ) LENGTH: 9 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:6:

Asp  Val  Glu  Glu  Tyr  Gln  Tyr  Leu  Arg
                5

( 2 ) INFORMATION FOR SEQ ID NO:7:

-continued

```
      ( i ) SEQUENCE CHARACTERISTICS:
              ( A ) LENGTH: 8 amino acids
              ( B ) TYPE: Amino acid
              ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:7:

His  Phe  Leu  Ser  Ser  Val  Gln  Arg
                    5
```

( 2 ) INFORMATION FOR SEQ ID NO:8:

```
      ( i ) SEQUENCE CHARACTERISTICS:
              ( A ) LENGTH: 14 amino acids
              ( B ) TYPE: Amino acid
              ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:8:

Val  Leu  Asn  Val  Asn  Thr  Leu  Pro  Asn  Gly  Val  Glu  Tyr  Gln
                    5                        10
```

( 2 ) INFORMATION FOR SEQ ID NO:9:

```
      ( i ) SEQUENCE CHARACTERISTICS:
              ( A ) LENGTH: 9 amino acids
              ( B ) TYPE: Amino acid
              ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:9:

Ser  Val  Val  Asn  Glu  Leu  Val  Gly  Arg
                    5
```

( 2 ) INFORMATION FOR SEQ ID NO:10:

```
      ( i ) SEQUENCE CHARACTERISTICS:
              ( A ) LENGTH: 4
              ( B ) TYPE: Amino acid
              ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:10:

Glu  Thr  Phe  Lys
```

( 2 ) INFORMATION FOR SEQ ID NO:11:

```
      ( i ) SEQUENCE CHARACTERISTICS:
              ( A ) LENGTH: 5 amino acids
              ( B ) TYPE: Amino acid
              ( D ) TOPOLOGY: Linear
```

(i i) MOLECULE TYPE: Peptide (i i i) HYPOTHETICAL: No (i v) FRAGMENT TYPE: N-terminal (v) SEQUENCE DESCRIPTION: SEQ ID NO:11:

Leu Asp Tyr Ile Lys
                  5

(2) INFORMATION FOR SEQ ID NO:12:

(i) SEQUENCE CHARACTERISTICS:
        (A) LENGTH: 5 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:12:

Ile Leu Pro Val Arg
                  5

(2) INFORMATION FOR SEQ ID NO:13:

(i) SEQUENCE CHARACTERISTICS:
        (A) LENGTH: 6 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:13:

Glu Val Asn Xaa Glu Lys
                      5

(2) INFORMATION FOR SEQ ID NO:14:

(i) SEQUENCE CHARACTERISTICS:
        (A) LENGTH: 5 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:14:

Phe Tyr Asp Xaa Xaa
                  5

(2) INFORMATION FOR SEQ ID NO:15:

(i) SEQUENCE CHARACTERISTICS:
        (A) LENGTH: 13 amino acids
        (B) TYPE: Amino acid
        (D) TOPOLOGY: Linear (i i) MOLECULE TYPE: Peptide (i i i) HYPOTHETICAL: No ( i v ) FRAGMENT TYPE: N-terminal ( v ) SEQUENCE DESCRIPTION: SEQ ID NO:15:

Leu Xaa Ala Met Glu Val Phe Leu Asn Glu Xaa Pro Glu
              5                          10

( 2 ) INFORMATION FOR SEQ ID NO:16:

( i ) SEQUENCE CHARACTERISTICS:
        ( A ) LENGTH: 14 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:16:

Tyr Thr Ser Ala Phe Trp Gly Glu Asn Phe Val Xaa Glu Leu
              5                          10

( 2 ) INFORMATION FOR SEQ ID NO:17:

( i ) SEQUENCE CHARACTERISTICS:
        ( A ) LENGTH: 9 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:17:

Phe Gly Xaa Pro Gly Leu Glu Ile Pro
              5

( 2 ) INFORMATION FOR SEQ ID NO:18:

( i ) SEQUENCE CHARACTERISTICS:
        ( A ) LENGTH: 6 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:18:

Xaa Gly Ser Val Met Gln
              5

( 2 ) INFORMATION FOR SEQ ID NO:19:

( i ) SEQUENCE CHARACTERISTICS:
        ( A ) LENGTH: 7 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:19:

```
Leu  Pro  Gly  Ser  Tyr  Tyr  Lys
                 5
```

( 2 ) INFORMATION FOR SEQ ID NO:20:

( i ) SEQUENCE CHARACTERISTICS:
        ( A ) LENGTH: 12 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:20:

```
Asp  Ala  Ile  Val  Val  Asn  Pro  Met  Asp  Ser  Val  Ala
                 5                              10
```

( 2 ) INFORMATION FOR SEQ ID NO:21:

( i ) SEQUENCE CHARACTERISTICS:
        ( A ) LENGTH: 5 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:21:

```
Met  Ile  Ser  Ile  Leu
                 5
```

( 2 ) INFORMATION FOR SEQ ID NO:22:

( i ) SEQUENCE CHARACTERISTICS:
        ( A ) LENGTH: 6 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:22:

```
Arg  Arg  Pro  Gln  Trp  Lys
                 5
```

( 2 ) INFORMATION FOR SEQ ID NO:23:

( i ) SEQUENCE CHARACTERISTICS:
        ( A ) LENGTH: 5 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:23:

```
Ser  Xaa  Pro  Gln  Lys
                 5
```

( 2 ) INFORMATION FOR SEQ ID NO:24:

( i ) SEQUENCE CHARACTERISTICS:
        ( A ) LENGTH: 15 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:24:

Phe Tyr Arg Asn Leu Asn Gln Arg Phe Ala Asp Ala Ile Val Lys
              5                          10                    15

( 2 ) INFORMATION FOR SEQ ID NO:25:

( i ) SEQUENCE CHARACTERISTICS:
        ( A ) LENGTH: 11 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:25:

Asp Gly Ser Val Met Gln Xaa Xaa Gln Leu Xaa
              5                         10

( 2 ) INFORMATION FOR SEQ ID NO:26:

( i ) SEQUENCE CHARACTERISTICS:
        ( A ) LENGTH: 18 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:26:

Asn Ala Ile Asn Thr Ala Val Leu Glu Asn Ile Ile Pro Xaa Xaa
              5                          10                    15

Xaa Val Lys ( 2 ) INFORMATION FOR SEQ ID NO:27:

( i ) SEQUENCE CHARACTERISTICS:
        ( A ) LENGTH: 12 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:27:

Leu Val Asn Asp Glu Ala Ser Glu Gly Gln Val Lys
              5                         10

( 2 ) INFORMATION FOR SEQ ID NO:28:

( i ) SEQUENCE CHARACTERISTICS:
  ( A ) LENGTH: 11 amino acids
  ( B ) TYPE: Amino acid
  ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:28:

Xaa Gln Asp Ile Leu Leu Asn Asn Thr Phe Xaa
                  5                   10

( 2 ) INFORMATION FOR SEQ ID NO:29:

( i ) SEQUENCE CHARACTERISTICS:
    ( A ) LENGTH: 14 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:29:

Asp Thr Thr Gln Thr Ala Pro Val Xaa Asn Asn Val Xaa Pro
                  5                   10

( 2 ) INFORMATION FOR SEQ ID NO:30:

( i ) SEQUENCE CHARACTERISTICS:
    ( A ) LENGTH: 11 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:30:

Asn Gln Leu Asp Ala Xaa Asn Tyr Ala Glu Val
                  5                   10

( 2 ) INFORMATION FOR SEQ ID NO:31:

( i ) SEQUENCE CHARACTERISTICS:
    ( A ) LENGTH: 10 amino acids
    ( B ) TYPE: Amino acid
    ( D ) TOPOLOGY: Linear ( i i ) MOLECULE TYPE: Peptide ( i i i ) HYPOTHETICAL: Yes ( i v ) FRAGMENT TYPE: N-terminal ( v ) SEQUENCE DESCRIPTION: SEQ ID NO:31:

Asn Leu Ser Arg Trp Arg Asn Tyr Ala Glu
                  5                   10

( 2 ) INFORMATION FOR SEQ ID NO:32:

( i ) SEQUENCE CHARACTERISTICS:
    ( A ) LENGTH: 4 amino acids
    ( B ) TYPE: Amino acid -continued ( D ) TOPOLOGY: Linear ( i i ) MOLECULE TYPE: Peptide ( i i i ) HYPOTHETICAL: Yes ( i v ) FRAGMENT TYPE: N-terminal ( v ) SEQUENCE DESCRIPTION: SEQ ID NO:32:

Trp Gln Gly Lys ( 2 ) INFORMATION FOR SEQ ID NO:33:

( i ) SEQUENCE CHARACTERISTICS:
      ( A ) LENGTH: 11 amino acids
      ( B ) TYPE: Amino acid
      ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:33:

Ile Gln Leu Gly Glu Ser Asn Asp Asp Xaa Xaa
            5                       10

( 2 ) INFORMATION FOR SEQ ID NO:34:

( i ) SEQUENCE CHARACTERISTICS:
      ( A ) LENGTH: 11 amino acids
      ( B ) TYPE: Amino acid
      ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:34:

Gln Val Pro Thr Ile Gln Asp Xaa Thr Asn Lys
            5                     10

( 2 ) INFORMATION FOR SEQ ID NO:35:

( i ) SEQUENCE CHARACTERISTICS:
      ( A ) LENGTH: 6 amino acids
      ( B ) TYPE: Amino acid
      ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:35:

Xaa Tyr Xaa Tyr Val Lys
            5

( 2 ) INFORMATION FOR SEQ ID NO:36:

( i ) SEQUENCE CHARACTERISTICS:
      ( A ) LENGTH: 6 amino acids
      ( B ) TYPE: Amino acid
      ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:36:

Asn Gln Leu Gly Asn Tyr
                     5

( 2 ) INFORMATION FOR SEQ ID NO:37:

( i ) SEQUENCE CHARACTERISTICS:
      ( A ) LENGTH: 4 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:37:

Val Ala Leu Thr ( 2 ) INFORMATION FOR SEQ ID NO:38:

( i ) SEQUENCE CHARACTERISTICS:
      ( A ) LENGTH: 12 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:38:

Asp Ala Ile Val Val Asn Pro Xaa Asp Ser Val Ala
                     5                   10

( 2 ) INFORMATION FOR SEQ ID NO:39:

( i ) SEQUENCE CHARACTERISTICS:
      ( A ) LENGTH: 9 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:39:

Thr Phe Thr Asn Tyr Asp Gly Ser Lys
                     5

( 2 ) INFORMATION FOR SEQ ID NO:40:

( i ) SEQUENCE CHARACTERISTICS:
      ( A ) LENGTH: 10 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:40:

Thr Gly Asn Asp Pro Ser His Ile Ala Lys
         5                       10

( 2 ) INFORMATION FOR SEQ ID NO:41:

( i ) SEQUENCE CHARACTERISTICS:
        ( A ) LENGTH: 7 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:41:

Ile Tyr Glu Ser Gln Gly Lys
         5

( 2 ) INFORMATION FOR SEQ ID NO:42:

( i ) SEQUENCE CHARACTERISTICS:
        ( A ) LENGTH: 12 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:42:

Ala Glu Gly Ala Thr Gly Gly Leu Val Pro His Lys
         5                       10

( 2 ) INFORMATION FOR SEQ ID NO:43:

( i ) SEQUENCE CHARACTERISTICS:
        ( A ) LENGTH: 10 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:43:

Leu Ala Thr Glu Leu Pro Ala Xaa Ser Lys
         5                       10

( 2 ) INFORMATION FOR SEQ ID NO:44:

( i ) SEQUENCE CHARACTERISTICS:
        ( A ) LENGTH: 8 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:44:

Ser Leu Leu Asp Ala Gly Ala Lys
         5

( 2 ) INFORMATION FOR SEQ ID NO:45:

( i ) SEQUENCE CHARACTERISTICS:
        ( A ) LENGTH: 14 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:45:

Glu Lys Pro Gln Asp Leu Asp Asp Pro Leu Tyr Leu Thr
            5                          10

( 2 ) INFORMATION FOR SEQ ID NO:46:

( i ) SEQUENCE CHARACTERISTICS:
        ( A ) LENGTH: 11 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:46:

Xaa Gln Xaa His Gln Asp Xaa Xaa Asn Leu Thr
            5                       10

( 2 ) INFORMATION FOR SEQ ID NO:47:

( i ) SEQUENCE CHARACTERISTICS:
        ( A ) LENGTH: 15 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:47:

Phe Asn Asp Glu Ser Ile Ile Ile Gly Tyr Phe Xaa Xaa Ala Pro
            5                        10                      15

( 2 ) INFORMATION FOR SEQ ID NO:48:

( i ) SEQUENCE CHARACTERISTICS:
        ( A ) LENGTH: 14 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:48:

Ser Arg Leu Phe Leu Phe Asp Tyr Asp Gly Thr Leu Thr Pro
            5                          10

( 2 ) INFORMATION FOR SEQ ID NO:49:

( i ) SEQUENCE CHARACTERISTICS:
        ( A ) LENGTH: 11 amino acids (B) TYPE: Amino acid
(C) TOPOLOGY: Linear (ii) MOLECULE TYPE: Peptide (iii) HYPOTHETICAL: No (iv) FRAGMENT TYPE: N-terminal (v) SEQUENCE DESCRIPTION:49:

Gln Leu Gly Asn Tyr Gly Phe Tyr Pro Val Tyr
                  5                      10

(2) INFORMATION FOR SEQ ID NO:50:

(i) SEQUENCE CHARACTERISTICS:
    (A) LENGTH: 11 amino acids
    (B) TYPE: Amino acid
    (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:50:

Phe Leu Val Glu Asn Pro Glu Tyr Val Glu Lys
                  5                      10

(2) INFORMATION FOR SEQ ID NO:51:

(i) SEQUENCE CHARACTERISTICS:
    (A) LENGTH: 11 amino acids
    (B) TYPE: Amino acid
    (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:51:

Xaa Ile Thr Pro His Leu Thr Ala Xaa Ala Ala
                  5                      10

(2) INFORMATION FOR SEQ ID NO:52:

(i) SEQUENCE CHARACTERISTICS:
    (A) LENGTH: 10 amino acids
    (B) TYPE: Amino acid
    (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:52:

Thr Leu Met Glu Asp Tyr Gln Ser Ser Lys
                  5                  10

(2) INFORMATION FOR SEQ ID NO:53:

(i) SEQUENCE CHARACTERISTICS:
    (A) LENGTH: 15 amino acids
    (B) TYPE: Amino acid
    (C) TOPOLOGY: Linear (ii) MOLECULE TYPE: Peptide ( i i i ) HYPOTHETICAL: No ( i v ) FRAGMENT TYPE: N-terminal ( v ) SEQUENCE DESCRIPTION:53:

Ile Leu Glu Gly Leu Thr Gly Ala Asp Phe Val Gly Phe Gln Thr
                    5                   10                  15

( 2 ) INFORMATION FOR SEQ ID NO:54:

( i ) SEQUENCE CHARACTERISTICS:
      ( A ) LENGTH: 14 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:54:

Gln Ile Leu Xaa Pro Thr Leu Xaa Tyr Gln Ile Pro Asp Asn
                5                   10

( 2 ) INFORMATION FOR SEQ ID NO:55:

( i ) SEQUENCE CHARACTERISTICS:
      ( A ) LENGTH: 7 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:55:

Phe Gly Gly Tyr Ser Asn Lys
                5

( 2 ) INFORMATION FOR SEQ ID NO:56:

( i ) SEQUENCE CHARACTERISTICS:
      ( A ) LENGTH: 23 amino acids
      ( B ) TYPE: Amino acid
      ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:56:

Phe Xaa Thr Glu Asn Ala Glu Asp Gln Asp Xaa Val Ala Xaa Val
                    5                   10                  15
Ile Gly Xaa Ala Ile Xaa Xaa Ile
                20

( 2 ) INFORMATION FOR SEQ ID NO:57:

( i ) SEQUENCE CHARACTERISTICS:
      ( A ) LENGTH: 18 amino acids
      ( B ) TYPE: Amino acid
      ( C ) TOPOLOGY: Linear ( i i ) MOLECULE TYPE: Peptide -continued (iii) HYPOTHETICAL: No (iv) FRAGMENT TYPE: N-terminal (v) SEQUENCE DESCRIPTION:57:

Xaa Val Gly Thr Val Gly Ile Pro Thr Asp Glu Ile Pro Glu Asn
                  5                   10                  15

Ile Leu Ala (2) INFORMATION FOR SEQ ID NO:58:

(i) SEQUENCE CHARACTERISTICS:
        (A) LENGTH: 19 amino acids
        (B) TYPE: Amino acid
        (C) TOPOLOGY: Linear (ii) MOLECULE TYPE: Peptides (iii) HYPOTHETICAL: No (iv) FRAGMENT TYPE: N-terminal (v) SEQUENCE DESCRIPTION:58:

Leu Leu Val His Ser Leu Leu Asn Asn Thr Ser Gln Thr Ser Leu
                  5                   10                  15

Glu Gly Pro Asn (2) INFORMATION FOR SEQ ID NO:59:

(i) SEQUENCE CHARACTERISTICS:
        (A) LENGTH: 20 amino acids
        (B) TYPE: Amino acid
        (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:59:

Ser Ser Thr Thr Asn Thr Ala Thr Leu Xaa Xaa Leu Val Ser Ser
                  5                   10                  15

Xaa Ile Phe Met Glu
              20

(2) INFORMATION FOR SEQ ID NO:60:

(i) SEQUENCE CHARACTERISTICS:
        (A) LENGTH: 15 amino acids
        (B) TYPE: Amino acid
        (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:60:

Ala Xaa Asn Arg Pro Thr Ser Ala Ala Thr Ser Leu Val Asn Arg
                  5                   10                  15

(2) INFORMATION FOR SEQ ID NO:61:

(i) SEQUENCE CHARACTERISTICS:
        (A) LENGTH: 6 amino acids
        (B) TYPE: Amino acid
        (C) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:61:

Xaa Phe Thr Ile Ile Xaa
                    5

( 2 ) INFORMATION FOR SEQ ID NO:62:

( i ) SEQUENCE CHARACTERISTICS:
        ( A ) LENGTH: 15 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:62:

Asn Leu Thr Ala Asn Ala Thr Thr Ser His Thr Pro Thr Ser Lys
                    5                   10                  15

( 2 ) INFORMATION FOR SEQ ID NO:63:

( i ) SEQUENCE CHARACTERISTICS:
        ( A ) LENGTH: 7 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:63:

Phe Xaa Xaa Tyr Ser Asn Lys
                    5

( 2 ) INFORMATION FOR SEQ ID NO:64:

( i ) SEQUENCE CHARACTERISTICS:
        ( A ) LENGTH: 7 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:64:

Xaa Pro Xaa Ala Phe Asn Xaa
                    5

( 2 ) INFORMATION FOR SEQ ID NO:65:

( i ) SEQUENCE CHARACTERISTICS:
        ( A ) LENGTH: 8 amino acids
        ( B ) TYPE: Amino acid
        ( C ) TOPOLOGY: Linear ( i i ) MOLECULE TYPE: Peptide ( i i i ) HYPOTHETICAL: No (i v) FRAGMENT TYPE: N-terminal (v) SEQUENCE DESCRIPTION:65:

Ile Ala Ser Pro Ile Gln Xaa Glu
                5

(2) INFORMATION FOR SEQ ID NO:66:

(i) SEQUENCE CHARACTERISTICS:
      (A) LENGTH: 7 amino acids
      (B) TYPE: Amino acid
      (C) TOPOLOGY: Linear (i i) MOLECULE TYPE: Peptide (i i i) HYPOTHETICAL: No (i v) FRAGMENT TYPE: N-terminal (v) SEQUENCE DESCRIPTION:66:

Gln Arg Pro Leu Leu Ala Lys
              5

(2) INFORMATION FOR SEQ ID NO:67:

(i) SEQUENCE CHARACTERISTICS:
      (A) LENGTH: 12 amino acids
      (B) TYPE: Amino acid
      (C) TOPOLOGY: Linear (i i) MOLECULE TYPE: Peptide (i i i) HYPOTHETICAL: No (i v) FRAGMENT TYPE: N-terminal (v) SEQUENCE DESCRIPTION:67:

Phe Phe Ser Pro Ser Ser Asn Ile Pro Thr Asp Arg
              5                      10

(2) INFORMATION FOR SEQ ID NO:68:

(i) SEQUENCE CHARACTERISTICS:
      (A) LENGTH: 9 amino acids
      (B) TYPE: Amino acid
      (C) TOPOLOGY: Linear (i i) MOLECULE TYPE: Peptide (i i i) HYPOTHETICAL: No (i v) FRAGMENT TYPE: N-terminal (v) SEQUENCE DESCRIPTION:68:

Ala Leu Ser Asn Asn Ile Ser Gln Glu
              5

(2) INFORMATION FOR SEQ ID NO:69:

(i) SEQUENCE CHARACTERISTICS:
      (A) LENGTH: 6 amino acids
      (B) TYPE: Amino acid
      (C) TOPOLOGY: Linear (i i) MOLECULE TYPE: Peptide (i i i) HYPOTHETICAL: No (i v) FRAGMENT TYPE: N-terminal (v) SEQUENCE DESCRIPTION:69:

```
Xaa Xaa Xaa Tyr Thr Pro
              5
```

( 2 ) INFORMATION FOR SEQ ID NO:70:

( i ) SEQUENCE CHARACTERISTICS:
        ( A ) LENGTH: 16 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:70:

```
Ile Ala Ser Pro Ile Gln Gln Gln Gln Asp Pro Thr Ala Asn
              5                   10                  15
Leu
```

( 2 ) INFORMATION FOR SEQ ID NO:71:

( i ) SEQUENCE CHARACTERISTICS:
        ( A ) LENGTH: 6 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:71:

```
Thr Met Leu Lys Pro Arg
              5
```

( 2 ) INFORMATION FOR SEQ ID NO:72:

( i ) SEQUENCE CHARACTERISTICS:
        ( A ) LENGTH: 6 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:72:

```
Ile Ile Glu Asp Glu Ala
              5
```

( 2 ) INFORMATION FOR SEQ ID NO:73:

( i ) SEQUENCE CHARACTERISTICS:
        ( A ) LENGTH: 11 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:73:

```
Ile Thr Pro His Leu Thr Ala Ser Ala Ala Lys
```

( 2 ) INFORMATION FOR SEQ ID NO:74:

( i ) SEQUENCE CHARACTERISTICS:
    ( A ) LENGTH: 8 amino acids
    ( B ) TYPE: Amino acid
    ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:74:

Ser Leu Val Ala Pro Ala Pro Glu
      5

( 2 ) INFORMATION FOR SEQ ID NO:75:

( i ) SEQUENCE CHARACTERISTICS:
    ( A ) LENGTH: 12 amino acids
    ( B ) TYPE: Amino acid
    ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:75:

Lys Pro Gln Asp Leu Asp Asp Pro Leu Tyr Leu
      5        10

( 2 ) INFORMATION FOR SEQ ID NO:76:

( i ) SEQUENCE CHARACTERISTICS:
    ( A ) LENGTH: 6
    ( B ) TYPE: Amino acid
    ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:76:

Lys Tyr Ala Leu Leu Arg
      5

( 2 ) INFORMATION FOR SEQ ID NO:77:

( i ) SEQUENCE CHARACTERISTICS:
    ( A ) LENGTH: 11 amino acids
    ( B ) TYPE: Amino acid
    ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:77:

Gln Leu Gly Asn Tyr Xaa Phe Tyr Pro Val Tyr
      5        10

( 2 ) INFORMATION FOR SEQ ID NO:78:

( i ) SEQUENCE CHARACTERISTICS:
(A) LENGTH: 8 amino acids
(B) TYPE: Amino acid
(C) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:78:

Ala Phe Glu Asp His Ser Trp Lys
                  5

( 2 ) INFORMATION FOR SEQ ID NO:79:

( i ) SEQUENCE CHARACTERISTICS:
(A) LENGTH: 16 amino acids
(B) TYPE: Amino acid
(C) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:79:

Ala Gly His Ala Ile Val Tyr Gly Asp Ala Thr Ser Thr Tyr Ala
                  5                          10                         15
Lys ( 2 ) INFORMATION FOR SEQ ID NO:80:

( i ) SEQUENCE CHARACTERISTICS:
(A) LENGTH: 9 amino acids
(B) TYPE: Amino acid
(C) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:80:

Glu Arg Leu Pro Gly Ser Tyr Tyr Lys
                  5

( 2 ) INFORMATION FOR SEQ ID NO:81:

( i ) SEQUENCE CHARACTERISTICS:
(A) LENGTH: 7 amino acids
(B) TYPE: Amino acid
(C) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:81:

Thr Leu Met Glu Asp Tyr Gln
                  5

( 2 ) INFORMATION FOR SEQ ID NO:82:

( i ) SEQUENCE CHARACTERISTICS:

( A ) LENGTH: 1098 amino acids
( B ) TYPE: Amino acid
( C ) TOPOLOGY: Linear ( i i ) MOLECULE TYPE: Polypeptide ( i i i ) HYPOTHETICAL: Yes ( v ) SEQUENCE DESCRIPTION:82:

```
Met Ala Leu Ile Val Ala Ser Leu Phe Leu Pro Tyr Gln Pro Gln
                 5                  10                 15

Phe Glu Leu Asp Thr Ser Leu Pro Glu Asn Ser Gln Val Asp Ser
                20                  25                 30

Ser Leu Val Asn Ile Gln Ala Met Ala Asn Asp Gln Gln Gln Gln
                35                  40                 45

Arg Ala Leu Ser Asn Asn Ile Ser Gln Glu Ser Leu Val Ala Pro
                50                  55                 60

Ala Pro Glu Gln Gly Val Pro Pro Ala Ile Ser Arg Ser Ala Thr
                65                  70                 75

Arg Ser Pro Ser Ala Phe Asn Arg Ala Ser Ser Thr Thr Asn Thr
                80                  85                 90

Ala Thr Leu Asp Asp Leu Val Ser Ser Asp Ile Phe Met Glu Asn
                95                 100                105

Leu Thr Ala Asn Ala Thr Thr Ser His Thr Pro Thr Ser Lys Thr
               110                 115                120

Met Leu Lys Pro Arg Lys Asn Gly Ser Val Glu Arg Phe Phe Ser
               125                 130                135

Pro Ser Ser Asn Ile Pro Thr Asp Arg Ile Ala Ser Pro Ile Gln
               140                 145                150

His Glu His Asp Ser Gly Ser Arg Ile Ala Ser Pro Ile Gln Gln
               155                 160                165

Gln Gln Gln Asp Pro Thr Thr Asn Leu Leu Lys Asn Val Asn Lys
               170                 175                180

Ser Leu Leu Val His Ser Leu Leu Asn Asn Thr Ser Gln Thr Ser
               185                 190                195

Leu Glu Gly Pro Asn Asn His Ile Val Thr Pro Lys Ser Arg Ala
               200                 205                210

Gly Asn Arg Pro Thr Ser Ala Ala Thr Ser Leu Val Asn Arg Thr
               215                 220                225

Lys Gln Gly Ser Ala Ser Ser Gly Ser Ser Gly Ser Ser Ala Pro
               230                 235                240

Pro Ser Ile Lys Arg Ile Thr Pro His Leu Thr Ala Ser Ala Ala
               245                 250                255

Lys Gln Arg Pro Leu Leu Ala Lys Gln Pro Ser Asn Leu Lys Tyr
               260                 265                270

Ser Glu Leu Ala Asp Ile Ser Ser Ser Glu Thr Ser Ser Gln His
               275                 280                285

Asn Glu Ser Asp Pro Asp Asp Leu Thr Thr Ala Pro Asp Glu Glu
               290                 295                300

Tyr Val Ser Asp Leu Glu Met Asp Asp Ala Lys Gln Asp Tyr Lys
               305                 310                315

Val Pro Lys Phe Gly Gly Tyr Ser Asn Lys Ser Lys Leu Lys Lys
               320                 325                330

Tyr Ala Leu Leu Arg Ser Ser Gln Glu Leu Phe Ser Arg Leu Pro
               335                 340                345

Trp Ser Ile Val Pro Ser Ile Lys Gly Asn Gly Ala Met Lys Asn
```

|     |     |     |     |     |     |     |     |     |     |     |     |     |
|-----|-----|-----|-----|-----|-----|-----|-----|-----|-----|-----|-----|-----|
|     |     |     |     | 350 |     |     |     | 355 |     |     |     | 360 |
| Ala | Ile | Asn | Thr | Ala | Val | Leu | Glu | Asn | Ile | Pro | His | Arg | His |
|     |     |     |     | 365 |     |     |     | 370 |     |     |     | 375 |
| Val | Lys | Trp | Val | Gly | Thr | Val | Gly | Ile | Pro | Thr | Asp | Glu | Ile | Pro |
|     |     |     |     | 380 |     |     |     | 385 |     |     |     | 390 |
| Glu | Asn | Ile | Leu | Ala | Asn | Ile | Ser | Asp | Ser | Leu | Lys | Asp | Lys | Tyr |
|     |     |     |     | 395 |     |     |     | 400 |     |     |     | 405 |
| Asp | Ser | Tyr | Pro | Val | Leu | Thr | Asp | Asp | Thr | Phe | Lys | Ala | Ala |
|     |     |     |     | 410 |     |     |     | 415 |     |     |     | 420 |
| Tyr | Lys | Asn | Tyr | Cys | Lys | Gln | Ile | Leu | Trp | Pro | Thr | Leu | His | Tyr |
|     |     |     |     | 425 |     |     |     | 430 |     |     |     | 435 |
| Gln | Ile | Pro | Asp | Asn | Pro | Asn | Ser | Lys | Ala | Phe | Glu | Asp | His | Ser |
|     |     |     |     | 440 |     |     |     | 445 |     |     |     | 450 |
| Trp | Lys | Phe | Tyr | Arg | Asn | Leu | Asn | Gln | Arg | Phe | Ala | Asp | Ala | Ile |
|     |     |     |     | 455 |     |     |     | 460 |     |     |     | 465 |
| Val | Lys | Ile | Tyr | Lys | Lys | Gly | Asp | Thr | Ile | Trp | Ile | His | Asp | Tyr |
|     |     |     |     | 470 |     |     |     | 475 |     |     |     | 480 |
| His | Leu | Met | Leu | Val | Pro | Gln | Met | Val | Arg | Asp | Val | Leu | Pro | Phe |
|     |     |     |     | 485 |     |     |     | 490 |     |     |     | 495 |
| Ala | Lys | Ile | Gly | Phe | Thr | Leu | His | Val | Ser | Phe | Pro | Ser | Ser | Glu |
|     |     |     |     | 500 |     |     |     | 505 |     |     |     | 510 |
| Val | Phe | Arg | Cys | Leu | Ala | Gln | Arg | Glu | Lys | Ile | Leu | Glu | Gly | Leu |
|     |     |     |     | 515 |     |     |     | 520 |     |     |     | 525 |
| Thr | Gly | Ala | Asp | Phe | Val | Gly | Phe | Gln | Thr | Arg | Glu | Tyr | Ala | Arg |
|     |     |     |     | 530 |     |     |     | 535 |     |     |     | 540 |
| His | Phe | Leu | Gln | Thr | Ser | Asn | Arg | Leu | Leu | Met | Ala | Asp | Val | Val |
|     |     |     |     | 545 |     |     |     | 550 |     |     |     | 555 |
| His | Asp | Glu | Glu | Leu | Lys | Tyr | Asn | Gly | Arg | Val | Val | Ser | Val | Arg |
|     |     |     |     | 560 |     |     |     | 565 |     |     |     | 570 |
| Phe | Thr | Pro | Val | Gly | Ile | Asp | Ala | Phe | Asp | Leu | Gln | Ser | Gln | Leu |
|     |     |     |     | 575 |     |     |     | 580 |     |     |     | 585 |
| Lys | Asp | Gly | Ser | Val | Met | Gln | Trp | Arg | Gln | Leu | Ile | Arg | Glu | Arg |
|     |     |     |     | 590 |     |     |     | 595 |     |     |     | 600 |
| Trp | Gln | Gly | Lys | Lys | Leu | Ile | Val | Cys | Arg | Asp | Gln | Phe | Asp | Arg |
|     |     |     |     | 605 |     |     |     | 610 |     |     |     | 615 |
| Ile | Arg | Gly | Ile | His | Lys | Lys | Leu | Leu | Ala | Tyr | Glu | Lys | Phe | Leu |
|     |     |     |     | 620 |     |     |     | 625 |     |     |     | 630 |
| Val | Glu | Asn | Pro | Glu | Tyr | Val | Glu | Lys | Ser | Thr | Leu | Ile | Gln | Ile |
|     |     |     |     | 635 |     |     |     | 640 |     |     |     | 645 |
| Cys | Ile | Gly | Ser | Ser | Lys | Asp | Val | Glu | Leu | Glu | Arg | Gln | Ile | Met |
|     |     |     |     | 650 |     |     |     | 655 |     |     |     | 660 |
| Ile | Val | Val | Asp | Arg | Ile | Asn | Ser | Leu | Ser | Thr | Asn | Ile | Ser | Ile |
|     |     |     |     | 665 |     |     |     | 670 |     |     |     | 675 |
| Ser | Gln | Pro | Val | Val | Phe | Leu | His | Gln | Asp | Leu | Asp | Phe | Ser | Gln |
|     |     |     |     | 680 |     |     |     | 685 |     |     |     | 690 |
| Tyr | Leu | Ala | Leu | Ser | Ser | Glu | Ala | Asp | Leu | Phe | Val | Val | Ser | Ser |
|     |     |     |     | 695 |     |     |     | 700 |     |     |     | 705 |
| Leu | Arg | Glu | Gly | Met | Asn | Leu | Thr | Cys | His | Glu | Phe | Ile | Val | Cys |
|     |     |     |     | 710 |     |     |     | 715 |     |     |     | 720 |
| Ser | Glu | Asp | Lys | Asn | Ala | Pro | Leu | Leu | Leu | Ser | Glu | Phe | Thr | Gly |
|     |     |     |     | 725 |     |     |     | 730 |     |     |     | 735 |
| Ser | Ala | Ser | Leu | Leu | Asn | Asp | Gly | Ala | Ile | Ile | Ile | Asn | Pro | Trp |
|     |     |     |     | 740 |     |     |     | 745 |     |     |     | 750 |

| | | | | | | | | | | | | | | |
|---|---|---|---|---|---|---|---|---|---|---|---|---|---|---|
| Asp | Thr | Lys | Asn | Phe 755 | Ser | Gln | Ala | Ile | Leu 760 | Lys | Gly | Leu | Glu | Met 765 |
| Pro | Phe | Asp | Lys | Arg 770 | Arg | Pro | Gln | Trp | Lys 775 | Lys | Leu | Met | Lys | Asp 780 |
| Ile | Ile | Asn | Asn | Asp 785 | Ser | Thr | Asn | Trp | Ile 790 | Lys | Thr | Ser | Leu | Gln 795 |
| Asp | Ile | His | Ile | Ser 800 | Trp | Gln | Phe | Asn | Gln 805 | Glu | Gly | Ser | Lys | Ile 810 |
| Phe | Lys | Leu | Asn | Thr 815 | Lys | Thr | Leu | Met | Glu 820 | Asp | Tyr | Gln | Ser | Ser 825 |
| Lys | Lys | Arg | Met | Phe 830 | Val | Phe | Asn | Ile | Ala 835 | Glu | Pro | Pro | Ser | Ser 840 |
| Arg | Met | Ile | Ser | Ile 845 | Leu | Asn | Asp | Met | Thr 850 | Ser | Lys | Gly | Asn | Ile 855 |
| Val | Tyr | Ile | Met | Asn 860 | Ser | Phe | Pro | Lys | Pro 865 | Ile | Leu | Glu | Asn | Leu 870 |
| Tyr | Ser | Arg | Val | Gln 875 | Asn | Ile | Gly | Leu | Ile 880 | Ala | Glu | Asn | Gly | Ala 885 |
| Tyr | Val | Ser | Leu | Asn 890 | Gly | Val | Trp | Tyr | Asn 895 | Ile | Val | Asp | Gln | Val 900 |
| Asp | Trp | Arg | Asn | Asp 905 | Val | Ala | Lys | Ile | Leu 910 | Glu | Asp | Lys | Val | Glu 915 |
| Arg | Leu | Pro | Gly | Ser 920 | Tyr | Tyr | Lys | Ile | Asn 925 | Glu | Ser | Met | Ile | Lys 930 |
| Phe | His | Thr | Glu | Asn 935 | Ala | Glu | Asp | Gln | Asp 940 | Arg | Val | Ala | Ser | Val 945 |
| Ile | Gly | Asp | Ala | Ile 950 | Thr | His | Ile | Asn | Thr 955 | Val | Phe | Asp | His | Arg 960 |
| Gly | Ile | His | Ala | Tyr 965 | Val | Tyr | Lys | Asn | Val 970 | Val | Ser | Val | Gln | Gln 975 |
| Val | Gly | Leu | Ser | Leu 980 | Ser | Ala | Ala | Gln | Phe 985 | Leu | Phe | Arg | Phe | Tyr 990 |
| Asn | Ser | Ala | Ser | Asp 995 | Pro | Leu | Asp | Thr | Ser 1000 | Ser | Gly | Gln | Ile | Thr 1005 |
| Asn | Ile | Gln | Thr | Pro 1010 | Ser | Gln | Gln | Asn | Pro 1015 | Ser | Asp | Gln | Glu | Gln 1020 |
| Gln | Pro | Pro | Ala | Ser 1025 | Pro | Thr | Val | Ser | Met 1030 | Asn | His | Ile | Asp | Phe 1035 |
| Ala | Cys | Val | Ser | Gly 1040 | Ser | Ser | Ser | Pro | Val 1045 | Leu | Glu | Pro | Leu | Phe 1050 |
| Lys | Leu | Val | Asn | Asp 1055 | Glu | Ala | Ser | Glu | Gly 1060 | Gln | Val | Lys | Ala | Gly 1065 |
| His | Ala | Ile | Val | Tyr 1070 | Gly | Asp | Ala | Thr | Ser 1075 | Thr | Tyr | Ala | Lys | Glu 1080 |
| His | Val | Asn | Gly | Leu 1085 | Asn | Glu | Leu | Phe | Thr 1090 | Ile | Ile | Ser | Arg | Ile 1095 |
| Ile | Glu | Asp 1098 | | | | | | | | | | | | |

( 2 ) INFORMATION FOR SEQ ID NO:83:

( i ) SEQUENCE CHARACTERISTICS:
        ( A ) LENGTH: 5981 basepairs
        ( B ) TYPE: Nucleotide
        ( C ) STRANDEDNESS: Doublestranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
   ( A ) ORGANISM: Saccharomyces cerevisiae
   ( B ) STRAIN: S288C
   ( C ) HAPLOTYPE: Haploid ( v i i ) IMMEDIATE SOURCE:
   ( A ) LIBRARY: Genomic
   ( B ) CLONE: 6 and 10

( v i i i ) POSITION IN GENOME:
   ( A ) CHROMOSOME/SEGMENT: 13

( x i ) SEQUENCE DESCRIPTION: SEQ ID NO:83:

| | | | | | |
|---|---|---|---|---|---|
| GGCTCACATT | CCAAAAAGAA | CAGTTCGAAC | GATAAAGCTT | TTCACCGCTG | 50 |
| GTGGTGATAA | CAAGGTTAGG | ATATGGAAGT | TGAACAGAGA | TGAAAACGGA | 100 |
| CAAAATGGGG | GGGTGCGTAA | GATTGAAAGC | CTTGACTTTC | TTGGCTCGTG | 150 |
| ACGCATCACG | AACAGGCCAT | AAATGTAATC | CGATTCAACT | CGAAGGGTGA | 200 |
| CGTACTGGCG | TCTGCGGGCG | ATGACGGCCA | AGTGCTGCTA | TGGAAGCAAG | 250 |
| AAGAACCAAA | TACACAGCAA | GAATCTGTGG | TCAGACCATT | CGGAATGGAT | 300 |
| GCGGAGACTA | GTGAAGCAGA | CGAGAACAAG | GAGAAATGGG | TTGTGTGGAA | 350 |
| ACGGCTGCGT | GGTGGTAGCG | GTGCTACTGC | GGCGGCAGAG | ATTTACGATC | 400 |
| TAGCGTGGTC | ACCTGATAAC | AGGAACATAG | TGGTGGCATG | TATGGACAAT | 450 |
| TCGATACGAC | TGTTCGATGT | GGAGCTGGG | ATGCTGGTAT | GCGGCCAGTC | 500 |
| GGATCATGGT | CACTACGTCC | AAGGTCTTGC | ATGGGACCCA | TTAAATCAGT | 550 |
| TTATTCTCTC | ACAGTCTGCG | GACCGGTCTC | TGCATGTATA | TGGAGTCATT | 600 |
| CTTTCATCTG | CAGGAGTTAG | TTACAGGGCT | TGAAACTTTA | GAAGTAAGGT | 650 |
| TGCCAAGGCA | GAACTGCCTT | GTCCAGGTGA | TGTCCTGAGG | ACAAATTACT | 700 |
| TTTTCACAAC | GAGACGCTAC | CTTCATTCTT | TAGGCGATGC | AGCATATCGC | 750 |
| CTTGTGGTGG | TTTGGTCGTA | ATTCCAGTG | GTGTGTATAA | GGTGGCTGGT | 800 |
| GATGAAGTCG | CGAACTGCGT | ATACGTGTAT | ACTAGATCTG | GAATACTGAA | 850 |
| CAGCGCTGGT | GGCGTTAAAA | ACCGGCCTGC | GATTAGAATC | CCATCTTTGA | 900 |
| AGAAACCAGC | GCTGATGGCG | GCTTTCTCGC | CCGTATTTTA | CGAAACGTGC | 950 |
| CAGAAGAGTG | TGCTTAAGCT | GCCCTATAAG | CTAGTATTTG | CCATAGCAAC | 1000 |
| GACTAACGAA | GTACTCGTGT | ACGACACGGA | TGTATTGGAG | CCGTTATGCG | 1050 |
| TTGTGGGAAA | TATACATTAC | TCACCCATAA | CTGATTTAGC | ATGGTCTGAG | 1100 |
| GATGGCTCGA | CCCTACTAAT | CTCATCAACA | GACGGATTCT | GTTCGTATGT | 1150 |
| ATCGATCGAC | ACAGAAACGC | AATTCGGTTC | AAGGATAGAG | CCGCCAGCGA | 1200 |
| TGCATGCAGA | GCCACTAGAC | ACTGACGAGA | GCGCGGTAGC | GGCTAAGAAC | 1250 |
| CAGCGCGAGG | CAGGTGGGAT | CGTGAACATG | CTGCCGGTGA | AGAAGATCCC | 1300 |
| CTGCAATAGT | AGCGATAGTA | AAAAGAGGCG | CATACATCCT | ACGCCAGTCG | 1350 |
| ATTTGTGATT | TTTAATATAT | TTAATGCGGT | ACATAAGAAT | GCCTAATCTA | 1400 |
| GTTTGCCAGC | GAAGATATTT | TCCATTGTGT | GCTCAATGGA | CCCTGTGTTC | 1450 |
| CTGAGATCTT | GCACGACTTT | TTCCTGAGGC | ACATGTGGCG | CCATCGTCAT | 1500 |

```
CACGATTTCA ACCATGTCAC TATTAACGGC TCTCTTTCGA TCACTACCAT      1550
GTCTGTTTAA CCGAGCAACG CGTTCCTCCG GAGCCGATGG TACTGGCTCC      1600
GGAGAAGGGT CGTTGGTGGC GACCGAGGGC GCCGGTTTGG CATCCTGTAC      1650
GGTCCGCAAG GGTACTTGCT TGGCGCCCCT GTGTTTCACG GTGTAAACAA      1700
ACAAGCACAC CATCGTCAGT ATAAAGCACT ATAGTCGAAC CATCCATTTT      1750
TACTTTTGTG CGCGTGGGTA GCCGTGCCTC GTCTGTGTGT GTGGGAATGT      1800
ATAAATGTGT CCCGAGTTAT TATTCTAAAG CGGGCACCAT TGTAGTAACT      1850
TATTGCGAAA TTTCTGCTCT TCTCGTCTCG CTCAAAAATC GCGTTCAGGG      1900
TAAAAGGGGC GAAACAGAGG GCCAGATAGA AATTTCGAGA AACGGGTCA       1950
CCCCGCCCCT GCATTTTGAT ATGGCGTATT TGGGATTGCT TGCTCGAAAG      2000
TGTCTAAGTC CGGCTGGCGG GCCTGGCGCC CTCGCCGAAG GGAGATAGGA      2050
AGGGCGGGG GTCCGGGCAG CGGCTATGGT GTCAGTTACC TAGGGAAGGA       2100
GAAGGGGTA GAACCAAGGG GCTAGCACAC TCACCCTGGG GCCCCGTCT        2150
AGCCAAGCTT AAATATAAAT ACTAATGTAA CTATAAATAT AAGGATCTAC      2200
CGTGTCATTG CACATCCACC CACCCGTCGA TTAAAAAACC AAACAAAGCA      2250
AAGAATACAA TAGCAACGCA AGATCAACAC AATGGCTCTC ATCGTGGCAT      2300
CTTTGTTTTT GCCCTACCAA CCACAATTCG AGCTTGACAC CTCTCTCCCT      2350
GAGAACTCGC AGGTGGACTC ATCTCTCGTG AACATCCAGG CTATGGCCAA      2400
TGACCAACAG CAACAACGTG CGCTTTCTAA CAACATCTCA CAGGAATCAT      2450
TGGTCGCGCC AGCACCAGAA CAAGGTGTCC CCCCAGCAAT CTCAAGGAGT      2500
GCCACCAGGT CACCCAGTGC TTTCAACCGC GCCTCGTCTA CGACAAATAC      2550
TGCCACTTTA GATGATCTTG TCTCTTCGGA CATATTCATG GAAAACTTGA      2600
CTGCGAATGC AACTACCTCA CATACGCCAA CAAGCAAGAC TATGCTTAAA      2650
CCCCGGAAAA ATGGTTCCGT GGAACGATTC TTCTCCCCTT CTTCCAATAT      2700
TCCCACGGAT CGCATCGCAT CGCCAATCCA GCATGAGCAT GACTCCGGTT      2750
CGAGAATTGC TTCGCCAATC CAACAGCAAC AGCAGGACCC CACGACCAAC      2800
TTATTAAAGA ACGTCAACAA GTCATTGTTA GTGCACTCAC TGTTGAACAA      2850
CACCTCACAA ACTAGCCTAG AAGGACCCAA CAACCACATT GTTACCCCGA      2900
AATCGAGGGC GGGCAACAGG CCTACTTCGG CGGCTACTTC TTTAGTTAAT      2950
AGGACCAAAC AAGGTTCGGC CTCCTCTGGA TCTTCTGGGT CTTCTGCGCC      3000
ACCTTCCATT AAAAGGATTA CGCCCCACTT GACTGCGTCT GCTGCAAAAC      3050
AGCGTCCCTT ATTGGCTAAA CAGCCTTCTA ATCTGAAATA TTCGGAGTTA      3100
GCAGATATTT CGTCGAGTGA GACGTCTTCG CAGCATAATG AGTCGGACCC      3150
GGATGATCTA ACTACTGCCC CTGACGAGGA ATATGTTTCT GATTTGGAAA      3200
TGGATGACGC GAAGCAGGAC TACAAGGTTC CAAAGTTCGG CGGCTATTCC      3250
AATAAATCTA AACTTAAGAA ATATGCGCTG TTAAGGTCAT CTCAGGAGCT      3300
GTTTAGCCGT CTTCCATGGT CGATCGTTCC CTCTATCAAA GGTAATGGCG      3350
CCATGAAGAA CGCCATAAAC ACTGCAGTCT TGGAGAATAT CATTCCGCAC      3400
CGTCATGTTA AGTGGGTCGG TACCGTCGGA ATCCCAACGG ATGAGATTCC      3450
GGAAAATATC CTTGCGAACA TCTCTGACTC TTTAAAAGAC AAGTACGACT      3500
```

```
CCTATCCTGT  CCTTACGGAC  GACGACACCT  TCAAAGCCGC  ATACAAAAAC            3550
TACTGTAAAC  AAATCTTGTG  GCCTACGCTG  CATTACCAGA  TTCCAGACAA            3600
TCCGAACTCG  AAGGCTTTTG  AAGATCACTC  TTGGAAGTTC  TATAGAAACT            3650
TAAACCAAAG  GTTTGCGGAC  GCGATCGTTA  AAATCTATAA  GAAAGGTGAC            3700
ACCATCTGGA  TTCATGATTA  CCATTTAATG  CTGGTTCCGC  AGATGGTGAG            3750
AGACGTCTTG  CCTTTTGCCA  AAATAGGATT  TACCTTACAT  GTCTCGTTCC            3800
CCAGTAGTGA  AGTGTTTAGG  TGTCTGGCTC  AGCGTGAGAA  GATCTTAGAA            3850
GGCTTGACCG  GTGCAGACTT  TGTCGGCTTC  CAGACGAGGG  AGTATGCAAG            3900
ACATTTCTTA  CAGACGTCTA  ACCGTCTGCT  AATGGCGGAC  GTGGTACATG            3950
ATGAAGAGCT  AAAGTATAAC  GGCAGAGTCG  TTTCTGTGAG  GTTCACCCCA            4000
GTTGGTATCG  ACGCCTTTGA  TTTGCAATCG  CAATTGAAGG  ATGGAAGTGT            4050
CATGCAATGG  CGTCAATTGA  TTCGTGAAAG  ATGGCAAGGG  AAAAAACTAA            4100
TTGTGTGTCG  TGATCAATTC  GATAGAATTA  GAGGTATTCA  CAAGAAATTG            4150
TTGGCTTATG  AAAAATTCTT  GGTCGAAAAT  CCGGAATACG  TGGAAAAATC            4200
GACTTTAATT  CAAATCTGTA  TTGGAAGCAG  TAAGGATGTA  GAACTGGAGC            4250
GCCAGATCAT  GATTGTCGTG  GATAGAATCA  ACTCGCTATC  CACCAATATT            4300
AGTATTTCTC  AACCTGTGGT  GTTTTGCAT   CAAGATCTAG  ATTTTTCTCA            4350
GTATTTAGCT  TTGAGTTCAG  AGGCAGATTT  GTTCGTAGTC  AGCTCTCTAA            4400
GGGAAGGTAT  GAACTTGACA  TGTCACGAAT  TTATCGTTTG  TTCTGAGGAC            4450
AAAAATGCTC  CCCTACTGTT  GTCAGAATTT  ACTGGTAGTG  CATCTTTATT            4500
GAATGATGGC  GCTATAATAA  TTAACCCATG  GGATACCAAG  AACTTCTCAC            4550
AAGCCATTCT  CAAGGGGTTG  GAGATGCCAT  TCGATAAGAG  AAGGCCACAG            4600
TGGAAGAAAT  TGATGAAAGA  CATTATCAAC  AACGACTCTA  CAAACTGGAT            4650
CAAGACTTCT  TTACAAGATA  TTCATATTTC  GTGGCAATTC  AATCAAGAAG            4700
GTTCCAAGAT  CTTCAAATTG  AATACAAAAA  CACTGATGGA  AGATTACCAG            4750
TCATCTAAAA  AGCGTATGTT  TGTTTTCAAC  ATTGCTGAAC  CACCTTCATC            4800
GAGAATGATT  TCCATACTGA  ATGACATGAC  TTCTAAGGGC  AATATCGTTT            4850
ACATCATGAA  CTCATTTCCA  AAGCCCATTC  TGGAAAATCT  TTACAGTCGT            4900
GTGCAAAACA  TTGGGTTGAT  TGCCGAGAAT  GGTGCATACG  TTAGTCTGAA            4950
CGGTGTATGG  TACAACATTG  TTGATCAAGT  CGATTGGCGT  AACGATGTAG            5000
CCAAAATTCT  CGAGGACAAA  GTGGAGAGAT  TACCTGGCTC  GTACTACAAG            5050
ATAAATGAGT  CCATGATCAA  GTTCCACACT  GAAATGCGG   AAGATCAAGA            5100
TCGTGTAGCT  AGTGTTATCG  GTGATGCCAT  CACACATATC  AATACTGTTT            5150
TTGACCACAG  AGGTATTCAT  GCCTACGTTT  ACAAAAACGT  TGTTTCCGTA            5200
CAACAAGTGG  GACTTTCCTT  ATCGGCAGCT  CAATTTCTTT  TCAGATTCTA            5250
TAATTCTGCT  TCGGATCCAC  TGGATACGAG  TTCCGGCCAA  ATCACAAATA            5300
TTCAGACACC  ATCTCAACAA  AATCCTTCAG  ATCAAGAACA  ACAACCTCCA            5350
GCCTCTCCCA  CTGTGTCGAT  GAACCATATT  GATTCGCAT   GTGTCTCTGG            5400
TTCATCGTCT  CCTGTGCTTG  AACCATTGTT  CAAATTGGTC  AATGATGAAG            5450
CAAGTGAAGG  GCAAGTAAAA  GCCGGACACG  CCATTGTTTA  TGGTGATGCT            5500
```

```
ACTTCTACTT ATGCCAAAGA ACATGTAAAT GGGTTAAACG AACTTTTCAC                5550

GATCATTTCA AGAATCATTG AAGATTAAAT TTTACCATTT TAAAATTTTA                5600

ATGTTCTTGG GTATGAACTT TTATTTTCAA CTGCTTATTA TATATCAATT                5650

CTATAAATTT TTTTCTTCTC TCTAACGACC AATTATAAAA TTCATCCTCT                5700

TATTTATTAC AGCATCTTAT ACATTATGTA TATGGGTAGC TATTATTCAT                5750

TTTTGCTTCG TAAGGACTTT TTTTGTCAAC TTTTCATCC  TAAGCGGCTA                5800

AAAGTGATTG GAGAGGAATG TCCAGGCGAC CAATGATAAA AACGCTTCT                 5850

CTTGGAACAA GAAATAGGAG CAATTGACAG TTGTCGATGA ACAGCGAAAA                5900

TAGTAAGATA ACCTTCAAGC CCAATATTCT AATTAAAGGC GTTTATATAT                5950

TTGTACTTTA TGGTATGTGC ATATGTATTG T                                    5981
```

( 2 ) INFORMATION FOR SEQ ID NO:84:

( i ) SEQUENCE CHARACTERISTICS:
        ( A ) LENGTH:50 base pairs
        ( B ) TYPE: Nucleotide
        ( C ) STRANDEDNESS: Doublestranded
        ( D ) TOPOLOGY: Linear ( i i ) MOLECULE TYPE: Synthetic DNA ( i i i ) HYPOTHETICAL: No ( i v ) ANTI-SENSE: No ( x i ) SEQUENCE DESCRIPTION: SEQ ID NO:84:

```
CGGGAAGACA TAGAACTATG ACTACGGATA ACGCTAAGGC GCAACTGACC                50
```

( 2 ) INFORMATION FOR SEQ ID NO:85:

( i ) SEQUENCE CHARACTERISTICS:
        ( A ) LENGTH:48 basepairs
        ( B ) TYPE: Nucleotide
        ( C ) STRANDEDNESS: Doublestranded
        ( D ) TOPOLOGY: Linear ( i i ) MOLECULE TYPE: Synthetic DNA ( i i i ) HYPOTHETICAL: No ( i v ) ANTI-SENSE: No ( x i ) SEQUENCE DESCRIPTION: SEQ ID NO:85:

```
GGGCCCAACA ACACAATGGT TACCCCGAAA TCGAGGGCGG GCAACAGG                  48
```